US008809543B2

(12) United States Patent

Arai et al.

(10) Patent No.: US 8,809,543 B2

(45) Date of Patent: Aug. 19, 2014

(54) ELECTROPHOTOGRAPHIC PHOTORECEPTOR, ELECTROPHOTOGRAPHIC IMAGE FORMING METHOD, ELECTROPHOTOGRAPHIC IMAGE FORMING APPARATUS, AND PROCESS CARTRIDGE FOR ELECTROPHOTOGRAPHIC IMAGE FORMING APPARATUS

(75) Inventors: Ryota Arai, Shizuoka (JP); Tomoyuki Shimada, Shizuoka (JP)

(73) Assignee: Ricoh Company, Ltd., Tokyo (JP)

( * ) Notice: Subject to any disclaimer, the term of this patent is extended or adjusted under 35 U.S.C. 154(b) by 21 days.

(21) Appl. No.: 13/231,382

(22) Filed: Sep. 13, 2011

(65) Prior Publication Data

US 2012/0064443 A1 Mar. 15, 2012

(30) Foreign Application Priority Data

Sep. 14, 2010 (JP) ................................ 2010-205356
Sep. 24, 2010 (JP) ................................ 2010-213286

(51) Int. Cl.

*C07D 209/08* (2006.01)
*C07D 209/12* (2006.01)
*C07D 401/04* (2006.01)

(52) U.S. Cl.

USPC ........................................ 546/277.4; 548/470

(58) Field of Classification Search

USPC ........................................................ 548/470
See application file for complete search history.

(56) References Cited

FOREIGN PATENT DOCUMENTS

| | | |
|---|---|---|
| JP | 60-196768 | 10/1985 |
| JP | 4-10507 | 2/1992 |
| JP | 5-19701 | 3/1993 |
| JP | 7-91478 | 10/1995 |
| JP | 2732697 | 12/1997 |
| JP | 2884353 | 2/1999 |
| JP | 4101676 | 3/2008 |
| JP | 4226749 | 12/2008 |

OTHER PUBLICATIONS

Mallory, et al. Document No. 149:555077, retrieved from CAPLUS; Nov. 19, 2008.*
Yauchi, et al. Document No. 142:363424, retrieved from CAPLUS; Mar. 31, 2005.*
Kohama, et al. Document No. 137:270729, retrieved from CAPLUS; Oct. 4, 2002.*
Gauvin, et al. Document No. 132:28036, retrieved from CAPLUS; Nov. 10, 1999.*
Ding, et al. Document No. 131:258033, retrieved from CAPLUS; Aug. 18, 1999.*
Carmody, et al. Document No. 86:16178, retrieved from CAPLUS; May 12, 1984.*
Olliero, et al. Document No. 83:192999, retrieved from CAPLUS; May 12, 1984.*
White, et al. Document No. 74:125320, retrieved from CAPLUS; May 12, 1984.*
Norton. Document No. 56:38434, retrieved from CAPLUS; Apr. 22, 2001.*

* cited by examiner

*Primary Examiner* — Shawquia Young

(74) *Attorney, Agent, or Firm* — Oblon, Spivak, McClelland, Maier & Neustadt, L.L.P.

(57) ABSTRACT

An N-phenyl-diphenylisoindole derivative having the following formula (1):

(1)

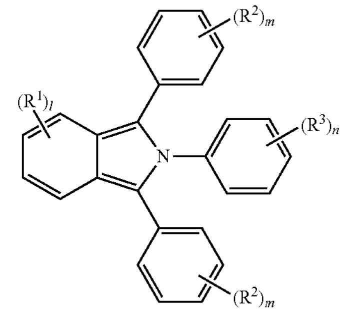

wherein each of $R^1$ and $R^2$ represents a hydrogen atom, a substituted or an unsubstituted alkyl group, a substituted or an unsubstituted alkoxy group, a substituted or an unsubstituted phenyl group, or a substituted or an unsubstituted phenoxy group; $R^3$ represents a hydrogen atom, a substituted or an unsubstituted alkyl group, a substituted or an unsubstituted alkoxy group, a substituted or an unsubstituted phenyl group, a substituted or an unsubstituted phenoxy group, or has the following formula (2):

(2)

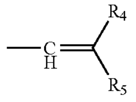

wherein each of $R_4$ and $R_5$ represents a substituted or an unsubstituted alkyl group, or a substituted or an unsubstituted phenyl group; 1 represents an integer of from 1 to 4; and each of m and n represents an integer of from 1 to 5.

20 Claims, 7 Drawing Sheets

| Rank | Rank Standard | Level Sample | | |
|---|---|---|---|---|
| | | 8pt | 2 by 2 | 1 by 1 |
| 5 | Not blurred at all |  |  |  |
| 4 | Blurred, but 1by 1 dot is visible |  |  |  |
| 3 | Blurred, but 2 by 2 dot is visible |  |  |  |
| 2 | Blurred, and Even 2 by 2 dot is not visible |  |  |  |
| 1 | 8pt letter is not identified |  |  |  |

ELECTROPHOTOGRAPHIC PHOTORECEPTOR, ELECTROPHOTOGRAPHIC IMAGE FORMING METHOD, ELECTROPHOTOGRAPHIC IMAGE FORMING APPARATUS, AND PROCESS CARTRIDGE FOR ELECTROPHOTOGRAPHIC IMAGE FORMING APPARATUS

CROSS-REFERENCE TO RELATED APPLICATIONS

This patent application is based on and claims priority pursuant to 35 U.S.C. §119 to Japanese Patent Applications Nos. 2010-205356 and 2010-213286, filed on Sep. 14, 2010 and Sep. 24, 2010, respectively in the Japanese Patent Office, the entire disclosure of which is hereby incorporated herein by reference.

FIELD OF THE INVENTION

The present invention relates to an N-phenyl-diphenyl-isoindole derivative effectively used as an organic photoconductor and a method of preparing the N-phenyl-diphenyl-isoindole derivative. Further, the present invention relates to an electrophotographic photoreceptor including at least one specific isoindole derivative in its photosensitive layer, and to an electrophotographic image forming method, an electrophotographic image forming apparatus and a process cartridge therefor using the electrophotographic photoreceptor.

BACKGROUND OF THE INVENTION

Recently, information-processing systems using an electrophotographic method are making a remarkable progress. In particular, laser printers and digital copiers which record data with light by changing the data into digital signals make remarkable improvements in their printing qualities and reliabilities. Further, technologies used in these printers and copiers are applied to laser printers and digital copiers capable of printing full-color images with high-speed printing technologies. Because of these reasons, photoreceptors are required both to produce high-quality images and to have high durability.

Photoreceptors using organic photosensitive materials are widely used for these laser printers and digital copiers due to their cost, productivity and non-polluting properties. The organic photoreceptors are typically classified to a single-layered type and a functionally-separated type. The first practical organic photoreceptor, i.e., PVK-TNF charge transfer complex photoreceptor was the former single-layered type.

In 1968, Mr. Hayashi and Mr. Regensburger independently invented PVK/a-Se multi-layered photoreceptor. In 1977, Mr. Melz, and in 1978, Mr. Schlosser disclosed multi-layered photoreceptors whose photosensitive layers are all formed from organic materials, i.e., an organic-pigment dispersed layer and an organic low-molecular-weight material dispersed polymer layer. These are called as functionally-separated photoreceptors because of having a charge generation layer (CGL) generating a charge by absorbing light and a charge transport layer (CTL) transporting the charge and neutralizing the charge on the surface of the photoreceptor.

However, the photosensitive layer of the organic photoreceptor is easily abraded due to repeated use, and therefore potential and photosensitivity of the photoreceptor are likely to deteriorate, resulting in background fouling due to a scratch on the surface thereof and deterioration of density and quality of the resultant images. Therefore, abrasion resistance of the organic photoreceptor has been an important subject. Further, recently, in accordance with speeding up of printing and downsizing of image forming apparatus, the photoreceptor has to have a smaller diameter, and durability thereof has become a more important subject.

As a method of improving the abrasion resistance of the photoreceptor, methods of imparting lubricity to the photosensitive layer, hardening the photosensitive layer, including a filler therein and using a polymeric charge transport material (CTM) instead of a low-molecular-weight CTM are widely known. However, another problem occurs when these methods are used to prevent the abrasion of the photoreceptor. Namely, an oxidized gas such as ozone and NOx arising due to use conditions or environment, adheres to the surface of the photosensitive layer and decreases the surface resistance thereof, resulting in a problem such as blurring of the resultant images. So far, such a problem has been avoided to some extent because the material causing the blurred images are gradually scraped off in accordance with the abrasion of the photosensitive layer.

However, in order to comply with the above-mentioned recent demand for higher sensitivity and durability of the photoreceptor, a new technology has to be imparted thereto. In order to decrease an influence of the material causing the blurred images, there is a method of equipping the photoreceptor with a heater, which is a large drawback for downsizing the apparatus and decreasing power consumption. In addition, a method of including an additive such as an antioxidant in the photosensitive layer is effective, but since a simple additive does not have photoconductivity, and a large amount thereof in the photosensitive layer causes problems such as deterioration of the sensitivity and increase of residual potential of the resultant photoreceptor.

As mentioned above, the electrophotographic photoreceptor having less abrasion by being imparted with abrasion resistance or a process design around thereof inevitably produces blurred and low-resolution images, and it is difficult to have both of high durability and high quality of the resultant images. This is because high surface resistance of the photosensitive layer is preferable to prevent the blurred images and low surface resistance thereof is preferable to prevent the increase of residual potential.

Most of the electrophotographic photoreceptors in the market are functionally-separated photoreceptors each including an electroconductive substrate, a CGL and a CTL layered thereon, and a CTM included in the CTL is a positive hole transport material. These are mostly used in negatively-charging electrophotographic processes.

A reliable charging method in the electrophotographic processes is a corona discharge, and most of copiers and printers use the corona discharge. As widely known, a negative-polarity corona discharge is more unstable than a positive-polarity corona discharge, and therefore a scorotron charging method is used, resulting in one of cost increase elements. The negative-polarity corona discharge generates more ozone causing chemical damages, and when used for a long time, the ozone oxidizes a binder resin and a CTM, and ionic compounds produced in charging such as nitrogen-oxide ions, sulfur oxide ions and ammonium ions accumulate on the surface of a photoreceptor, resulting in deterioration of image quality. Therefore, ozone filters are used in negatively-charging copiers and printers to prevent the ozone from discharging out in many cases, resulting in cost increase. Further, a large amount of ozone causes environmental pollution.

In order to solve these problems, positively-charged electrophotographic photoreceptors are being developed. The positively-charged electrophotographic photoreceptors generate less ozone and NOx ions, and further produce stable images with less environmental variation with two-component developers widely used at present.

However, the positively-charged single-layered or reverse-layered photoreceptor has a drawback of varying in its properties due to an environmental gas such as exhaust gases from blue heaters and cars because of including a charge generation material (CGM) vulnerable to oxidizing materials such as ozone and NOx ions at the surface.

In contrast, the negatively-charged electrophotographic photoreceptor is preferably used rather than the positively-charged electrophotographic photoreceptor in a high-speed copy process. This is because an organic material having high charge transportability even in the high-speed copy process is at present almost limited to a positive hole transport material, and a normally-layered electrophotographic photoreceptor having a CTL including a positive hole transport material at the surface is limited to be negatively charged in principle.

As mentioned above, a positively and negatively chargeable electrophotographic photoreceptor can further expand its applications, and is advantageous for cost reduction due to model reduction and higher speed.

Japanese Patent No. 2732697 discloses a positively and negatively chargeable electrophotographic photoreceptor. However, a diphenoquinone derivative as an electron transport material used therein has slightly low charge transportability, and the photoreceptor does not have sufficient sensitivity for higher speed and smaller copiers and printers. Further, the photoreceptor has a drawback of producing blurred images after repeatedly used.

Japanese published unexamined application No. 2000-231204 discloses an aromatic compound having a dialkylamino group as a deoxidizer. This compound is effectively included in a photoreceptor to produce quality image even after repeatedly used. However, the compound having low charge transportability is difficult to comply with higher sensitivity and speed, and therefore a content thereof has a limit.

Further, a stilbene compound having a dialkylamino group disclosed in Japanese published unexamined application No. 60-196768 and Japanese Patent No. 2884353 has an effect on the blurred images due to the oxidizing gas on page 37 of Konica Technical Report Vol. 13 written by Itami, etc. and published in 2000.

However, since the compound has a substituted dialkylamino group having a strong mesomeric effect (+M effect) at a resonance portion in its triarylamine structure, which is a charge transport site, total ionization potential is extremely small. Therefore, the compound has a critical defect of being quite difficult to practically use because charge retainability of a photosensitive layer in which the compound is used alone as a CTM largely deteriorates from the beginning or after repeated use. In addition, even when the above-mentioned stilbene compound is used together with other CTMs as it is in the present invention, the compound has a considerably smaller ionization potential than the other CTMs and becomes a trap site against a charge transport, and therefore, the resultant photoreceptor has quite a low sensitivity and a large residual potential.

Japanese published unexamined application No. 2004-258253 discloses a photoreceptor including a stilbene compound and a specific diamine compound having improved environmental resistance to repeated use and oxidizing gases without deterioration of sensitivity.

However, this is not sufficient for a high-speed printing photoreceptor having a smaller diameter.

Because of these reasons, a need exists for an electrophotographic photoreceptor having high durability against repeated use for a long time, preventing deterioration of image density and blurred images and stably producing quality images.

SUMMARY OF THE INVENTION

Accordingly, an object of the present invention is to provide an electrophotographic photoreceptor having high durability against repeated use for a long time, preventing deterioration of image density and blurred images and stably producing high-quality images.

Another object of the present invention is to provide an electrophotographic image forming method using the photoreceptor.

A further object of the present invention is to provide an electrophotographic image forming apparatus using the photoreceptor.

Another object of the present invention is to provide a process cartridge using the photoreceptor for electrophotographic image forming apparatus.

These objects and other objects of the present invention, either individually or collectively, have been satisfied by the discovery of an N-phenyl-diphenylisoindole derivative having the following formula (1):

(1)

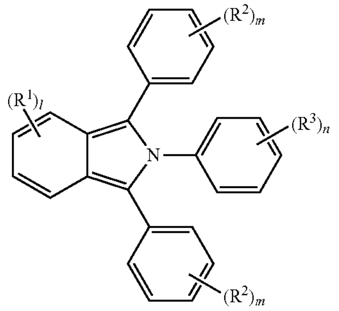

wherein each of $R^1$ and $R^2$ represents a hydrogen atom, a substituted or an unsubstituted alkyl group, a substituted or an unsubstituted alkoxy group, a substituted or an unsubstituted phenyl group, or a substituted or an unsubstituted phenoxy group; $R^3$ represents a hydrogen atom, a substituted or an unsubstituted alkyl group, a substituted or an unsubstituted alkoxy group, a substituted or an unsubstituted phenyl group, a substituted or an unsubstituted phenoxy group, or has the following formula (2):

(2)

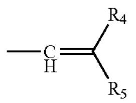

wherein each of $R_4$ and $R_5$ represents a substituted or an unsubstituted alkyl group, or a substituted or an unsubstituted phenyl group; l represents an integer of from 1 to 4; and each of m and n represents an integer of from 1 to 5.

These and other objects, features and advantages of the present invention will become apparent upon consideration of the following description of the preferred embodiments of the present invention taken in conjunction with the accompanying drawings.

BRIEF DESCRIPTION OF THE DRAWINGS

Various other objects, features and attendant advantages of the present invention will be more fully appreciated as the same becomes better understood from the detailed description when considered in connection with the accompanying drawings in which like reference characters designate like corresponding parts throughout and wherein.

DETAILED DESCRIPTION OF THE INVENTION

Figure 1:
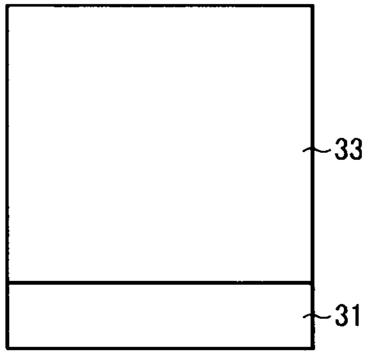
FIG. 1 is a cross-sectional view of an embodiment of the photosensitive layer of the electrophotographic photoreceptor of the present invention.

The present invention provides a an electrophotographic photoreceptor having high durability against repeated use for a long time, preventing deterioration of image density and blurred images and stably producing high-quality images, and which is positively and negatively chargeable so as not to need a replacement and capable of downsizing the apparatus in compliance with the high-speed printing or smaller diameter of the photoreceptor.

More particularly, the present invention relates to an N-phenyl-diphenylisoindole derivative having the following formula (1):

(1)

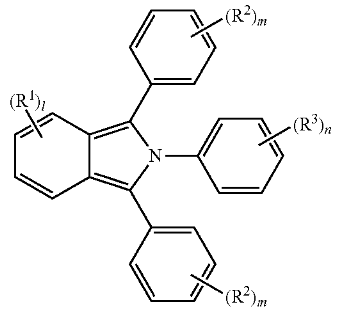

wherein each of $R^1$ and $R^2$ represents a hydrogen atom, a substituted or an unsubstituted alkyl group, a substituted or an unsubstituted alkoxy group, a substituted or an unsubstituted phenyl group, or a substituted or an unsubstituted phenoxy group; $R^3$ represents a hydrogen atom, a substituted or an unsubstituted alkyl group, a substituted or an unsubstituted alkoxy group, a substituted or an unsubstituted phenyl group, a substituted or an unsubstituted phenoxy group, or has the following formula (2):

(2)

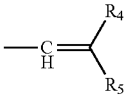

wherein each of $R_4$ and $R_5$ represents a substituted or an unsubstituted alkyl group, or a substituted or an unsubstituted phenyl group; l represents an integer of from 1 to 4; and each of m and n represents an integer of from 1 to 5.

The photoreceptor of the present invention including at least one isoindole derivative having the following formula in its photosensitive layer does not produce blurred (distorted) images due to oxidizing gases and is positively and negatively chargeable:

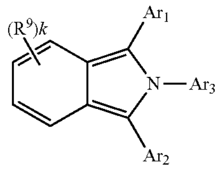

wherein $R^9$ represents a hydrogen atom, a substituted or an unsubstituted alkyl group, a substituted or an unsubstituted alkoxy group, a halogen atom, or a substituted or an unsubstituted aryl group; each of $Ar_1$, $Ar_2$ and $Ar_3$ represents a substituted or an unsubstituted aryl group, or has the following formula:

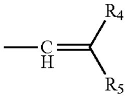

wherein each of $R_4$ and $R_5$ represents a substituted or an unsubstituted alkyl group, or a substituted or an unsubstituted phenyl group, or

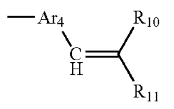

wherein each of $R_{10}$ and $R_{11}$ represents a substituted or an unsubstituted alkyl group, or a substituted or an unsubstituted aryl group; $Ar_4$ represents a substituted or an unsubstituted arylene group; $R_{10}$ and $R_{11}$ may form a ring together, and k represents an integer of from 1 to 4.

In the present invention, a reason why the isoindole derivative is effectively used to maintain image quality against repeated use is not clarified yet. However, the indole group in a chemical structure has high basicity and is thought to electrically neutralize an oxidizing gas causing blurred images. In addition, the isoindole derivative in the present invention further increases sensitivity and stability against repeated use of the resultant photoreceptor when combined with other CTMs.

The isoindole derivative in the present invention is a positive hole transport material, and a photoreceptor using the isoindole derivative can be a positively and negatively chargeable single-layered photoreceptor with an electron transport material.

Hereinafter, details of the electrophotographic photoreceptor of the present invention, and an electrophotographic image forming method, an electrophotographic image forming apparatus and a process cartridge therefor using the electrophotographic photoreceptor are explained.

The isoindole derivative of the present invention included in a photosensitive layer having the following formula is explained in detail.

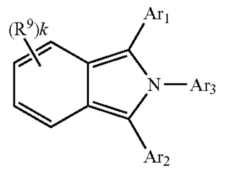

wherein $R^9$ represents a hydrogen atom, a substituted or an unsubstituted alkyl group, a substituted or an unsubstituted alkoxy group, a halogen atom, or a substituted or an unsubstituted aryl group; each of $Ar_1$, $Ar_2$ and $Ar_3$ represents a substituted or an unsubstituted aryl group, or has the following formula:

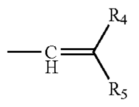

wherein each of $R_4$ and $R_5$ represents a substituted or an unsubstituted alkyl group, or a substituted or an unsubstituted phenyl group, or

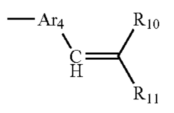

wherein each of $R_{10}$ and $R_{11}$ represents a substituted or an unsubstituted alkyl group, or a substituted or an unsubstituted aryl group; $Ar_4$ represents a substituted or an unsubstituted arylene group; $R_{10}$ and $R_{11}$ may form a ring together, and k represents an integer of from 1 to 4.

A method of preparing the isoindole derivative having the above-mentioned formula is disclosed in D. W. Jones, Journal of the Chemical Society, Perkin Transactions 1: Organic and Bio-Organic Chemistry, 21, 2728 (1972).

Specifically, a diketone derivative and an amine derivative are reacted with each other to prepare a pyrrole derivative in the first process, and the pyrrole derivative is oxidized to prepare the isoindole derivative having the above-mentioned formula in the second process.

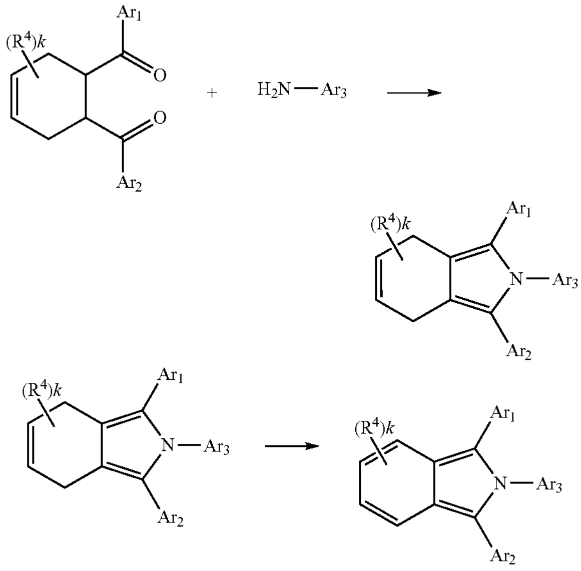

Specific examples of solvents for use in the above-mentioned reactions include, but are not limited to, benzene, toluene, xylene, chloronaphthalene, ethylacetate, pyridine, methylpyridine, N,N-dimethylformamide, N,N-dimethylacetoamide, carbon tetrachloride, chloroform, dichloromethane, etc.

A reaction temperature in the first process is preferably from 150 to 200° C., and 0 to 100° C. in the second process.

Specific examples of the alkyl group in the formula (1) include methyl, ethyl, propyl, butyl, hexyl, undecanyl groups, etc. Specific examples of the aromatic hydrocarbon group include aromatic monovalent groups such as benzene, biphenyl, naphthalene, anthracene, fluorene and pyrene; and aromatic heterocyclic monovalent groups such as pyridine, quinoline, thiophene, furan, oxazole, oxadiazole and carbazole. Specific examples of the arylene group include bivalent groups of the aromatic hydrocarbon group. Specific examples of the halogen atom include a fluorine atom, a chlorine atom, a boron atom and an iodine atom. Specific examples of their substituents include the above-mentioned specific examples of the alkyl group; an alkoxy group such as a methoxy group, an ethoxy group, a propoxy group and a butoxy group; a halogen atoms such as a fluorine atom, a chlorine atom, a bromine atom and an iodine atom; the above-mentioned aromatic hydrocarbon groups; and heterocyclic ring groups such as pyrrolidine, piperidine and piperazine.

Preferred embodiments of the isoindole derivative having the formula (1) include, but are not limited to, the following compounds.

TABLE 1-1
| | |
|---|---|
| 1 | 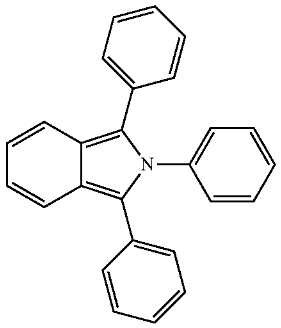 [SMILES: c1ccc(-c2c3ccccc3c(-c3ccccc3)n2-c2ccccc2)cc1] |
| 2 | 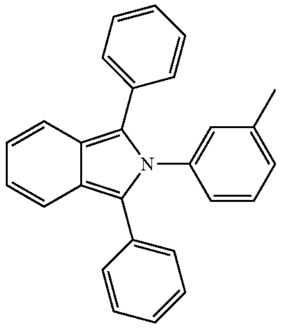 [SMILES: Cc1cccc(-n2c(-c3ccccc3)c3ccccc3c2-c2ccccc2)c1] |
| 3 | 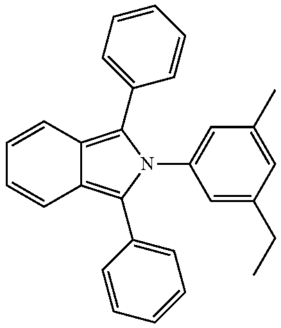 [SMILES: CCc1cc(C)cc(-n2c(-c3ccccc3)c3ccccc3c2-c2ccccc2)c1] |
| 4 | 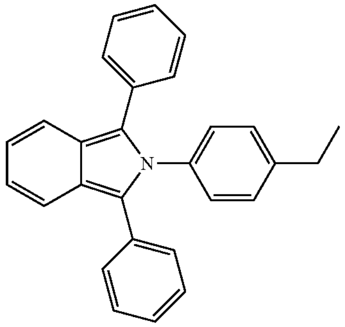 [SMILES: CCc1ccc(-n2c(-c3ccccc3)c3ccccc3c2-c2ccccc2)cc1] |
TABLE 1-2
| | |
|---|---|
| 5 | 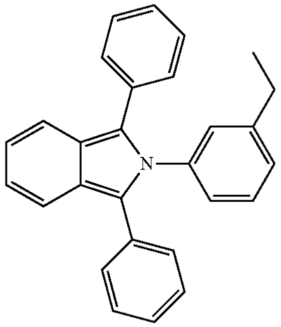 [SMILES: CCc1cccc(-n2c(-c3ccccc3)c3ccccc3c2-c2ccccc2)c1] |
| 6 | 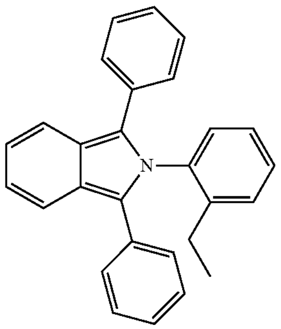 [SMILES: CCc1ccccc1-n1c(-c2ccccc2)c2ccccc2c1-c1ccccc1] |
| 7 | 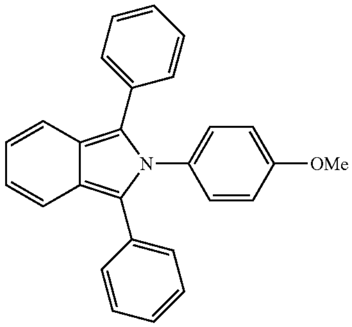 [SMILES: COc1ccc(-n2c(-c3ccccc3)c3ccccc3c2-c2ccccc2)cc1] |
| 8 | 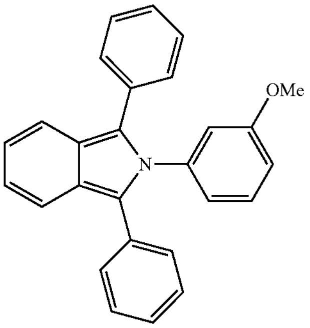 [SMILES: COc1cccc(-n2c(-c3ccccc3)c3ccccc3c2-c2ccccc2)c1] |

TABLE 1-2-continued
9
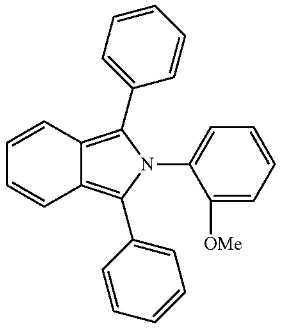 [SMILES: COc1ccccc1-n1c(-c2ccccc2)c2ccccc2c1-c1ccccc1]
TABLE 1-3
10
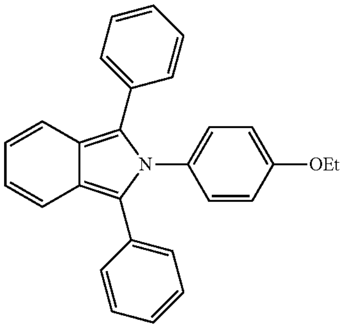 [SMILES: CCOc1ccc(-n2c(-c3ccccc3)c3ccccc3c2-c2ccccc2)cc1]
11
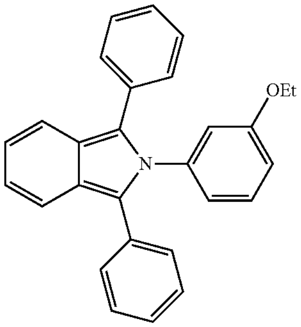 [SMILES: CCOc1cccc(-n2c(-c3ccccc3)c3ccccc3c2-c2ccccc2)c1]
12
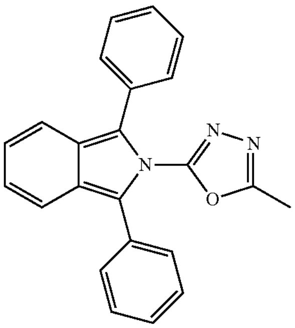 [SMILES: Cc1nnc(-n2c(-c3ccccc3)c3ccccc3c2-c2ccccc2)o1]
TABLE 1-3-continued
13
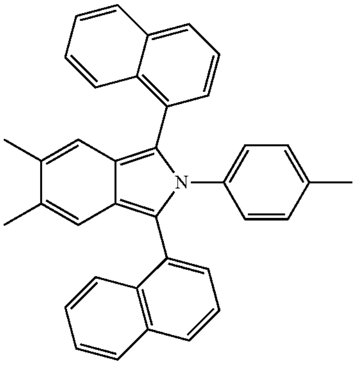
14
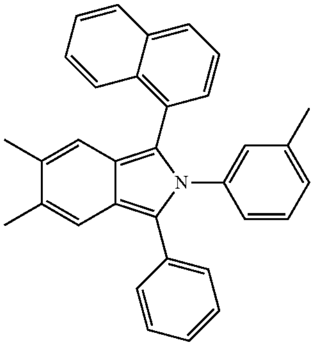
TABLE 1-4
15
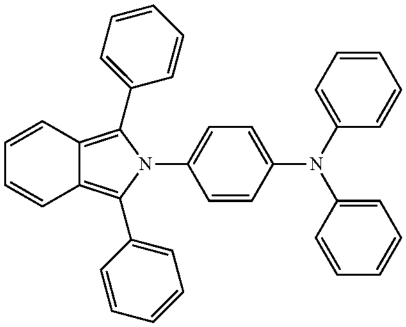 [SMILES: c1ccc(-c2c3ccccc3c(-c3ccccc3)n2-c2ccc(N(c3ccccc3)c3ccccc3)cc2)cc1]
16
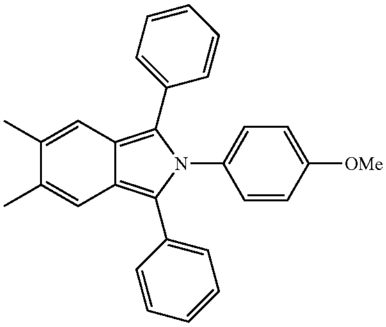 [SMILES: COc1ccc(-n2c(-c3ccccc3)c3cc(C)c(C)cc3c2-c2ccccc2)cc1]

TABLE 1-4-continued
17
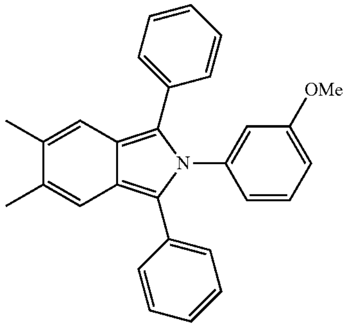 [SMILES: COc1cccc(-n2c(-c3ccccc3)c3cc(C)c(C)cc3c2-c2ccccc2)c1]
18
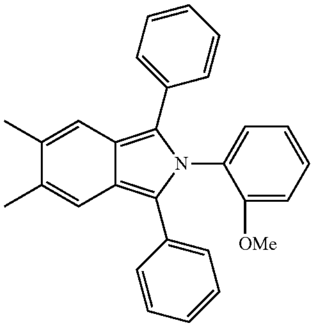 [SMILES: COc1ccccc1-n1c(-c2ccccc2)c2cc(C)c(C)cc2c1-c1ccccc1]
TABLE 1-5
19
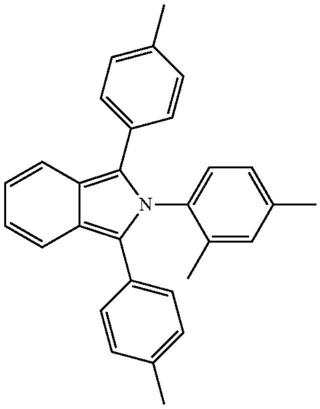 [SMILES: Cc1ccc(-c2c3ccccc3c(-c3ccc(C)cc3)n2-c2ccc(C)cc2C)cc1]
20
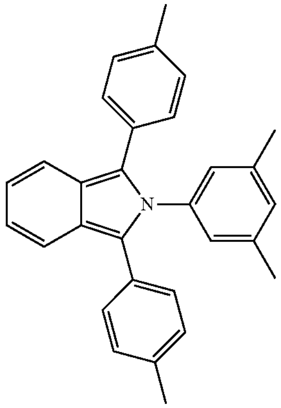 [SMILES: Cc1ccc(-c2c3ccccc3c(-c3ccc(C)cc3)n2-c2cc(C)cc(C)c2)cc1]
TABLE 1-5-continued
21
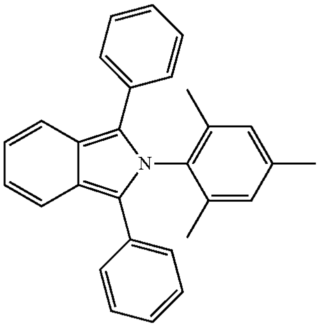 [SMILES: Cc1cc(C)c(-n2c(-c3ccccc3)c3ccccc3c2-c2ccccc2)c(C)c1]
22
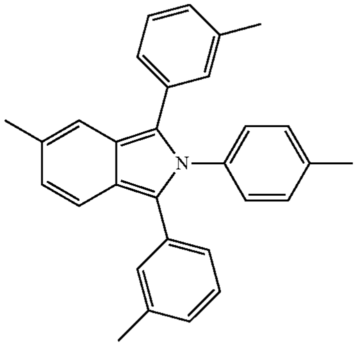
TABLE 1-6
23
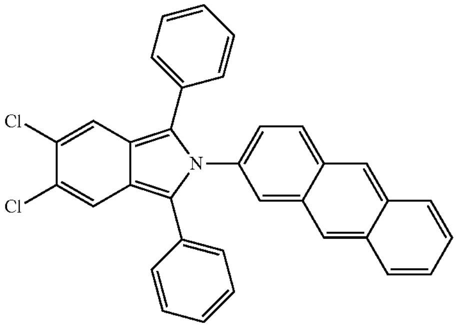 [SMILES: Clc1cc2c(-c3ccccc3)n(-c3ccc4cc5ccccc5cc4c3)c(-c3ccccc3)c2cc1Cl]
24
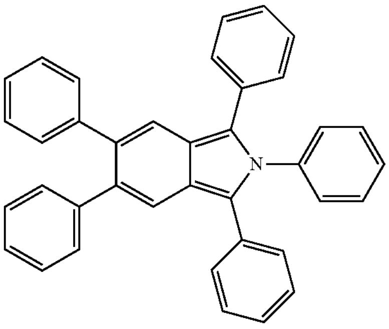 [SMILES: c1ccc(-c2cc3c(-c4ccccc4)n(-c4ccccc4)c(-c4ccccc4)c3cc2-c2ccccc2)cc1]

TABLE 1-6-continued
25
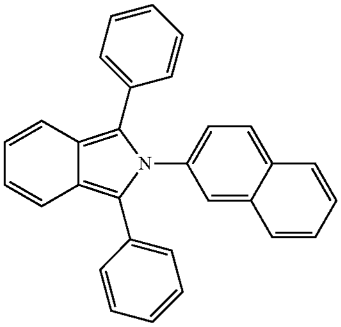 [SMILES: c1ccc(-c2c3ccccc3c(-c3ccccc3)n2-c2ccc3ccccc3c2)cc1]
26
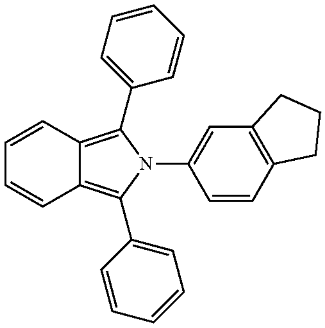 [SMILES: c1ccc(-c2c3ccccc3c(-c3ccccc3)n2-c2ccc3c(c2)CCC3)cc1]
27
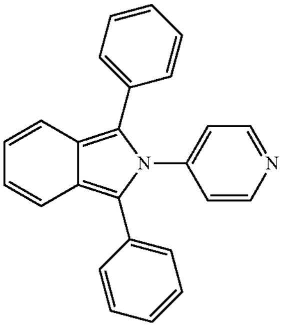 [SMILES: c1ccc(-c2c3ccccc3c(-c3ccccc3)n2-c2ccncc2)cc1]
TABLE 1-7
28
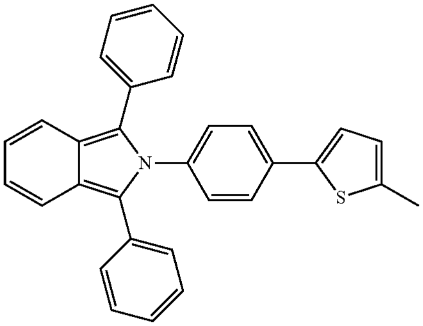 [SMILES: Cc1ccc(-c2ccc(-n3c(-c4ccccc4)c4ccccc4c3-c3ccccc3)cc2)s1]
TABLE 1-7-continued
29
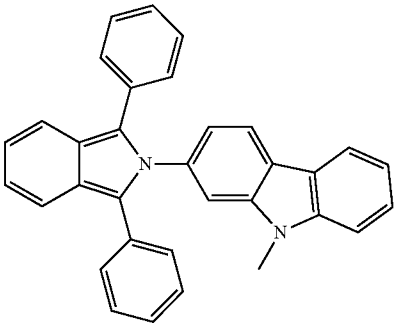 [SMILES: Cn1c2ccccc2c2ccc(-n3c(-c4ccccc4)c4ccccc4c3-c3ccccc3)cc21]
30
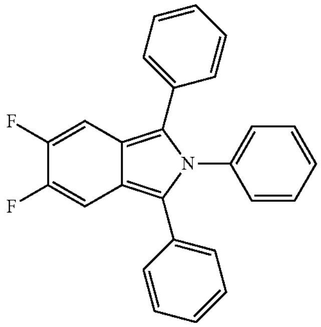 [SMILES: Fc1cc2c(-c3ccccc3)n(-c3ccccc3)c(-c3ccccc3)c2cc1F]
31
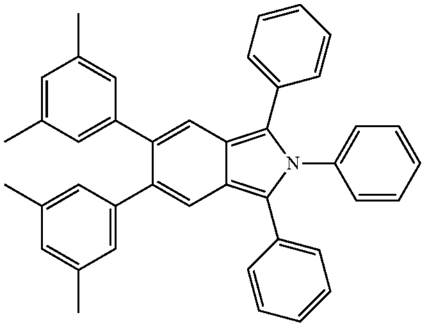 [SMILES: Cc1cc(C)cc(-c2cc3c(-c4ccccc4)n(-c4ccccc4)c(-c4ccccc4)c3cc2-c2cc(C)cc(C)c2)c1]
32
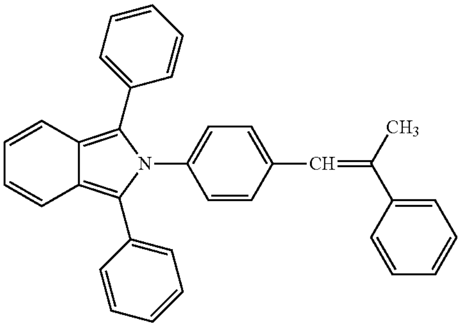 [SMILES: CC(=Cc1ccc(-n2c(-c3ccccc3)c3ccccc3c2-c2ccccc2)cc1)c1ccccc1]

TABLE 1-8

33

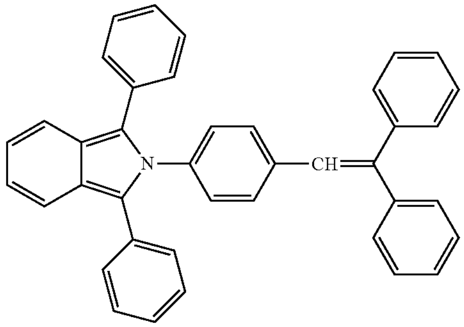 [SMILES: C(=C(c1ccccc1)c1ccccc1)c1ccc(-n2c(-c3ccccc3)c3ccccc3c2-c2ccccc2)cc1]

34

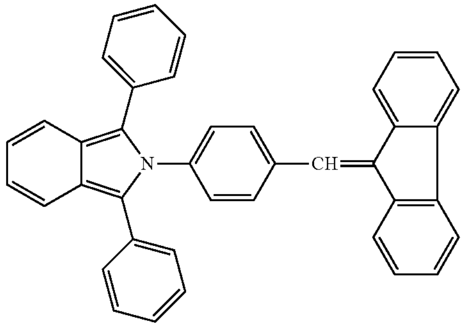 [SMILES: C(=C1c2ccccc2-c2ccccc21)c1ccc(-n2c(-c3ccccc3)c3ccccc3c2-c2ccccc2)cc1]

35

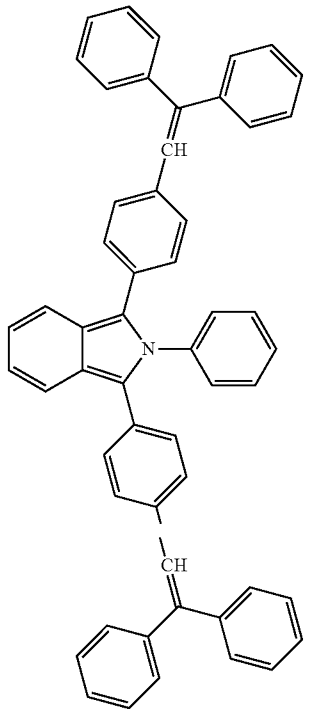

TABLE 1-9

36

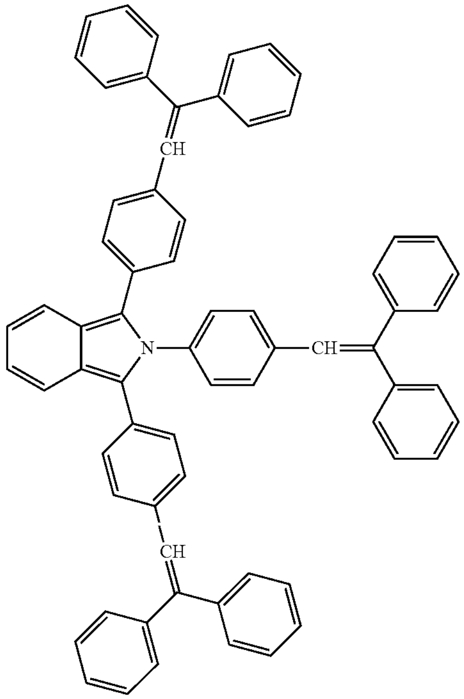 [SMILES: C(=C(c1ccccc1)c1ccccc1)c1ccc(-c2c3ccccc3c(-c3ccc(C=C(c4ccccc4)c4ccccc4)cc3)n2-c2ccc(C=C(c3ccccc3)c3ccccc3)cc2)cc1]

Next, layer compositions of the electrophotographic photoreceptor of the present invention are explained.

FIG. 1 is a schematic view illustrating a cross section of a surface of an embodiment of the photoreceptor of the present invention, in which a photosensitive layer 33 including a CGM and a CTM as the main components is formed on an electroconductive substrate 31.

Figure 2:
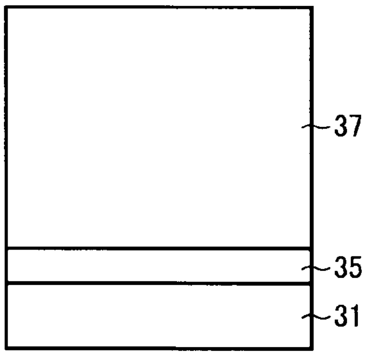
FIG. 2 is a cross-sectional view of another embodiment of the photosensitive layer of the electrophotographic photoreceptor of the present invention.

In FIG. 2, a CGL 35 including a CGM as the main component overlies a CTL 37 including a CTM as the main component on an electroconductive substrate 31.

Figure 3:
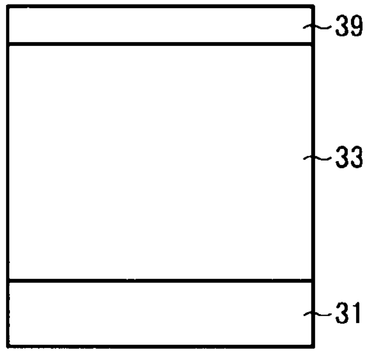
FIG. 3 is a cross-sectional view of a further embodiment of the photosensitive layer of the electrophotographic photoreceptor of the present invention.

In FIG. 3, a photosensitive layer 33 including a CGM and a CTM as the main components is formed on an electroconductive substrate 31, and further a protection layer 39 is formed on a surface of the photosensitive layer. In this case, the protection layer 39 may include the isoindole derivative of the present invention.

Figure 4:
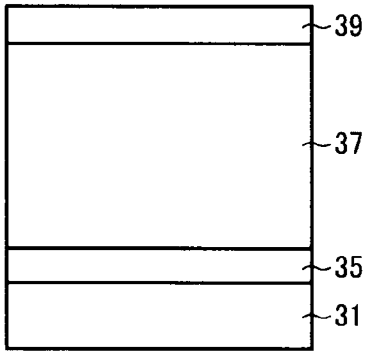
FIG. 4 is a cross-sectional view of another embodiment of the photosensitive layer of the electrophotographic photoreceptor of the present invention.

In FIG. 4, a CGL 35 including a CGM as the main component, a CTL 37 including a CTM as the main component overlying the CGL, and further a protection layer 39 overlying the CTL are formed on an electroconductive substrate 31. In this case, the protection layer 39 may include the isoindole derivative of the present invention.

Figure 5:
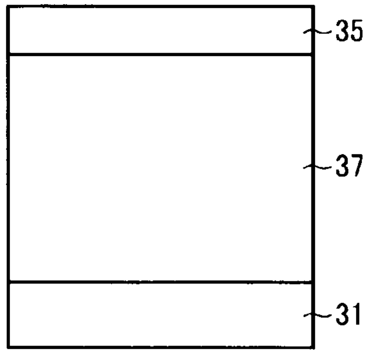
FIG. 5 is a cross-sectional view of a further embodiment of the photosensitive layer of the electrophotographic photoreceptor of the present invention.

In FIG. 5, a CTL 37 including a CTM as the main component, a CGL 35 including a CGM as the main component overlying the CTL are formed on an electroconductive substrate 31.

Figure 6:
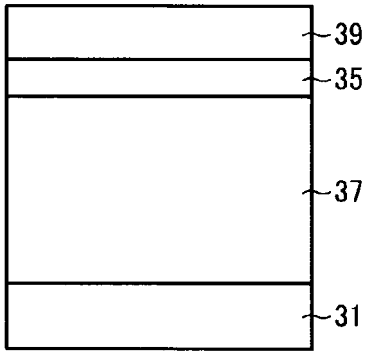
FIG. 6 is a cross-sectional view of another embodiment of the photosensitive layer of the electrophotographic photoreceptor of the present invention.

In FIG. 6, a CTL 37 including a CTM as the main component, a CGL 35 including a CGM as the main component overlying the CTL, and further a protection layer 39 overlying the CGL are formed on an electroconductive substrate 31. In this case, the protection layer 39 may include the isoindole derivative of the present invention.

Suitable materials for use as the electroconductive substrate 31 include materials having a volume resistance not greater than $10^{10}$ Ω·cm. Specific examples of such materials include plastic cylinders, plastic films or paper sheets, on the surface of which a metal such as aluminum, nickel, chromium, nichrome, copper, gold, silver, platinum and the like, or a metal oxide such as tin oxides, indium oxides and the like, is deposited or sputtered. In addition, a plate of a metal such as aluminum, aluminum alloys, nickel and stainless steel and a metal cylinder, which is prepared by tubing a metal such as the metals mentioned above by a method such as impact ironing or direct ironing, and then treating the surface of the tube by cutting, super finishing, polishing and the like treatments, can be also used as the substrate. Further, endless belts of a metal such as nickel and stainless steel, which have been disclosed in Japanese published unexamined application No. 52-36016, can be also used as the electroconductive substrate 31.

Furthermore, substrates, in which a coating liquid including a binder resin and an electroconductive powder is coated on the supporters mentioned above, can be used as the substrate 31. Specific examples of such an electroconductive powder include carbon black, acetylene black, powders of metals such as aluminum, nickel, iron, Nichrome, copper, zinc, silver and the like, and metal oxides such as electroconductive tin oxides, ITO and the like. Specific examples of the binder resin include known thermoplastic resins, thermosetting resins and photo-crosslinking resins, such as polystyrene, styrene-acrylonitrile copolymers, styrene-butadiene copolymers, styrene-maleic anhydride copolymers, polyesters, polyvinyl chloride, vinyl chloride-vinyl acetate copolymers, polyvinyl acetate, polyvinylidene chloride, polyarylates, phenoxy resins, polycarbonates, cellulose acetate resins, ethyl cellulose resins, polyvinyl butyral resins, polyvinyl formal resins, polyvinyl toluene, poly-N-vinyl carbazole, acrylic resins, silicone resins, epoxy resins, melamine resins, urethane resins, phenolic resins, alkyd resins and the like resins. Such an electroconductive layer can be formed by coating a coating liquid in which an electroconductive powder and a binder resin are dispersed in a solvent such as tetrahydrofuran, dichloromethane, methyl ethyl ketone, toluene and the like solvent, and then drying the coated liquid.

In addition, substrates, in which an electroconductive resin film is formed on a surface of a cylindrical substrate using a heat-shrinkable resin tube which is made of a combination of a resin such as polyvinyl chloride, polypropylene, polyesters, polyvinylidene chloride, polyethylene, chlorinated rubber and fluorine-containing resins, with an electroconductive material, can be also used as the substrate 31.

Next, the photosensitive layer of the present invention is explained. In the present invention, the photosensitive layer may be single-layered or a multi-layered. At first, the multi-layered photosensitive layer including the CGL 35 and the CTL 37 is explained for explanation convenience.

The CGL 35 is a layer including a CGM as the main component. Known CGMs can be used in the CGL 35. Specific examples of the CGM include azo pigments such as CI Pigment Blue 25 (color index CI-21180), CI Pigment Red 41 (CI-21200), CI Acid Red 52 (CI 45100), CI Basic Red 3 (CI 45210), an azo pigment having a carbazole skeleton disclosed in Japanese published unexamined application (JPUA) No. 53-95033, an azo pigment having a distyrylbenzene skeleton disclosed in JPUA No. 53-133445, an azo pigment having a triphenylamine skeleton disclosed in JPUA No. 53-132347, an azo pigment having a dibenzothiophene skeleton disclosed in JPUA No. 54-21728, an azo pigment having an oxadiazole skeleton disclosed in JPUA No. 54-12742, an azo pigment having a fluorenone skeleton disclosed in JPUA No. 54-22834, an azo pigment having a bisstilbene skeleton disclosed in JPUA No. 54-17733, an azo pigment having a distyryloxadiazole skeleton disclosed in JPUA No. 54-2129, an azo pigment having a distyrylcarbazole skeleton disclosed in JPUA No. 54-14967 and an azo pigment having a benzanthrone skeleton; phthalocyanine pigments such as CI Pigment Blue 16 (CI 74100), Y-type oxotitaniumphthalocyanine disclosed in JPUA No. 64-17066, A(β)-type oxotitaniumphthalocyanine, B(α)-type-type oxotitaniumphthalocyanine, 1-type oxotitaniumphthalocyanine disclosed in JPUA No. 11-21466, II-type chlorogalliumphthalocyanine disclosed by Mr. Iijima and others in the 67$^{th}$ spring edition 1B4, 04 published by Chemical Society of Japan in 1994, V-type hydroxygalliumphthalocyanine disclosed Mr. Daimon and others in the 67$^{th}$ spring edition 1B4, 05 published by Chemical Society of Japan in 1994 and X-type metal-free phthalocyanine disclosed in U.S. Pat. No. 3,816,118; indigo pigments such as CI Vat Brown 5 (CI 73410) and CI Vat Dye (CI 73030); and perylene pigments such as Algo Scarlet B from Bayer AG and Indanthrene Scarlet R from Bayer AG. These materials can be used alone or in combination.

The CGL 35 can be prepared by dispersing a CGM in a proper solvent optionally together with a binder resin using a ball mill, an attritor, a sand mill or a supersonic dispersing machine, coating the coating liquid on an electroconductive substrate and then drying the coated liquid.

Specific example of the binder resins optionally used in the CGL 35, include polyamides, polyurethanes, epoxy resins, polyketones, polycarbonates, silicone resins, acrylic resins, polyvinyl butyral, polyvinyl formal, polyvinyl ketones, polystyrene, polysulfone, poly-N-vinylcarbazole, polyacrylamide, polyvinyl benzal, polyesters, phenoxy resins, vinyl chloride-vinyl acetate copolymers, polyvinyl acetate, polyphenylene oxide, polyamides, polyvinyl pyridine, cellulose resins, casein, polyvinyl alcohol, polyvinyl pyrrolidone, and the like resins. The content of the binder resin in the CGL 35 is preferably from 0 to 500 parts by weight, and preferably from 10 to 300 parts by weight, per 100 parts by weight of the CGM. The binder resin can be included either before or after dispersion of the CGM in the solvent.

Specific examples of the solvent include isopropanol, acetone, methyl ethyl ketone, cyclohexanone, tetrahydrofuran, dioxane, ethyl cellosolve, ethyl acetate, methyl acetate, dichloromethane, dichloroethane, monochlorobenzene, cyclohexane, toluene, xylene, ligroin, and the like solvents. In particular, ketone type solvents, ester type solvents and ether type solvents are preferably used. These can be used alone or in combination.

The CGL 35 includes a CGM, a solvent and a binder rein as the main components. Any additives such as a sensitizer, a disperser, a detergent and a silicone oil can be included therein.

The coating liquid can be coated by a coating method such as dip coating, spray coating, bead coating, nozzle coating, spinner coating and ring coating. The CGL 35 preferably has a thickness of from 0.01 to 5 μm, and more preferably from 0.1 to 2 μm.

The CTL 37 is a layer including a CTM as the main component. Hereinafter, the CTM is explained. The CTM is classified to a positive-hole transport material, an electron transport material and a polymeric charge transport material.

Specific examples of the positive-hole transport material include poly-N-carbazole and its derivatives, poly-γ-carbazolylethylglutamate and its derivatives, pyrene-formaldehyde condensation products and their derivatives, polyvinyl pyrene, polyvinyl phenanthrene, polysilane, oxazole derivatives, oxadiazole derivatives, imidazole derivatives, triphenylamine derivatives and compounds having the following formulae (I) to (XXX).

(I)

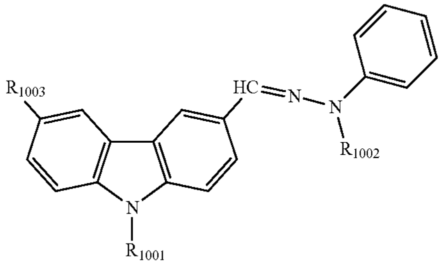

wherein $R_{1001}$ represents a methyl group, an ethyl group, a 2-hydroxyethyl group or a 2-chlorethyl group; $R_{1002}$ represents a methyl group, an ethyl group, a benzyl group or a phenyl group; and $R_{1003}$ represents a hydrogen atom, a chlorine atom, a bromine atom, an alkyl group having 1 to 4 carbon atoms, an alkoxy group having 1 to 4 carbon atoms, a dialkylamino group or a nitro group.

Specific examples of the compound having formula (I) include 9-ethylcalbazole-3-aldehyde-1-methyl-1-phenylhydrazone, 9-ethylcalbazole-3-aldehyde-1-benzyl-1-phenylhydrazone, 9-ethylcalbazole-3-aldehyde-1,1-diphenylhydrazone, etc.

(II)

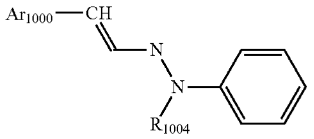

wherein $Ar_{1000}$ represents a naphthalene ring, an anthracene ring, a pyrene ring and their substituents, a pyridine ring, a furan ring or thiophene ring; and $R_{1004}$ represents an alkyl group, a phenyl group or a benzyl group.

Specific examples of the compound having formula (II) include 4-diethylaminostyryl-β-aldehhyde-1-methyl-1-phenylhydrazone, 4-methoxynaphthalene-1-aldehyde-1-benzyl-1-phenylhydrazone, etc.

(III)

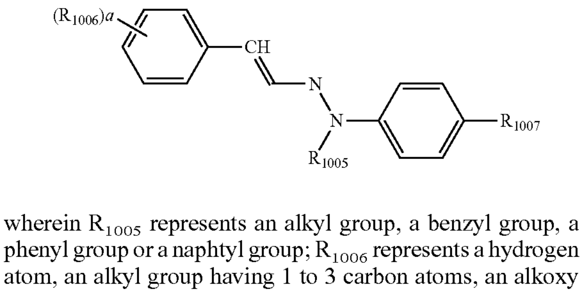

wherein $R_{1005}$ represents an alkyl group, a benzyl group, a phenyl group or a naphtyl group; $R_{1006}$ represents a hydrogen atom, an alkyl group having 1 to 3 carbon atoms, an alkoxy group having 1 to 3 carbon atoms, a dialkylamino group, diaralkylamino group or a diarylamino group; n represents an integer of from 1 to 4 and $R_{1006}$ may be the same or different from each other when n is not less than 2; and $R_{1007}$ represents a hydrogen atom or a methoxy group.

Specific examples of the compound having formula (III) include 4-methoxybenzaldehyde-1-methyl-1-phenylhydrazone, 2,4-dimethoxybenzaldehyde-1-benzyl-1-phenylhydrazone, 4-diethylaminobenzaldehyde-1,1-diphenylhydrazone, 4-methoxybenzaldehyde-1-(4-methoxy)phenylhydrazone, 4-diphenylaminobenzaldehyde-1-benzyl-1-phenylhydrazone, 4-dibenzylaminobenzaldehyde-1,1-diphenylhydrazone, etc.

(IV)

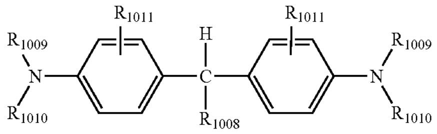

wherein $R_{1008}$ represents an alkyl group having 1 to 11 carbon atoms, a substituted or unsubstituted phenyl group or a heterocyclic ring group; each of $R_{1009}$ and $R_{1010}$ represents a hydrogen atom, an alkyl group having 1 to 4 carbon atoms, a hydroxyalkyl group, a chloralkyl group or a substituted or unsubstituted aralkyl group, and may be combined each other to form a heterocyclic ring group including a nitrogen atom; and $R_{1011}$ represents a hydrogen atom, an alkyl group having 1 to 4 carbon atoms, an alkoxy group or a halogen atom.

Specific examples of the compound having the formula (IV) include 1,1-bis(4-dibenzylaminophenyl)propane, tris(4-diethylaminophenyl)methane, 1,1-bis(4-dibenzylaminophenyl)propane, 2,2'-dimethyl-4,4'-bis(diethylamino)-triphenylmethane, etc.

(V)

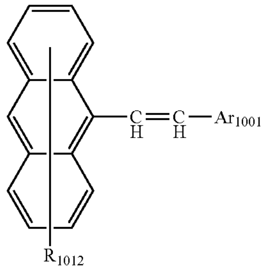

wherein $R_{1012}$ represents a hydrogen atom or a halogen atom; and $Ar_{1001}$ represents a substituted or unsubstituted phenyl group, a naphtyl group, an anthryl group or a carbazolyl group.

Specific examples of the compound having the formula (V) include 9-(4-diethylaminostyryl)anthracene, 9-bromo-10-(4-diethylaminostyryl)anthracene, etc.

(VI)

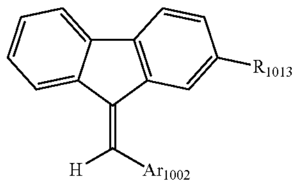

wherein $R_{1013}$ represents a hydrogen atom, a cyano group, an alkoxy group having 1 to 4 carbon atoms or a alkyl group having 1 to 4 carbon atoms; and $Ar_{1002}$ represents a group having the following formulae (VII) or (VIII):

(VII)

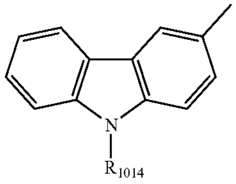

(VIII)

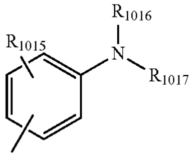

wherein $R_{1014}$ represents an alkyl group having 1 to 4 carbon atoms; $R_{1015}$ represents a hydrogen atom, a halogen atom, an alkyl group having 1 to 4 carbon atoms, an alkoxy group having 1 to 4 carbon atoms or a dialkylamino group; n is 1 or 2, and $R_{1015}$ may be the same or different from each other when n is 2; and $R_{1016}$ and $R_{1017}$ represent a hydrogen atom, a substituted or unsubstituted alkyl group having 1 to 4 carbon atoms or a substituted or unsubstituted benzyl group.

Specific examples of the compound having the formula (VI) include 9-(4-dimethylaminobenzylidene)fluorene, 3-(9-fluorenylidene)-9-ethylcarbazole, etc.

(IX)

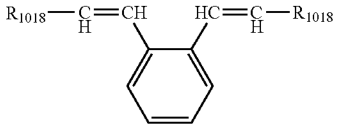

wherein $R_{1018}$ represents a carbazolyl group, a pyridyl group, a thienyl group, an indolyl group, a furyl group, a substituted or unsubstituted phenyl, styryl, naphtyl group or an anthryl group, and their substituents are selected from the group consisting of a dialkylamino group, an alkyl group, an alkoxy group, a carboxyl group or its ester, a halogen atom, a cyano group, an aralkylamino group, N-alkyl-N-aralkylamino group, an amino group, a nitro group and an acethylamino group.

Specific examples of the compound having the formula (IX) include 1,2-bis-(4-diethylaminostyryl)benzene, 1,2-bis (2-,4-dimethoxystyryl)benzene, etc.

(X)

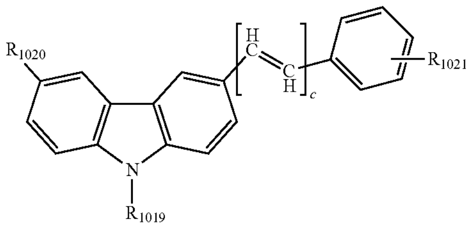

wherein $R_{1019}$ represents a lower alkyl group, a substituted or unsubstituted phenyl group or a benzyl group; $R_{1020}$ and $R_{1021}$ represent a hydrogen atom, a lower alkyl group, a lower alkoxy group, a halogen atom, a nitro group, an amino group or an amino group substituted by a lower alkyl group or a benzyl group; and n is 1 or 2.

Specific examples of the compound having the formula (X) include 3-styryl-9-ethylcarbazole, 3-(4-methoxystyryl)-9-ethylcarbazole, etc.

(XI)

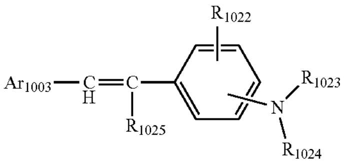

wherein $R_{1022}$ represents a hydrogen atom, an alkyl group, an alkoxy group or a halogen atom; $R_{1023}$ and $R_{1024}$ represent a substituted or unsubstituted aryl group; $R_{1025}$ represents a hydrogen atom, a lower alkyl group or a substituted or unsubstituted phenyl group; and Ar represents a substituted or unsubstituted phenyl group or a naphtyl group.

Specific examples of the compound having the formula (XI) include 4-diphenylaminostilbene, 4-dibenzylaminostilbene, 4-ditolylaminostilbene, 1-(4-iphenylaminostyryl) naphthalene, 1-(4-diethylaminostyryl)naphthalene, etc.

(XII)

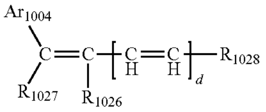

wherein d is 0 or 1; $R_{1026}$ represents a hydrogen atom, an alkyl group or a substituted or unsubstituted phenyl group; $Ar_{1004}$ represents a substituted or unsubstituted aryl group; $R_{1027}$ represents an alkyl group having 1 to 4 carbon atoms or a substituted or unsubstituted aryl group; and $Ar_{1028}$ represents a 9-anthryl group, a substituted or unsubstituted carbazolyl group or a group having the following formula (XIII) or (XIV):

(XIII)

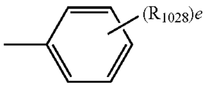

(XIV)

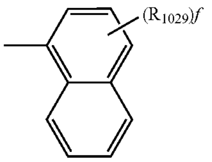

wherein each of $R_{1028}$ and $R_{1029}$ represents a hydrogen atom, an alkyl group, an alkoxy group, a halogen atom or a group having the following formula (XV); and each of e and f represents an integer of from 1 to 3;

(XV)

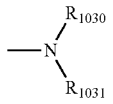

wherein $R_{1030}$ and $R_{1031}$ represent a substituted or unsubstituted aryl group, and $R_{1031}$ may form a ring, and wherein $R_{1030}$ and $R_{1031}$ may be the same or different from each other when e and f are not less than 2, and $R_{1028}$ and $R_{1026}$ may form a ring together when d is 0.

Specific examples of the compound having the formula (XII) include 4'-diphenylamino-α-phenylstilbene, 4'-bis(4-methylphenyl)amino-α-phenylstilbene, etc.

(XVI)

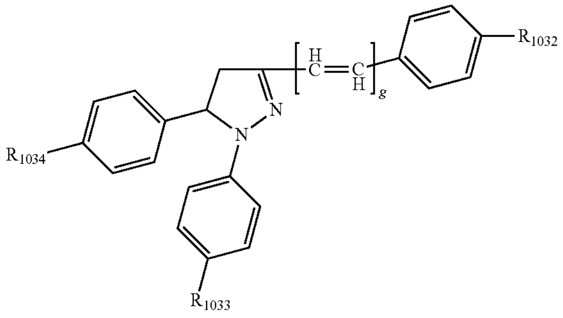

wherein $R_{1032}$, $R_{1033}$ and $R_{1034}$ represent a hydrogen atom, a lower alkyl group, a lower alkoxy group, a halogen atom or a dialkylamino group; and n is 0 or 1.

Specific examples of the compound having the formula (XVI) include 1-phenyl-3-(4-diethylaminostyryl)-5-(4-diethylaminophenyl)pyrazoline, etc.

(XVII)

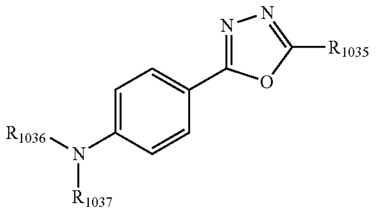

wherein $R_{1036}$ and $R_{1037}$ represent an alkyl group including a substituted alkyl group or a substituted or unsubstituted aryl group; and $R_{1035}$ represents a substituted amino group, a substituted or unsubstituted aryl group or an aryl group.

Specific examples of the compound having the formula (XVII) include 2,5-bis(4-diethylaminophenyl)-1,3,4-oxadiazole, 2-N,N-diphenylamino-5-(4-diethylaminophenyl)-1,3,4-oxadiazole, 2-(4-dimethylaminophenyl)-5-(4-diethylaminophenyl)-1,3,4-oxadiazole, etc.

(XIX)

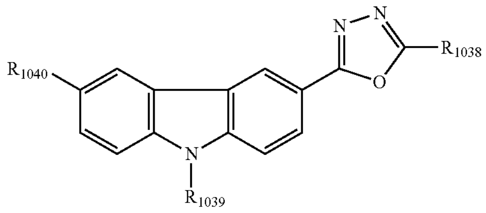

wherein $R_{1040}$ represents a hydrogen atom, a lower alkyl group or a halogen atom; $R_{1039}$ represents an alkyl group including a substituted alkyl group or a substituted or unsubstituted aryl group; and $R_{1038}$ represents a substituted amino group, a substituted or unsubstituted aryl group or an aryl group.

Specific examples of the compound having the formula (XIX) include 2-N,N-diphenylamino-5-(N-ethylcarbazole-3-yl)-1,3,4-oxadiazole, 2-(4-diethylaminophenyl)-5-(N-ethylcarbazole-3-yl)-1,3,4-oxadiazole, etc.

(XX)

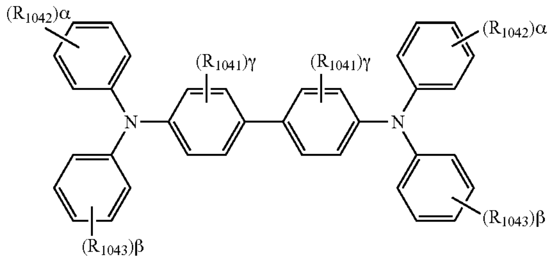

wherein $R_{1041}$ represents a lower alkyl group, a lower alkoxy group or a halogen atom; each of $R_{1042}$ and $R_{1043}$ represents a hydrogen atom, a lower alkyl group, a lower alkoxy group or a halogen atom; and each of α, β and γ represents 0 or an integer of from 1 to 4.

Specific examples of the benzidine compound having the formula (XX) include N,N'-diphenyl-N,N'-bis(3-methylphenyl)-[1,1'-biphenyl]-4,4'-diamine, 3,3'-dimethyl-N,N,N',N'-tetrakis(4-methylphenyl)-[1,1'-biphenyl]-4,4'-diamine, etc.

(XXI)

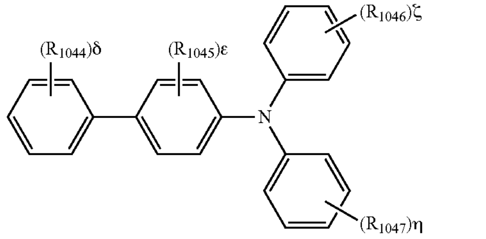

wherein $R_{1044}$, $R_{1046}$ and $R_{1047}$ represent a hydrogen atom, an amino group, an alkoxy group, a thioalkoxy group, an aryloxy group, a methylenedioxy group, a substituted or unsubstituted alkyl group, a halogen atom or a substituted or unsubstituted aryl group; $R_{1045}$ represents a hydrogen atom, an alkoxy group, a substituted or unsubstituted alkyl group or a halogen atom, but a case in which $R_{1044}$, $R_{1046}$, $R_{1045}$ and $R_{1047}$ are all hydrogen atoms is excluded; and each of δ, ε, ξ and η an integer of from 1 to 4, and $R_{1044}$, $R_{1046}$, $R_{1045}$ and $R_{1047}$ may be the same or different from the others when δ, ϵ, ξ and η are an integer of from 2 to 4.

Specific examples of the biphenylamine compound having the formula (XXI) include 4'-methoxy-N,N-diphenyl-[1,1'-biphenyl]-4-amine, 4'-methyl-N,N-bis(4-methylphenyl)-[1,1'-biphenyl]-4-amine, 4'-methoxy-N,N-bis(4-methylphenyl)-[1,1'-biphenyl]-4-amine, N,N-bis(3,4-dimethylphenyl)-[1,1'-biphenyl]-4-amine, etc.

(XXII)

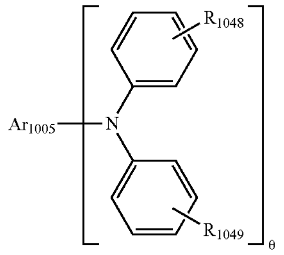

wherein $Ar_{1005}$ represents a condensation polycyclic hydrocarbon group having 18 or less carbon atoms which can have a substituent; and each of $R_{1048}$ and $R_{1049}$ represents a hydrogen atom, a halogen atom, a substituted or unsubstituted alkyl group, an alkoxy group, or a substituted or unsubstituted phenyl group and θ is 1 or 2.

Specific examples of the triarylamine compound having the formula (XXII) include N,N-diphenyl-pyrene-1-amine, N,N-di-p-tolyl-pyrne-1-amine, N,N-di-p-tolyl-1-naphthylamine, N,N-di(p-tolyl)-1-phenanthorylamine, 9,9-dimethyl-2-(di-p-tolylamino)fluorene, N,N,N',N'-tetrakis(4-methylphenyl)-phenanthrene-9,10-diamine, N,N,N',N'-tetrakis(3-methylphenyl)-m-phenylenediamine, etc.

(XXIII)

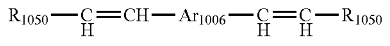

wherein $Ar_{1006}$ represents a substituted or unsubstituted aromatic hydrocarbon group; and $R_{1050}$ represents the following formula (XXIV):

(XXIV)

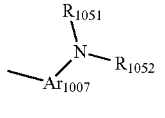

wherein $Ar_{1007}$ represents a substituted or unsubstituted aromatic hydrocarbon group; and $R_{1051}$ and $R_{1052}$ represent substituted or unsubstituted alkyl group or a substituted or unsubstituted aryl group.

Specific examples of the diolefin aromatic compound having the formula (XXIV) include 1,4-bis(4-diphenylaminostyryl)benzene, 1,4-bis[4-di(p-toly)aminostyryl]benzene, etc.

(XXV)

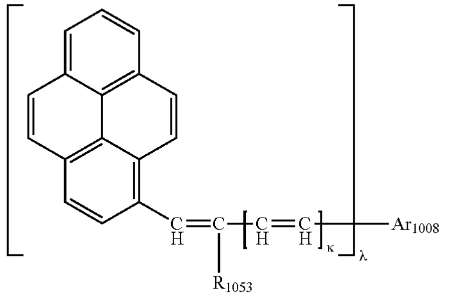

wherein $Ar_{1008}$ represents a substituted or unsubstituted aromatic hydrocarbon group; $R_{1053}$ represents a hydrogen atom, a substituted or unsubstituted alkyl group or a substituted or unsubstituted aryl group; κ is 0 or 1; λ is 1 or 2; and $Ar_{1008}$ and $R_{1053}$ may form a ring when κ is 0 and λ is 1.

Specific examples of the styrylpyrene compound having the formula (XXV) include 1-(4-diphenylaminostyryl)pyrene, 1-[4-di(p-toly)aminostyryl]pyrene, etc.

Specific examples of an electron transport materials include chloranil, bromoanil, tetracyanoethylene, tetracyanoquinodimethane, 2,4,7-trinitro-9-fluorenone, 2,4,5,7-tetranitro-9-fluorenone, 2,4,5,7-tetranitroxanthone, 2,4,8-trinitrothioxanthone, 2,6,8-trinitro-indeno[1,2-b]thiophene-4-one, and 1,3,7-trinitrodibenzothiophene-5,5-dioxide, etc. In addition, electron transport materials having the following formulae (XXVI) to (XXX) are preferably used. These can be used alone or in combination (XXVI)

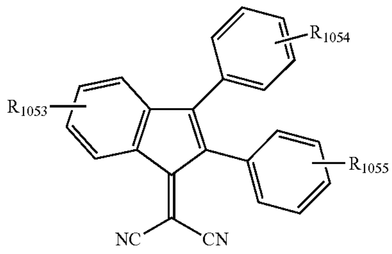

wherein each of $R_{1053}$, $R_{1054}$ and $R_{1055}$ represents a hydrogen atom, a halogen atom, a substituted or unsubstituted alkyl group, an alkoxy group or a substituted or unsubstituted phenyl group.

(XXVII)

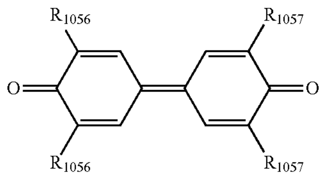

wherein each of $R_{1056}$ and $R_{1057}$ represents a hydrogen atom, a substituted or unsubstituted alkyl group, or a substituted or unsubstituted phenyl group.

(XXVIII)

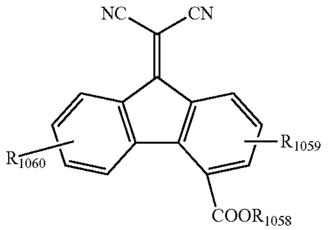

wherein each of $R_{1058}$, $R_{1059}$ and $R_{1060}$ represents a hydrogen atom, a halogen atom, a substituted or unsubstituted alkyl group, an alkoxy group or a substituted or unsubstituted phenyl group.

(XXIX)

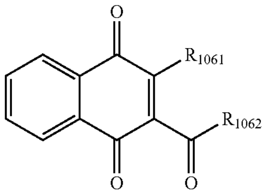

wherein $R_{1061}$ represents an alkyl group or an aryl group optionally having a substituted group; and $R_{1062}$ represents an alkyl group or an aryl group optionally having a substituted group, or a group having the following formula (XXX):

$O—R_{1063}$ (XXX)

wherein $R_{1063}$ represents an alkyl group or an aryl group optionally having a substituted group.

Specific examples of the binder resin include thermoplastic resins or thermosetting resins such as polystyrene, styrene-acrylonitrile copolymers, styrene-butadiene copolymers, styrene-maleic anhydride copolymers, polyesters, polyvinyl chloride, vinyl chloride-vinyl acetate copolymers, polyvinyl acetate, polyvinylidene chloride, polyarylates, phenoxy resins, polycarbonates, cellulose acetate resins, ethyl cellulose resins, polyvinyl butyral resins, polyvinyl formal resins, polyvinyl toluene, poly-N-vinyl carbazole, acrylic resins, silicone resins, epoxy resins, melamine resins, urethane resins, phenolic resins, alkyd resins and the like.

When a CTM and the isoindole derivative of the present invention are included in a CTL, a total content thereof is preferably from 20 to 300 parts by weight, and more preferably from 40 to 150 parts by weight per 100 parts by weight of a binder resin. The CTL preferably has a thickness not greater than 25 μm in view of resolution of the resultant images and response. The lower limit of the thickness is preferably not less than 5 μm, although it depends on the image forming system (particularly on a charged potential of the electrophotographic photoreceptor).

In addition, the content of the isoindole derivative of the present invention is preferably from 0.01 to 150% by weight based on total weight of the CTM. When less than 0.01% by weight, the durability against the oxidizing gas of the resultant photoreceptor deteriorates. When greater than 150% by weight, the residual potential thereof increases.

Specific examples of a solvent for use in forming the CTL include tetrahydrofuran, dioxane, toluene, dichloromethane, monochlorobenzene, dichloroethane, cyclohexanone, methyl ethyl ketone, acetone and the like solvents. The CTM can be used alone or in combination in the solvent.

As an antioxidant preferably included in the CTL, conventional antioxidants can be used, and (c) hydroquinone compounds and (f) hindered amine compounds are effectively used in particular.

However, the antioxidant for use in the CTL has a different purpose from the after-mentioned purpose, and are used to prevent quality alteration of the isoindole derivative of the present invention Therefore, the antioxidant is preferably included in a CTL coating liquid before the isoindole derivative of the present invention is included therein. The content of the antioxidant is from 0.1 to 200% by weight based on total weight of the isoindole derivative.

The CTL preferably includes a polymeric CTM, which has both a binder resin function and a charge transport function as well, because the resultant CTL has good abrasion resistance. Suitable charge transport polymer materials include known materials. Among these materials, polycarbonate resins having a triarylamine structure in their main chain and/or side chain are preferably used. Specific examples of the polymeric CTM include compounds having the following formulae (A) to (M):

(A)

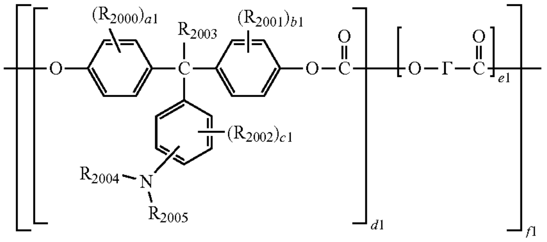

Wherein each of $R_{2000}$, $R_{2001}$ and $R_{2002}$ represents a substituted or unsubstituted alkyl group, or a halogen atom; $R_{2003}$ represents a hydrogen atom, or a substituted or unsubstituted alkyl group; $R_{2004}$ and $R_{2005}$ represent a substituted or unsubstituted aryl group; al, each of b1 and c1 represents 0 or an integer of from 1 to 4; d1 is a number of from 0.1 to 1.0 and e1 is a number of from 0 to 0.9; f1 represents a repeating number and is an integer of from 5 to 5000; and X represents a divalent aliphatic group, a divalent alicyclic group or a divalent group having the following formula (B):

(B)

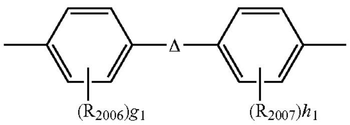

wherein each of $R_{2006}$ and $R_{2007}$ represents a substituted or unsubstituted alkyl group, a substituted or unsubstituted aryl group, or a halogen atom; each of g1 and h1 represents 0 or an integer of from 1 to 4; d is 0 or 1; and A represents a single bond, a linear alkylene group, a branched alkylene group, a cyclic alkylene group, —O—, —S—, —SO—, —$SO_2$—, —CO—, —CO—O—Z—O—CO— (Z represents a divalent aliphatic group), or a group having the following formula (C):

(C)

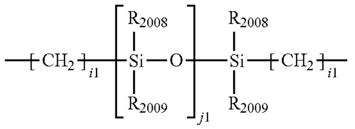

wherein i1 is an integer of from 1 to 20; j1 is an integer of from 1 to 2,000; and each of $R_{2008}$ and $R_{2009}$ represents a substituted or unsubstituted alkyl group, or a substituted or unsubstituted aryl group, and wherein $R_{2006}$, $R_{2007}$, $R_{2008}$ and $R_{2009}$ may be the same or different from the others.

(D)

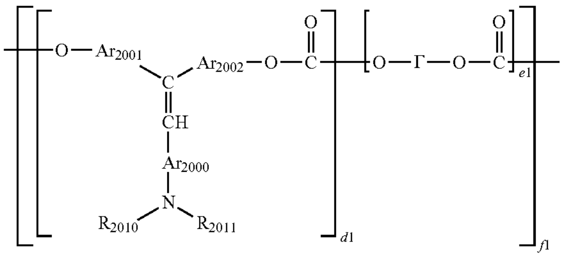

wherein $R_{2010}$ and $R_{2011}$ represent a substituted or unsubstituted aryl group; $Ar_{2000}$, $Ar_{2001}$ and $Ar_{2002}$ represent an arylene group; and Γ, d1, e1 and f1 are same in the formula (A).

(E)

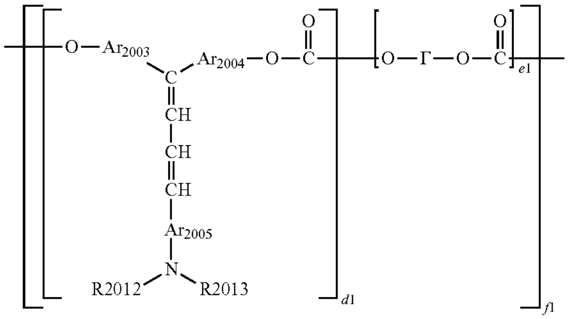

wherein R2012 and R2013 represent a substituted or unsubstituted aryl group; $Ar_{2003}$, $Ar_{2004}$ and $Ar_{2005}$ represent an arylene group; and Γ, d1, e1 and f1 are the same in formula (A).

(F)

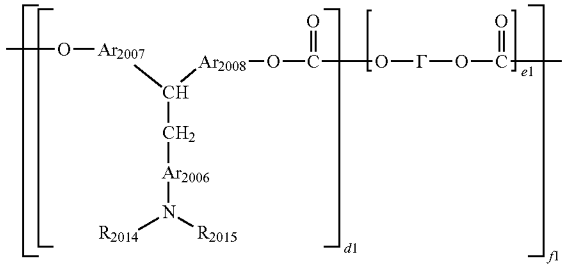

wherein $R_{2014}$ and $R_{2015}$ represent a substituted or unsubstituted aryl group; $Ar_{2006}$, $Ar_{2007}$ and $Ar_{2008}$ represent an arylene group; and Γ, d1, e1 and f1 are the same in formula (A).

(G)

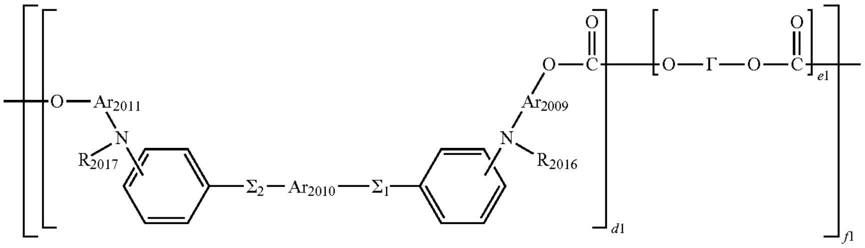

wherein, $R_{2016}$ and $R_{2017}$ represent a substituted or unsubstituted aryl group; $Ar_{2009}$, $Ar_{2010}$ and $Ar_{2011}$ represent an arylene group; $\Sigma_1$ and $\Sigma_2$ represent a substituted or unsubstituted ethylene group, or a substituted or unsubstituted vinylene group; and Γ, d1, e1 and f1 are the same in formula (A).

(H)

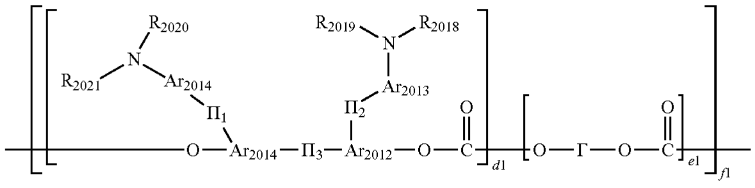

wherein, $R_{2018}$, $R_{2019}$, $R_{2020}$ and $R_{2021}$ represent a substituted or unsubstituted aryl group; $Ar_{2012}$, $Ar_{2013}$, $Ar_{2014}$ and $Ar_{2015}$ represent an arylene group; each of $\Pi_1$, $\Pi_2$ and $\Pi_3$ represents a single bond, a substituted or unsubstituted alkylene group, a substituted or unsubstituted cycloalkylene group, a substituted or unsubstituted alkyleneether group, an oxygen atom, a sulfur atom, or a vinylene group; and Γ, d1, e1 and f1 are the same in formula (A).

(I)

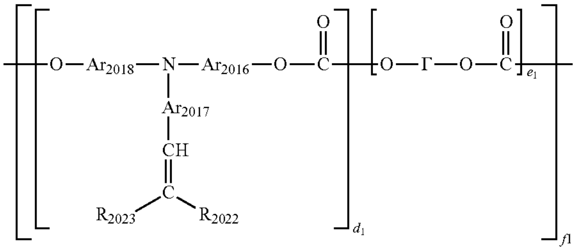

wherein, each of $R_{2022}$ and $R_{2033}$ represents a hydrogen atom, or substituted or unsubstituted aryl group, and $R_{2022}$ and $R_{2033}$ may form a ring; $Ar_{2016}$, $Ar_{2017}$ and $Ar_{2018}$ represents an arylene group; and Γ, d1, e1 and f1 are the same in formula (A).

(J)

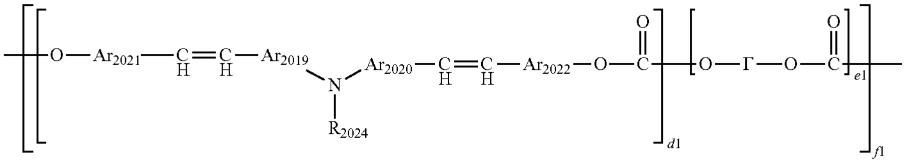

wherein, $R_{2024}$ represents a substituted or unsubstituted aryl group; $Ar_{2019}$, $Ar_{2020}$, $Ar_{2021}$ and $Ar_{2022}$ represents an arylene group; and Γ, d1, e1 and f1 are the same in formula (A).

(K)

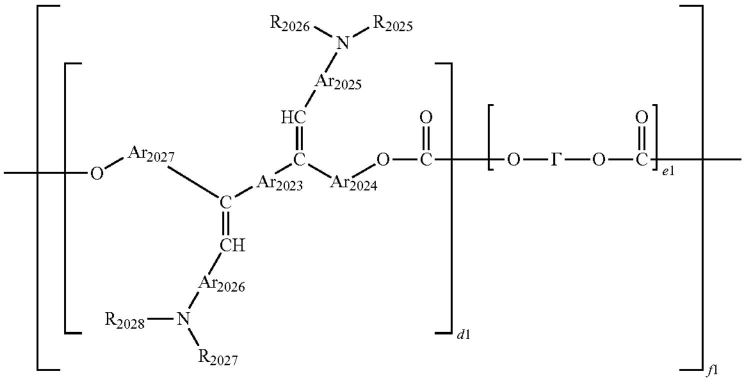

wherein, $R_{2025}$, $R_{2026}$, $R_{2027}$ and $R_{2028}$ represent a substituted or unsubstituted aryl group; $Ar_{2024}$, $Ar_{2025}$, $Ar_{2026}$, $Ar_{2027}$ and $Ar_{28}$ represent an arylene group; and Γ, d1, e1 and f1 are the same in formula (A).

(L)

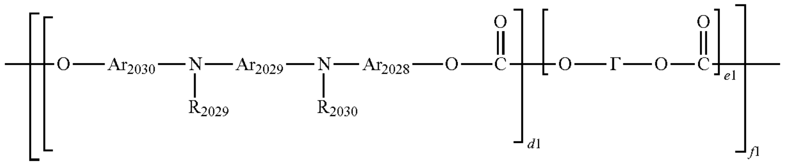

wherein, $R_{2029}$ and $R_{2030}$ represent a substituted or unsubstituted aryl group; $Ar_{2028}$, $Ar_{2029}$ and $Ar_{2030}$ represent an arylene group; and Γ, d1, e1 and f1 are the same in formula (A).

(M)

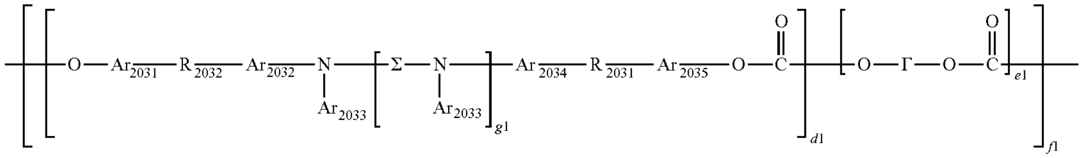

wherein $Ar_{2031}$, $Ar_{2032}$, $Ar_{2033}$, $Ar_{2034}$ and $Ar_{2034}$ represent a substituted or unsubstituted aromatic ring group; Σ represents an aromatic ring group or —$Ar_{2036}$-Za-$Ar_{2036}$—; $Ar_{2036}$ represents a substituted or unsubstituted aromatic ring group; Za represents O, S or an alkylene group; $R_{2031}$ and $R_{2032}$ represent a linear alkylene group or a branched alkylene group; m is 0 or 1; and Γ, d1, e1 and f1 are the same in formula (A).

The CTL 37 can be formed by coating a coating liquid in which the CTM alone or the CTM and a binder resin are dissolved or dispersed in a proper solvent on the CGL, and drying the liquid. In addition, the CTL may optionally include two or more of additives such as plasticizers, leveling agents and antioxidants.

As a method of coating the thus prepared coating liquid, a conventional coating method such as a dip coating method, a spray coating method, a bead coating method, a nozzle coating method, a spinner coating method and a ring coating method can be used.

Next, a single-layered photosensitive layer 33 is explained. A photoreceptor in which the above-mentioned CGM is dispersed in the binder resin can be used. The photosensitive layer can be formed by coating a coating liquid in which a CGM, a CTM and a binder resin are dissolved or dispersed in a proper solvent, and then drying the coated liquid.

In addition, the photosensitive layer may optionally include additives such as plasticizers, leveling agents and antioxidants.

Suitable binder resins include the resins mentioned above in the CTL 37. The resins mentioned above in the CGL 35 can be added as a binder resin. In addition, the polymeric CTLs mentioned above can be also used as a binder resin preferably. A content of the CGM is preferably from 5 to 40 parts by weight, and a content of the CTM is preferably from 0 to 190, and more preferably from 50 to 150 parts by weight per 100 parts by weight of the binder resin. The single-layered photosensitive layer can be formed by coating a coating liquid in which a CGM, a binder resin and a CTM are dissolved or dispersed in a solvent such as tetrahydrofuran, dioxane, dichloroethane, cyclohexane, etc. by a coating method such as a dip coating method, spray coating method, a bead coating method and a ring coating method. The thickness of the photosensitive layer is preferably from 5 to 25 μm.

In the photoreceptor of the present invention, an undercoat layer may be formed between the substrate 31 and the photosensitive layer. The undercoat layer includes a resin as a main component. Since a photosensitive layer is typically formed on the undercoat layer by coating a liquid including an organic solvent, the resin in the undercoat layer preferably has good resistance against general organic solvents. Specific examples of such resins include water-soluble resins such as polyvinyl alcohol resins, casein and polyacrylic acid sodium salts; alcohol soluble resins such as nylon copolymers and methoxymethylated nylon resins; and thermosetting resins capable of forming a three-dimensional network such as polyurethane resins, melamine resins, alkyd-melamine resins, epoxy resins and the like. The undercoat layer may include a fine powder of metal oxides such as titanium oxide, silica, alumina, zirconium oxide, tin oxide and indium oxide to prevent occurrence of moiré in the recorded images and to decrease residual potential of the photoreceptor.

The undercoat layer can be formed by coating a coating liquid using a proper solvent and a proper coating method similarly to those for use in formation of the photosensitive layer mentioned above. The undercoat layer may be formed using a silane coupling agent, titanium coupling agent or a chromium coupling agent. In addition, a layer of aluminum oxide which is formed by an anodic oxidation method and a layer of an organic compound such as polyparaxylylene (parylene) or an inorganic compound such as SiO, $SnO_2$, $TiO_2$, ITO or $CeO_2$ which is formed by a vacuum evaporation method is also preferably used as the undercoat layer. The thickness of the undercoat layer is preferably 0 to 5 μm.

In the photoreceptor of the present invention, the protection layer 39 is optionally formed overlying the photosensitive layer. Suitable materials for use in the protection layer 39 include ABS resins, ACS resins, olefin-vinyl monomer copolymers, chlorinated polyethers, aryl resins, phenolic resins, polyacetal, polyamides, polyester resins, polyamideimide, polyacrylates, polyarylsulfone, polybutylene, polybutylene terephthalate, polycarbonate, polyethersulfone, polyethylene, polyethylene terephthalate, polyimides, acrylic resins, polymethylpentene, polypropylene, polyphenyleneoxide, polysulfone, polystyrene, AS resins, butadiene-styrene copolymers, polyurethane, polyvinyl chloride, polyvinylidene chloride, epoxy resins and the like, because of preventing an increase of residual potential of the resultant photoreceptor. Among these materials, the polycarbonate resin and the polyarylate resin are preferably and effectively used in terms of dispersibility of a filler, decrease of residual potential and coating defect of the resultant photoreceptor.

The protection layer 39 preferably includes a filler for the purpose of improving abrasion resistance thereof. As a solvent for use in forming the protection layer, tetrahydrofuran, dioxane, toluene, dichloromethane, monochlorobenzene, dichloroethane, cyclohexanone, methyl ethyl ketone, acetone and the like solvents which are all used in the CTL 37 can be used. However, a high-viscosity solvent is preferably used in dispersion, and a high-volatile solvent is preferably used in coating. When such a solvent as satisfies the conditions is not available, a mixture of two or more of solvents having each property can be used, which occasionally improves dispersibility of the filler and decreases residual potential of the resultant photoreceptor.

Further, the protection layer may include the isoindole derivative of the present invention. The low-molecular-weight CTM and the polymeric CTM mentioned above are preferably and effectively included therein to decrease residual potential of the resultant photoreceptor and to improve quality of the resultant images.

As a method of forming the protection layer, a conventional coating method such as a dip coating method, a spray coating method, a bead coating method, a nozzle coating method, a spinner coating method and ring coating method can be used. In particular, the spray coating method is preferably used in terms of coated film uniformity.

In the photoreceptor of the present invention, an intermediate layer may be formed between the photosensitive layer and the protection layer. The intermediate layer includes a resin as a main component. Specific examples of the resin include polyamides, alcohol soluble nylons, water-soluble polyvinyl butyral, polyvinyl butyral, polyvinyl alcohol, and the like. The intermediate layer can be formed by one of the above-mentioned known coating methods. The thickness of the intermediate layer is preferably from 0.05 to 2 μm.

In the photoreceptor of the present invention, antioxidants, plasticizers, lubricants, ultraviolet absorbents and leveling agents can be included in each layer such as the CGL, CTL, undercoat layer, protection layer and intermediate layer for environmental improvement, above all for the purpose of preventing decrease of photosensitivity and increase of residual potential. Such compounds are shown as follows.

Suitable antioxidants for use in the layers of the photoreceptor include the following compounds but are not limited thereto.

(a) Phenolic Compounds 2,6-di-t-butyl-p-cresol, butylated hydroxyanisole, 2,6-di-t-butyl-4-ethylphenol, n-octadecyl-3-(4'-hydroxy-3',5'-di-t-butylphenol), 2,2'-methylene-bis-(4-methyl-6-t-butylphenol), 2,2'-methylene-bis-(4-ethyl-6-t-butylphenol), 4,4'-thiobis-(3-methyl-6-t-butylphenol), 4,4'-butylidenebis-(3-methyl-6-t-butylphenol), 1,1,3-tris-(2-methyl-4-hydroxy-5-t-butylphenyl)butane, 1,3,5-trimethyl-2,4,6-tris(3,5-di-t-butyl-4-hydroxybenzyl)benzene, tetrakis-[methylene-3-(3',5'-di-t-butyl-4'-hydroxyphenyl)propionate]methane, bis[3,3'-bis(4'-hydroxy-3'-t-butylphenyl)butyric acid]glycol ester, tocophenol compounds, and the like.

(b) Paraphenylenediamine Compounds

N-phenyl-N'-isopropyl-p-phenylenediamine, N,N'-di-sec-butyl-p-phenylenediamine, N-phenyl-N-sec-butyl-p-phenylenediamine, N,N'-di-isopropyl-p-phenylenediamine, N,N'-dimethyl-N,N'-di-t-butyl-p-phenylenediamine, and the like.

(c) Hydroquinone Compounds 2,5-di-t-octylhydroquinone, 2,6-didodecylhydroquinone, 2-dodecylhydroquinone, 2-dodecyl-5-chlorohydroquinone, 2-t-octyl-5-methylhydroquinone, 2-(2-octadecenyl)-5-methylhydroquinone and the like.

(d) Organic Sulfur-Containing Compounds

Dilauryl-3,3'-thiodipropionate, distearyl-3,3'-thiodipropionate, ditetradecyl-3,3'-thiodipropionate, and the like.

(e) Organic Phosphorus-Containing Compounds

Triphenylphosphine, tri(nonylphenyl)phosphine, tri(dinonylphenyl)phosphine, tricresylphosphine, tri(2,4-dibutylphenoxy)phosphine and the like.

Suitable plasticizers for use in the layers of the photoreceptor include the following compounds, but are not limited thereto.

(a) Phosphoric Acid Esters Plasticizers

Triphenyl phosphate, tricresyl phosphate, trioctyl phosphate, octyldiphenyl phosphate, trichloroethyl phosphate, cresyldiphenyl phosphate, tributyl phosphate, tri-2-ethylhexyl phosphate, triphenyl phosphate, and the like.

(b) Phthalic Acid Esters Plasticizers

Dimethyl phthalate, diethyl phthalate, diisobutyl phthalate, dibutyl phthalate, diheptyl phthalate, di-2-ethylhexyl phthalate, diisooctyl phthalate, di-n-octyl phthalate, dinonyl phthalate, diisononyl phthalate, diisodecyl phthalate, diundecyl phthalate, ditridecyl phthalate, dicyclohexyl phthalate, butylbenzyl phthalate, butyllauryl phthalate, methyloleyl phthalate, octyldecyl phthalate, dibutyl fumarate, dioctyl fumarate, and the like.

(c) Aromatic Carboxylic Acid Esters Plasticizers

Trioctyl trimellitate, tri-n-octyl trimellitate, octyl oxybenzoate, and the like.

(d) Dibasic Fatty Acid Esters Plasticizers

Dibutyl adipate, di-n-hexyl adipate, di-2-ethylhexyl adipate, di-n-octyl adipate, n-octyl-n-decyl adipate, diisodecyl adipate, dialkyl adipate, dicapryl adipate, di-2-etylhexyl azelate, dimethyl sebacate, diethyl sebacate, dibutyl sebacate, di-n-octyl sebacate, di-2-ethylhexyl sebacate, di-2-ethoxyethyl sebacate, dioctyl succinate, diisodecyl succinate, dioctyl tetrahydrophthalate, di-n-octyl tetrahydrophthalate, and the like.

(e) Fatty Acid Ester Derivatives

Butyl oleate, glycerin monooleate, methyl acetylricinolate, pentaerythritol esters, dipentaerythritol hexaesters, triacetin, tributyrin, and the like.

(f) Oxyacid Esters Plasticizers

Methyl acetylricinolate, butyl acetylricinolate, butylphthalylbutyl glycolate, tributyl acetylcitrate, and the like.

(g) Epoxy Plasticizers

Epoxydized soybean oil, epoxydized linseed oil, butyl epoxystearate, decyl epoxystearate, octyl epoxystearate, benzyl epoxystearate, dioctyl epoxyhexahydrophthalate, didecyl epoxyhexahydrophthalate, and the like.

(h) Dihydric Alcohol Esters Plasticizers

Diethylene glycol dibenzoate, triethylene glycol di-2-ethylbutyrate, and the like.

(i) Chlorine-Containing Plasticizers

Chlorinated paraffin, chlorinated diphenyl, methyl esters of chlorinated fatty acids, methyl esters of methoxychlorinated fatty acids, and the like.

(j) Polyester Plasticizers

Polypropylene adipate, polypropylene sebacate, acetylated polyesters, and the like.

(k) Sulfonic Acid Derivatives

P-toluene sulfonamide, o-toluene sulfonamide, p-toluene sulfoneethylamide, o-toluene sulfoneethylamide, toluene sulfone-N-ethylamide, p-toluene sulfone-N-cyclohexylamide, and the like.

(l) Citric Acid Derivatives

Triethyl citrate, triethyl acetylcitrate, tributyl citrate, tributyl acetylcitrate, tri-2-ethylhexyl acetylcitrate, n-octyldecyl acetylcitrate, and the like.

(m) Other Compounds

Terphenyl, partially hydrated terphenyl, camphor, 2-nitro diphenyl, dinonyl naphthalene, methyl abietate, and the like.

Suitable lubricants for use in the layers of the photoreceptor include the following compounds but are not limited thereto.

(a) Hydrocarbon Compounds

Liquid paraffins, paraffin waxes, micro waxes, low molecular weight polyethylenes, and the like.

(b) Fatty Acid Compounds

Lauric acid, myristic acid, palmitic acid, stearic acid, arachidic acid, behenic acid, and the like.

(c) Fatty Acid Amide Compounds

Stearic acid amide, palmitic acid amide, oleic acid amide, methylenebisstearamide, ethylenebisstearamide, and the like.

(d) Ester Compounds

Lower alcohol esters of fatty acids, polyhydric alcohol esters of fatty acids, polyglycol esters of fatty acids, and the like.

(e) Alcohol Compounds

Cetyl alcohol, stearyl alcohol, ethylene glycol, polyethylene glycol, polyglycerol, and the like.

(f) Metallic Soaps

Lead stearate, cadmium stearate, barium stearate, calcium stearate, zinc stearate, magnesium stearate, and the like.

(g) Natural Waxes

Carnauba wax, candelilla wax, beeswax, spermaceti, insect wax, montan wax, and the like.

(h) Other Compounds

Silicone compounds, fluorine compounds, and the like.

Suitable ultraviolet absorbing agents for use in the layers of the photoreceptor include the following compounds but are not limited thereto.

(a) Benzophenone Compounds 2-hydroxybenzophenone, 2,4-dihydroxybenzophenone, 2,2',4-trihydroxybenzophenone, 2,2',4,4'-tetrahydroxybenzophenone, 2,2'-dihydroxy-4-methoxybenzophenone, and the like.

(b) Salicylate Compounds

Phenyl salicylate, 2,4-di-t-butylphenyl-3,5-di-t-butyl-4-hydroxybenzoate, and the like.

(c) Benzotriazole Compounds (2'-hydroxyphenyl)benzotriazole, (2'-hydroxy-5'-methylphenyl)benzotriazole and (2'-hydroxy-3'-t-butyl-5'-methylphenyl)-5-chlorobenzotriazole.

(d) Cyano Acrylate Compounds

Ethyl-2-cyano-3,3-diphenyl acrylate, methyl-2-carbomethoxy-3-(paramethoxy)acrylate, and the like.

(e) Quenchers (Metal Complexes)

Nickel(2,2'-thiobis(4-t-octyl)phenolate)-n-butylamine, nickeldibutyldithiocarbamate, cobaltdicyclohexyldithiophosphate, and the like.

(f) HALS (Hindered Amines)

Bis(2,2,6,6-tetramethyl-4-piperidyl)sebacate, bis(1,2,2,6,6-pentamethyl-4-piperidyl)sebacate, 1-[2-{3-(3,5-di-t-butyl-4-hydroxyphenyl)propionyloxy}ethyl]-4-{3-(3,5-di-t-butyl-4-hydroxyphenyl)propionyloxy}-2,2,6,6-tetramethylpyridine, 8-benzyl-7,7,9,9-tetramethyl-3-octyl-1,3,8-triazaspiro[4,5]undecane-2,4-dione, 4-benzoyloxy-2,2,6,6-tetramethylpiperidine, and the like.

Next, the electrophotographic method and image forming apparatus of the present invention of the present invention will be explained in detail.

Figure 7:
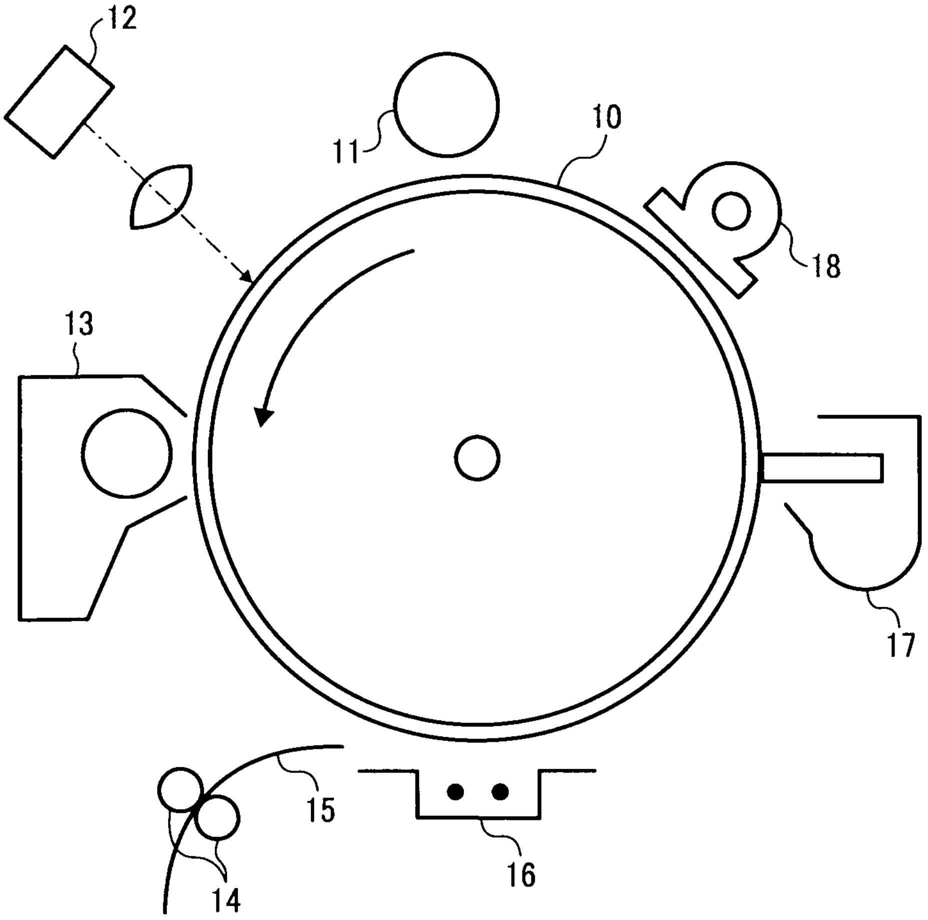
FIG. 7 is a schematic view for explaining the electrophotographic image forming process and the electrophotographic image forming apparatus of the present invention.

FIG. 7 is a schematic view for explaining an embodiment of the electrophotographic process and image forming apparatus of the present invention, the following example belongs to the scope of the present invention.

Photoreceptor 10 rotates in the direction of an arrow in FIG. 7, and a charger 11, an imagewise light irradiator 12, an image developer 13, a transferer 16, a cleaner 17, a discharger 18, etc. are located around the photoreceptor 10. The cleaner 17 and the discharger 18 can be omitted.

Image forming operation is basically made as follows. The surface of the photoreceptor 10 is uniformly charged by the charger 11. The imagewise light irradiator 12 irradiates the surface of the photoreceptor 10 with imagewise light to form an electrostatic latent image. The electrostatic latent image is developed by the image developer 13 to form a toner image on the surface of the photoreceptor. The toner image is transferred by the transferer 16 onto a transfer paper 15 fed to a transfer site by a feeding roller 14. The toner image is fixed on the transfer paper by a fixer (not shown). A toner untransferred onto the transfer paper is removed by the cleaner 17. A charge remaining on the photoreceptor is discharged by the discharger 18, and the next cycle follows.

In FIG. 7, the photoreceptor 10 has the shape of a drum, and may have the shape of a sheet or an endless belt. Known chargers such as corotrons, scorotrons, solid state chargers, charging rollers and charging brushes can be used for the charger 11 and the transferer 16.

Suitable light sources for the imagewise light irradiator 12 and the discharger 18 include general light-emitting materials such as fluorescent lamps, tungsten lamps, halogen lamps, mercury lamps, sodium lamps, LEDs, LDs, light sources using electroluminescence (EL), etc. Among these, LEDs and LDs are mostly used.

In addition, in order to obtain light having a desired wave length range, filters such as sharp-cut filters, band pass filters, near-infrared cutting filters, dichroic filters, interference filters, color temperature converting filters can be used.

The above-mentioned light sources can be used for not only the process illustrated in FIG. 5, but also other processes such as a transfer process, a discharging process, a cleaning process, a pre-exposure process include light irradiation to the photoreceptor 10. However, in the discharging process, the photoreceptor 10 is largely influenced by the irradiation, resulting in occasional deterioration of chargeability and increase of residual potential.

Therefore, a reverse bias is optionally applied in the charging process and cleaning process instead of irradiation to discharge, which improves durability of the photoreceptor.

When the photoreceptor positively (or negatively) charged is exposed to imagewise light, an electrostatic latent image having a positive (or negative) charge is formed on the photoreceptor. When the latent image having a positive (or negative) charge is developed with a toner having a negative (or positive) charge, a positive image can be obtained. In contrast, when the latent image having a positive (negative) charge is developed with a toner having a positive (negative) charge, a negative image can be obtained.

As the developing method, known developing methods can be used. Further, known discharging methods can be used as the discharging method.

Among contaminants adhering the surface of a photoreceptor, a discharge material generated by charging and an external additive in a toner are vulnerable to humidity and cause abnormal images. A paper powder is also one of materials causing abnormal images, and it adheres to a photoreceptor, incidentally resulting in not only production of abnormal images but also deterioration of abrasion resistance and sectional abrasion of the photoreceptor. Therefore, it is preferable that the photoreceptor does not directly contact a paper in terms of high quality images.

When a toner image formed on the photoreceptor 10 by the image developer 13 is transferred onto the transfer paper 15, all of the toner image is not transferred thereto, and a residual toner remains on the surface of the photoreceptor 10. The residual toner is removed from the photoreceptor by a fur brush or a cleaning blade.

The residual toner remaining on the photoreceptor can be removed by only the brush or a combination with the blade.

The photoreceptor of the present invention is very effectively used in a tandem-type image forming apparatus including plural photoreceptors for respective image developers parallely forming plural color toner images. The tandem-type image forming apparatus including at least 4 color toners, i.e., yellow (Y), magenta (M), cyan (C) and black (K), respective image developers holding them, and at least 4 photoreceptors therefor is capable of printing full-color images at very higher speed than conventional full-color image forming apparatuses.

Figure 8:
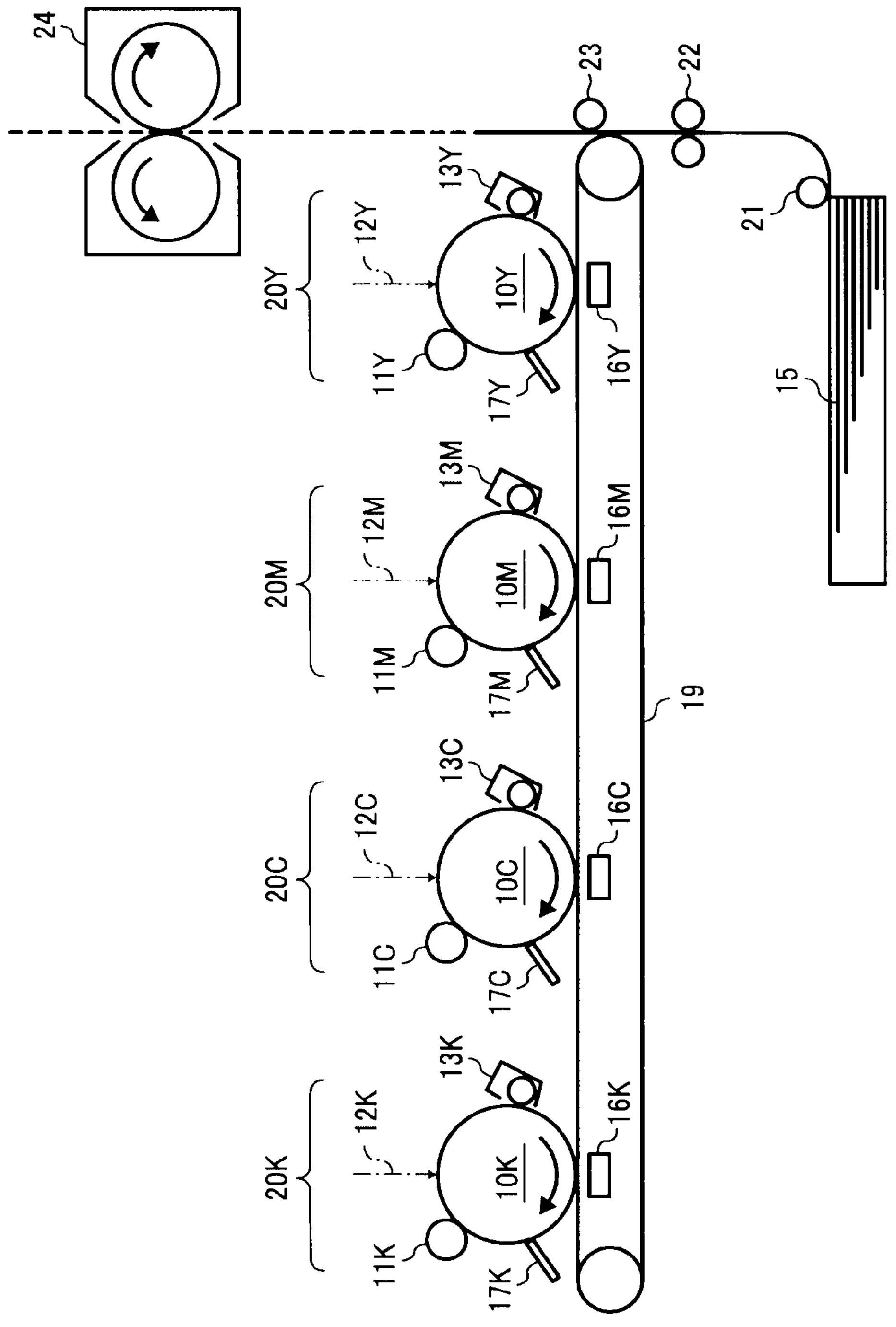
FIG. 8 is a schematic view illustrating another embodiment of the electrophotographic image forming process of the present invention.

FIG. 8 is a schematic view illustrating an embodiment of the tandem-type full-color image forming apparatus of the present invention, and the following modified embodiment is included in the present invention.

In FIG. 8, numerals 10C, 10M, 10Y and 10K represent drum-shaped photoreceptors of the present invention. The photoreceptors 10C, 10M, 10Y and 10K rotate in the direction indicated by an arrow, and around them, chargers 11C, 11M, 11Y and 11K; image developers 13C, 13M, 13Y and 13*k*; and cleaners 17C, 17M, 17Y and 17K are arranged in a rotation order thereof.

Laser beams 12C, 12M, 12Y and 12K from irradiators (not shown) irradiate the surfaces of the photoreceptors between the chargers 11C, 11M, 11Y and 11K and image developers 13C, 13M, 13Y and 13*k* to form electrostatic latent images on the surfaces of the photoreceptors 10C, 10M, 10Y and 10K.

Four image forming units 20C, 20M, 20Y and 20K including the photoreceptors 10C, 10M, 10Y and 10K are arranged along a transfer feeding belt 19 feeding a transfer material. The transfer feeding belt 19 contacts the photoreceptors 10C, 10M, 10Y and 10K between the image developers 13C, 13M, 13Y and 13*k* and cleaners 17C, 17M, 17Y and 17K of the image forming units 20C, 20M, 20Y and 20K. Transfer members 16*c*, 16M, 16Y and 16K are arranged on a backside of the transfer feeding belt 19, which is an opposite side to the photoreceptors, to apply a transfer bias to the transfer feeding belt 19. The image forming units 20C, 20M, 20Y and 20K just handle different color toners respectively, and have the same structures.

In the full-color electrophotographic apparatus in FIG. 6, images are formed as follows. First, in the image forming units 20C, 20M, 20Y and 20K, the photoreceptors 10C, 10M, 10Y and 10K are charged by the chargers 11C, 11M, 11Y and 11K rotating in the same direction of the photoreceptors. Next, the laser beams 12C, 12M, 12Y and 12K from irradiators (not shown) irradiate the surfaces of the photoreceptors to form electrostatic latent images having different colors respectively thereon.

Then, the image developers 13C, 13M, 13Y and 13*k* develop the electrostatic latent images to form toner images. The image developers 13C, 13M, 13Y and 13*k* develop the electrostatic latent images with toners having a cyan color C, a magenta color M, a yellow color Y and a black color K respectively. The color toner images respectively formed on the photoreceptors 10C, 10M, 10Y and 10K are overlaid on transfer feeding belt 19.

The transfer paper 15 is fed by a paper feeding roller 21 from a tray and stopped once by a pair of registration rollers 22, and fed onto a transfer member 23 in timing with formation of the toner images on the photoreceptors. The toner images held on the transfer feeding belt 19 are transferred to the transfer paper 15 by an electric field formed with a potential difference between the transfer bias applied by the transfer member 23 and the transfer feeding belt 19. The toner images transferred on the transfer paper is fixed thereon by a fixer 24 and the transfer paper 15 on which the toner images are fixed is fed onto a sheet receiver (not shown). Residual toners remaining on the photoreceptors 10C, 10M, 10Y and 10K, which were not transferred on the transfer paper at a transfer position are collected by the cleaners 17C, 17M, 17Y and 17K.

The intermediate transfer method as shown in FIG. 8 is effectively used for full-color image forming apparatuses in particular. After plural toner images are formed on the intermediate transferer, they are transferred onto a paper at a time to prevent shifted color, which produces images having higher quality.

Any known drum-shaped and belt-shaped intermediate transferers can be used in the present invention, and are effectively and efficiently used for higher durability of a photoreceptor or quality images having higher quality.

In FIG. 8, the image forming units are lined in order of C, M, Y and K from an upstream to a downstream of feeding direction of the transfer sheet. However, the order is not limited thereto and the color orders are optional. When only a black image is produced, the image forming units 20C, 20M, 20Y and 20K except for 20K can be stopped in the apparatus of the present invention.

The above-mentioned image forming units may be fixedly set in a copier, a facsimile or a printer. However, the image forming units may be set therein as a process cartridge.

Figure 9:
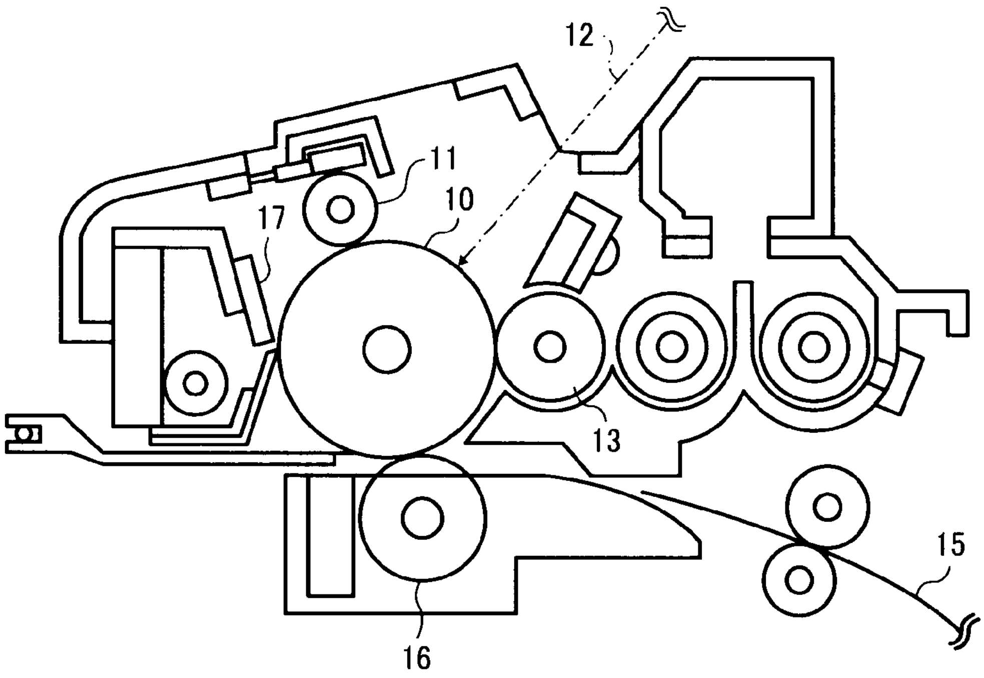
FIG. 9 is a schematic view for explaining an embodiment of the process cartridge of the present invention.

The process cartridge means an image forming unit (or device) including at least a photoreceptor 10, and one of a charger 11, an imagewise light irradiator 12, an image developer 13, an image transferer 16, a cleaner 17 and a discharger as shown in FIG. 9.

The above-mentioned tandem image forming apparatus produces full-color images at high speed because of capable of transferring plural toner images at a time.

However, the apparatus is inevitably enlarged because of needing at least four photoreceptors, and depending on an amount of toner consumed, the photoreceptors are differently abraded, resulting in deterioration of color reproducibility and production of abnormal images.

The photoreceptor having high sensitivity and stability of the present invention can have smaller diameter, and can produce full-color images having good color reproducibility even when the four photoreceptors are unevenly used for long periods because increase of residual potential and sensitivity deterioration are reduced.

Having generally described this invention, further understanding can be obtained by reference to certain specific examples which are provided herein for the purpose of illustration only and are not intended to be limiting. In the descriptions in the following examples, the numbers represent weight ratios in parts, unless otherwise specified.

EXAMPLES

Example 1

Preparation of N-(3-methylphenyl)-2,5-diphenylisoindole

A diketone derivative having the following formula (5) (4.36 g, 15 mmol), 3-methyltoluidine (4.82 g, 45.0 mmol) and 1,2,4-trichlorobenzene were mixed at 200° C. for 3 hrs to prepare a mixture. After the mixture was cooled to have room temperature, it was subjected to methanol to form a precipitate. The precipitate was filtered out and dissolved in 100 ml of dichloromethane to prepare a solution. 2,3-dicyano4,5-dichloroquinone (3.0 g, 13.2 mmol) was added to the solution and the solution was stirred for 30 min at room temperature. Water was added to the solution and the solution was subjected to dichloromethane to obtain an extract, and the extract was washed with water. An organic layer was subjected to a reduced pressure and condensed to obtain a black solid. The black solid was subjected to silica gel column treatment with dichloromethane to obtain 1.0 g of a faint yellow powder N-(3 methylphenyl)-2,5-diphenylisoindole having the following formula (6) (yield rate of 30.6%).

(5)

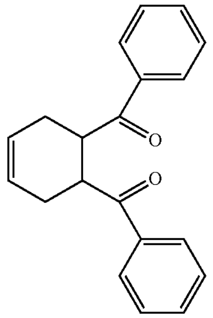

-continued (6)

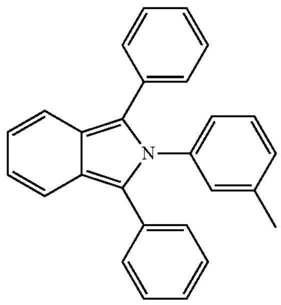

The obtained derivative has a melting point of from 201.5 to 202.0. An element analytical value thereof was as follows when it was $C_{27}H_{21}N$.

| | C | H | N |
|---|---|---|---|
| Measured value | 90.2 | 5.9 | 3.9 |
| Calculated value | 90.2 | 5.9 | 3.8 |

An infrared absorption spectrum (KBr pellet method) thereof is shown in FIG. 1.

Example 2

Preparation of N-(4-methylphenyl)-2,5-diphenylisoindole

The procedure for preparation of the N-(3-methylphenyl)-2,5-diphenylisoindole in Example 1 was repeated to prepare an extra N-phenylisoindole derivative. A formula, a melting point and an element analytical value thereof are shown in Table A.

Example 3

Preparation of N-(3-methylphenyl)-2,5-diphenylisoindole

The procedure for preparation of the N-(3-methylphenyl)-2,5-diphenylisoindole in Example 1 was repeated to prepare another extra N-phenylisoindole derivative. A formula, a melting point and an element analytical value thereof are shown in Table A.

Preparation of N-(4-methylphenyl)-2,5-diphenylisoindole

The procedure for preparation of the N-(3-methylphenyl)-2,5-diphenylisoindole in Example 1 was repeated to prepare a further extra N-phenylisoindole derivative. A formula, a melting point and an element analytical value thereof are shown in Table A.

TABLE A

| Example | Formula | Melting point (° C.) Recrystallizing solvent | Element analytical value Measu. (Calcu.) C % | H % | N % |
|---|---|---|---|---|---|
| 2 | 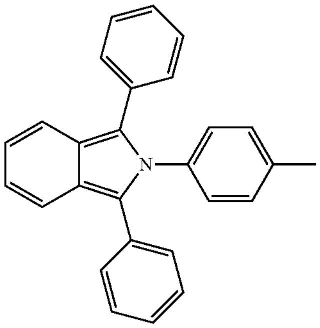 [SMILES: Cc1ccc(-n2c(-c3ccccc3)c3ccccc3c2-c2ccccc2)cc1] | 249.0-250.0 | 90.0 (90.2) | 5.9 (5.9) | 4.0 (3.9) |
| 3 | 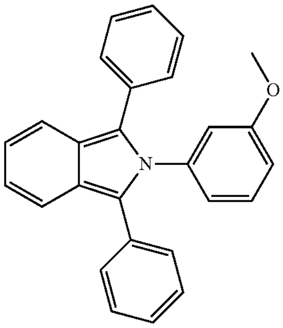 [SMILES: COc1cccc(-n2c(-c3ccccc3)c3ccccc3c2-c2ccccc2)c1] | 237.0-280.0 | 86.4 (86.4) | 5.7 (5.6) | 3.9 (3.7) |
| 4 | 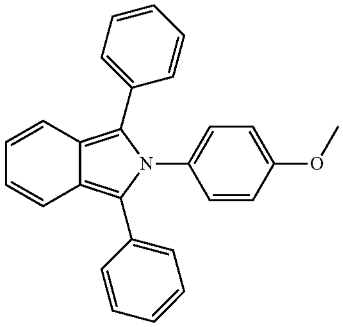 [SMILES: COc1ccc(-n2c(-c3ccccc3)c3ccccc3c2-c2ccccc2)cc1] | 229.5-231.0 | 86.3 (86.4) | 5.8 (5.6) | 3.6 (3.7) |

Example 5

An undercoat coating liquid, a CGL coating liquid and a CTL coating liquid, which have the following formulations were coated and dried in this order on an aluminum cylinder to form an undercoat layer 3.5 μm thick, a charge generation layer 0.2 μm thick, a charge transport layer 23 μm thick thereon (photoreceptor No. 1).

| (Undercoat Layer Coating Liquid) | |
|---|---|
| Titanium dioxide powder | 400 |
| (CR-EL from Ishihara Sangyo Kaisha, ltd.) | |
| Melamine resin | 65 |
| (Super Bekkamin G821-60 from Dainippon Ink And Chemicals, inc.) | |
| Alkyd resin | 120 |
| (Bekkolite M6401-50 from Dainippon Ink And Chemicals, inc.) | |
| 2-butanone | 400 |

-continued

| (CGL coating liquid) | |
|---|---|
| Fluorenone bisazo pigment having the following formula | 12 |
| 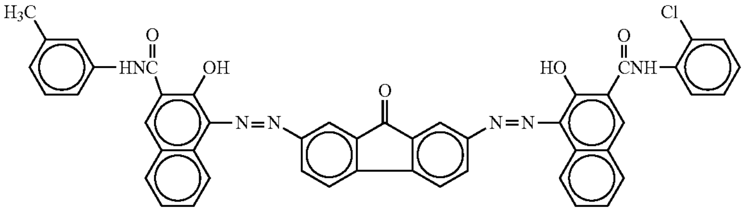 | |
| Polyvinyl butyral resin (XYHL from Union Carbide Corporation) | 5 |
| 2-butanone | 200 |
| Cyclohexanone | 400 |
| (CTL coating liquid) | |
| Polycarbonate resin (Z-polyca from Teijin Chemicals Ltd.) | 10 |
| Isoindole derivative No. 2 | 10 |
| Tetrahydrofuran | 100 |

The photoreceptor was installed in a process cartridge, and the process cartridge was installed in imagio MF2200 modified to have negatively charging corona charger and an LD having a wavelength of 655 nm from Ricoh Company, Ltd. The dark space potential thereof was set at −800 (V), 100,000 images were continuously produced thereby. The initial dark space potential and a bright space potential were measured. Ten dot images having an image density of 5% and a pixel density of 600 dpi×600 dpi were continuously produced, and sharpness thereof were observed by a stereomicroscope to classify the images into the following 5 grades.

5: Clear profile

4: Very slight blurred profile

3: Slight blurred profile

2: Blurred profile observed, and a problem depending on images

1: Dot image is not identified

The results are shown in Table 2.

Example 6

The procedure for preparation and evaluation of the photoreceptor No. 1 in Example 5 was repeated to prepare and evaluate a photoreceptor No. 2 except for using the isoindole derivative No. 1 instead of the isoindole derivative No. 2. The evaluation results of the photoreceptor No. 2 are shown in Table 2.

Example 7

The procedure for preparation and evaluation of the photoreceptor No. 1 in Example 5 was repeated to prepare and evaluate a photoreceptor No. 3 except for using the isoindole derivative No. 3 instead of the isoindole derivative No. 2. The evaluation results of the photoreceptor No. 3 are shown in Table 2.

Example 8

The procedure for preparation and evaluation of the photoreceptor No. 1 in Example 5 was repeated to prepare and evaluate a photoreceptor No. 4 except for using the isoindole derivative No. 5 instead of the isoindole derivative No. 2. The evaluation results of the photoreceptor No. 4 are shown in Table 2.

Example 9

The procedure for preparation and evaluation of the photoreceptor No. 1 in Example 5 was repeated to prepare and evaluate a photoreceptor No. 5 except for using the isoindole derivative No. 7 instead of the isoindole derivative No. 2. The evaluation results of the photoreceptor No. 5 are shown in Table 2.

Example 10

The procedure for preparation and evaluation of the photoreceptor No. 1 in Example 5 was repeated to prepare and evaluate a photoreceptor No. 6 except for using the isoindole derivative No. 9 instead of the isoindole derivative No. 2. The evaluation results of the photoreceptor No. 6 are shown in Table 2.

Example 11

The procedure for preparation and evaluation of the photoreceptor No. 1 in Example 5 was repeated to prepare and evaluate a photoreceptor No. 7 except for using the isoindole derivative No. 11 instead of the isoindole derivative No. 2. The evaluation results of the photoreceptor No. 7 are shown in Table 2.

Example 12

The procedure for preparation and evaluation of the photoreceptor No. 1 in Example 5 was repeated to prepare and evaluate a photoreceptor No. 8 except for using the isoindole derivative No. 13 instead of the isoindole derivative No. 2. The evaluation results of the photoreceptor No. 8 are shown in Table 2.

Example 13

The procedure for preparation and evaluation of the photoreceptor No. 1 in Example 5 was repeated to prepare and evaluate a photoreceptor No. 9 except for using the isoindole derivative No. 15 instead of the isoindole derivative No. 2. The evaluation results of the photoreceptor No. 9 are shown in Table 2.

Example 14

The procedure for preparation and evaluation of the photoreceptor No. 1 in Example 5 was repeated to prepare and evaluate a photoreceptor No. 10 except for using the isoindole derivative No. 17 instead of the isoindole derivative No. 2. The evaluation results of the photoreceptor No. 10 are shown in Table 2.

Example 15

The procedure for preparation and evaluation of the photoreceptor No. 1 in Example 5 was repeated to prepare and evaluate a photoreceptor No. 11 except for using the isoindole derivative No. 21 instead of the isoindole derivative No. 2. The evaluation results of the photoreceptor No. 11 are shown in Table 2.

Example 16

The procedure for preparation and evaluation of the photoreceptor No. 1 in Example 5 was repeated to prepare and evaluate a photoreceptor No. 12 except for using the isoindole derivative No. 23 instead of the isoindole derivative No. 2. The evaluation results of the photoreceptor No. 12 are shown in Table 2.

Example 17

The procedure for preparation and evaluation of the photoreceptor No. 1 in Example 5 was repeated to prepare and evaluate a photoreceptor No. 13 except for using the isoindole derivative No. 25 instead of the isoindole derivative No. 2. The evaluation results of the photoreceptor No. 13 are shown in Table 2.

Example 18

The procedure for preparation and evaluation of the photoreceptor No. 1 in Example 5 was repeated to prepare and evaluate a photoreceptor No. 14 except for using the isoindole derivative No. 34 instead of the isoindole derivative No. 2. The evaluation results of the photoreceptor No. 14 are shown in Table 2.

Example 19

The procedure for preparation and evaluation of the photoreceptor No. 1 in Example 5 was repeated to prepare and evaluate a photoreceptor No. 15 except for using the isoindole derivative No. 36 instead of the isoindole derivative No. 2. The evaluation results of the photoreceptor No. 15 are shown in Table 2.

TABLE 2

| | | | Initial | | After 100,000 | |
|---|---|---|---|---|---|---|
| Example No. | Photoreceptor No. | Derivative No. | Bright space potential (V) | Dot sharpness | Dark space potential (V) | Dot sharpness |
| 5 | 1 | 2 | −95 | 5 | −105 | 5 |
| 6 | 2 | 1 | −100 | 5 | −120 | 5 |
| 7 | 3 | 3 | −105 | 5 | −120 | 5 |
| 8 | 4 | 5 | −100 | 5 | −115 | 5 |
| 9 | 5 | 7 | −100 | 5 | −130 | 4 |
| 10 | 6 | 9 | −100 | 5 | −130 | 4 |
| 11 | 7 | 11 | −105 | 5 | −120 | 5 |
| 12 | 8 | 13 | −120 | 5 | −135 | 3 |
| 13 | 9 | 15 | −110 | 5 | −115 | 5 |
| 14 | 10 | 17 | −115 | 5 | −135 | 4 |
| 15 | 11 | 21 | −105 | 5 | −125 | 4 |
| 16 | 12 | 23 | −110 | 5 | −120 | 5 |
| 17 | 13 | 25 | −100 | 5 | −130 | 0 |
| 18 | 14 | 29 | −110 | 5 | −125 | 5 |
| 19 | 15 | 33 | −115 | 5 | −120 | 5 |

Example 20

The procedure for preparation and evaluation of the photoreceptor No. 1 in Example 5 was repeated to prepare and evaluate a photoreceptor No. 16 except for replacing the CTL coating liquid with a CTL coating liquid having the following formulation. The evaluation results of the photoreceptor No. 16 are shown in Table 3.

| (CTL coating liquid) | |
|---|---|
| Polycarbonate resin (Z-polyca from Teijin Chemicals Ltd.) | 10 |
| Isoindole derivative No. 8 | 1 |
| CTM No. 1 having the following formula | 9 |
| 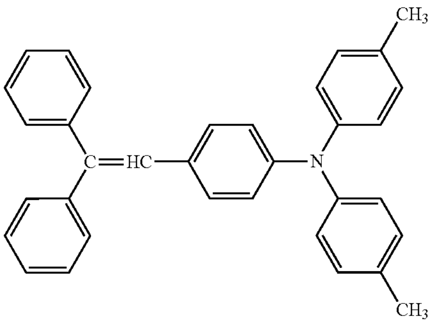 [SMILES: Cc1ccc(N(c2ccc(C)cc2)c2ccc(C=C(c3ccccc3)c3ccccc3)cc2)cc1] | |
| Tetrahydrofuran | 100 |

Example 21

The procedure for preparation and evaluation of the photoreceptor No. 16 in Example 20 was repeated to prepare and evaluate a photoreceptor No. 17 except for using the isoindole derivative No. 1 instead of the isoindole derivative No. 2. The evaluation results of the photoreceptor No. 17 are shown in Table 3.

Example 22

The procedure for preparation and evaluation of the photoreceptor No. 16 in Example 20 was repeated to prepare and evaluate and a photoreceptor No. 18 except for using the isoindole derivative No. 3 instead of the isoindole derivative No. 2. The evaluation results of the photoreceptor No. 18 are shown in Table 3.

Example 23

The procedure for preparation and evaluation of the photoreceptor No. 16 in Example 20 was repeated to prepare and evaluate and a photoreceptor No. 19 except for using the isoindole derivative No. 5 instead of the isoindole derivative No. 2. The evaluation results of the photoreceptor No. 19 are shown in Table 3.

Example 24

The procedure for preparation and evaluation of the photoreceptor No. 16 in Example 20 was repeated to prepare and evaluate and a photoreceptor No. 20 except for using the isoindole derivative No. 7 instead of the isoindole derivative No. 2. The evaluation results of the photoreceptor No. 20 are shown in Table 3.

Example 25

The procedure for preparation and evaluation of the photoreceptor No. 16 in Example 20 was repeated to prepare and evaluate and a photoreceptor No. 21 except for using the isoindole derivative No. 9 instead of the isoindole derivative No. 2. The evaluation results of the photoreceptor No. 21 are shown in Table 3.

Example 26

The procedure for preparation and evaluation of the photoreceptor No. 16 in Example 20 was repeated to prepare and evaluate and a photoreceptor No. 22 except for using the isoindole derivative No. 11 instead of the isoindole derivative No. 2. The evaluation results of the photoreceptor No. 22 are shown in Table 3.

Example 27

The procedure for preparation and evaluation of the photoreceptor No. 16 in Example 20 was repeated to prepare and evaluate and a photoreceptor No. 23 except for using the isoindole derivative No. 13 instead of the isoindole derivative No. 2. The evaluation results of the photoreceptor No. 23 are shown in Table 3.

Example 28

The procedure for preparation and evaluation of the photoreceptor No. 16 in Example 20 was repeated to prepare and evaluate and a photoreceptor No. 24 except for using the isoindole derivative No. 15 instead of the isoindole derivative No. 2. The evaluation results of the photoreceptor No. 24 are shown in Table 3.

Example 29

The procedure for preparation and evaluation of the photoreceptor No. 16 in Example 20 was repeated to prepare and evaluate and a photoreceptor No. 25 except for using the isoindole derivative No. 17 instead of the isoindole derivative No. 2. The evaluation results of the photoreceptor No. 25 are shown in Table 3.

Example 30

The procedure for preparation and evaluation of the photoreceptor No. 16 in Example 20 was repeated to prepare and evaluate and a photoreceptor No. 26 except for using the isoindole derivative No. 21 instead of the isoindole derivative No. 2. The evaluation results of the photoreceptor No. 26 are shown in Table 3.

Example 31

The procedure for preparation and evaluation of the photoreceptor No. 16 in Example 20 was repeated to prepare and evaluate and a photoreceptor No. 27 except for using the isoindole derivative No. 23 instead of the isoindole derivative No. 2. The evaluation results of the photoreceptor No. 27 are shown in Table 3.

Example 32

The procedure for preparation and evaluation of the photoreceptor No. 16 in Example 20 was repeated to prepare and evaluate and a photoreceptor No. 28 except for using the isoindole derivative No. 25 instead of the isoindole derivative No. 2. The evaluation results of the photoreceptor No. 28 are shown in Table 3.

Example 33

The procedure for preparation and evaluation of the photoreceptor No. 16 in Example 20 was repeated to prepare and evaluate and a photoreceptor No. 29 except for using the isoindole derivative No. 34 instead of the isoindole derivative No. 2. The evaluation results of the photoreceptor No. 29 are shown in Table 3.

Example 34

The procedure for preparation and evaluation of the photoreceptor No. 16 in Example 20 was repeated to prepare and evaluate and a photoreceptor No. 30 except for using the isoindole derivative No. 36 instead of the isoindole derivative No. 2. The evaluation results of the photoreceptor No. 30 are shown in Table 3.

TABLE 3

| | | | Initial | | After 100,000 | |
|---|---|---|---|---|---|---|
| Example No. | Photoreceptor No. | Derivative No. | Bright space potential (V) | Dot sharpness | Dark space potential (V) | Dot sharpness |
| 20 | 16 | 8 | −95 | 5 | −110 | 5 |
| 21 | 17 | 1 | −95 | 5 | −115 | 5 |
| 22 | 18 | 3 | −100 | 5 | −110 | 5 |
| 23 | 19 | 5 | −100 | 5 | −120 | 5 |
| 24 | 20 | 7 | −120 | 5 | −135 | 4 |
| 25 | 21 | 9 | −110 | 5 | −125 | 5 |
| 26 | 22 | 11 | −115 | 5 | −130 | 4 |
| 27 | 23 | 13 | −125 | 5 | −135 | 4 |
| 28 | 24 | 15 | −95 | 5 | −105 | 5 |
| 29 | 25 | 17 | −105 | 5 | −120 | 5 |
| 30 | 26 | 21 | −110 | 5 | −135 | 4 |
| 31 | 27 | 23 | −115 | 5 | −125 | 4 |
| 32 | 28 | 25 | −105 | 5 | −115 | 5 |
| 33 | 29 | 29 | −95 | 5 | −115 | 5 |
| 34 | 30 | 33 | −100 | 5 | −115 | 5 |

Example 35

The procedure for preparation and evaluation of the photoreceptor No. 16 in Example 20 was repeated to prepare and evaluate and a photoreceptor No. 31 except for using the isoindole derivative No. 2 instead of No. 8 and 7 parts of the CTM instead of 9 parts. The evaluation results of the photoreceptor No. 31 are shown in Table 4.

Example 39

The procedure for preparation and evaluation of the photoreceptor No. 31 in Example 35 was repeated to prepare and evaluate and a photoreceptor No. 35 except for using a CTM No. 2 having the following formula instead of the CTM No. 1. The evaluation results of the photoreceptor No. 35 are shown in Table 5.

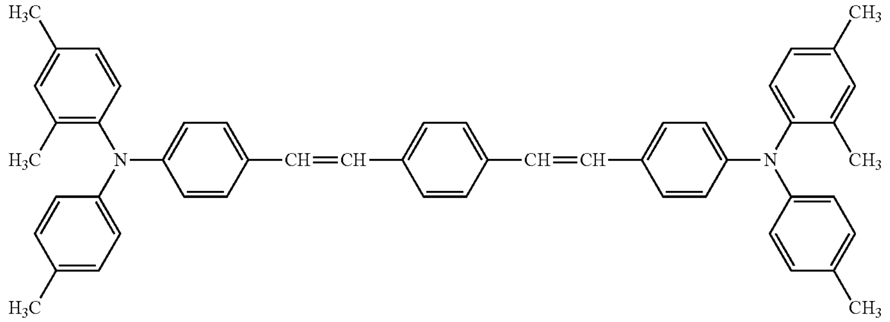 [SMILES: Cc1ccc(N(c2ccc(C=Cc3ccc(C=Cc4ccc(N(c5ccc(C)cc5)c5ccc(C)cc5C)cc4)cc3)cc2)c2ccc(C)cc2C)cc1]

Example 36

The procedure for preparation and evaluation of the photoreceptor No. 16 in Example 20 was repeated to prepare and evaluate and a photoreceptor No. 32 except for using the isoindole derivative No. 16 instead of No. 8 and 7 parts of the CTM instead of 9 parts. The evaluation results of the photoreceptor No. 32 are shown in Table 4.

Example 37

The procedure for preparation and evaluation of the photoreceptor No. 16 in Example 20 was repeated to prepare and evaluate and a photoreceptor No. 33 except for using the isoindole derivative No. 20 instead of No. 8 and 7 parts of the CTM instead of 9 parts. The evaluation results of the photoreceptor No. 33 are shown in Table 4.

Example 38

The procedure for preparation and evaluation of the photoreceptor No. 16 in Example 20 was repeated to prepare and evaluate and a photoreceptor No. 34 except for using the isoindole derivative No. 33 instead of No. 8 and 7 parts of the CTM instead of 9 parts. The evaluation results of the photoreceptor No. 34 are shown in Table 4.

TABLE 4

| | | | Initial | | After 100,000 | |
|---|---|---|---|---|---|---|
| Example No. | Photoreceptor No. | Derivative No. | Bright space potential (V) | Dot sharpness | Dark space potential (V) | Dot sharpness |
| 35 | 31 | 8 | −95 | 5 | −120 | 5 |
| 36 | 32 | 16 | −105 | 5 | −125 | 4 |
| 37 | 33 | 20 | −100 | 5 | −120 | 4 |
| 38 | 34 | 33 | −90 | 5 | −110 | 5 |

Example 40

The procedure for preparation and evaluation of the photoreceptor No. 32 in Example 36 was repeated to prepare and evaluate and a photoreceptor No. 36 except for using the CTM No. 2 instead of the CTM No. 1. The evaluation results of the photoreceptor No. 36 are shown in Table 5.

Example 41

The procedure for preparation and evaluation of the photoreceptor No. 33 in Example 37 was repeated to prepare and evaluate and a photoreceptor No. 37 except for using the CTM No. 2 instead of the CTM No. 1. The evaluation results of the photoreceptor No. 37 are shown in Table 5.

Example 42

The procedure for preparation and evaluation of the photoreceptor No. 34 in Example 38 was repeated to prepare and evaluate and a photoreceptor No. 38 except for using the CTM No. 2 instead of the CTM No. 1. The evaluation results of the photoreceptor No. 38 are shown in Table 5.

TABLE 5

| | | | Initial | | After 100,000 | |
|---|---|---|---|---|---|---|
| Example No. | Photoreceptor No. | Derivative No. | Bright space potential (V) | Dot sharpness | Dark space potential (V) | Dot sharpness |
| 39 | 35 | 8 | −95 | 5 | −105 | 5 |
| 40 | 36 | 16 | −105 | 5 | −125 | 4 |
| 41 | 37 | 20 | −90 | 5 | −115 | 4 |
| 42 | 38 | 33 | −105 | 5 | −125 | 5 |

Example 43

The procedure for preparation and evaluation of the photoreceptor No. 31 in Example 35 was repeated to prepare and evaluate and a photoreceptor No. 39 except for using a CTM No. 3 having the following formula instead of the CTM No. 1. The evaluation results of the photoreceptor No. 39 are shown in Table 6.

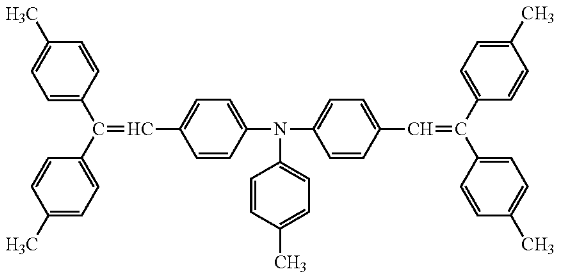 [SMILES: Cc1ccc(C(=Cc2ccc(N(c3ccc(C)cc3)c3ccc(C=C(c4ccc(C)cc4)c4ccc(C)cc4)cc3)cc2)c2ccc(C)cc2)cc1]

Example 44

The procedure for preparation and evaluation of the photoreceptor No. 32 in Example 36 was repeated to prepare and evaluate and a photoreceptor No. 40 except for using the CTM No. 3 instead of the CTM No. 1. The evaluation results of the photoreceptor No. 40 are shown in Table 6.

Example 45

The procedure for preparation and evaluation of the photoreceptor No. 33 in Example 37 was repeated to prepare and evaluate and a photoreceptor No. 41 except for using the CTM No. 3 instead of the CTM No. 1. The evaluation results of the photoreceptor No. 41 are shown in Table 6.

Example 46

The procedure for preparation and evaluation of the photoreceptor No. 34 in Example 38 was repeated to prepare and evaluate and a photoreceptor No. 42 except for using the CTM No. 3 instead of the CTM No. 1. The evaluation results of the photoreceptor No. 42 are shown in Table 6.

TABLE 6

| | | | Initial | | After 100,000 | |
|---|---|---|---|---|---|---|
| Example No. | Photoreceptor No. | Derivative No. | Bright space potential (V) | Dot sharpness | Dark space potential (V) | Dot sharpness |
| 43 | 39 | 1 | −100 | 5 | −110 | 5 |
| 44 | 40 | 16 | −95 | 5 | −115 | 5 |
| 45 | 41 | 20 | −100 | 5 | −105 | 5 |
| 46 | 42 | 30 | −105 | 5 | −120 | 4 |

Example 47

The procedure for preparation and evaluation of the photoreceptor No. 31 in Example 35 was repeated to prepare and evaluate and a photoreceptor No. 43 except for using a CTM No. 4 having the following formula instead of the CTM No. 1. The evaluation results of the photoreceptor No. 43 are shown in Table 7.

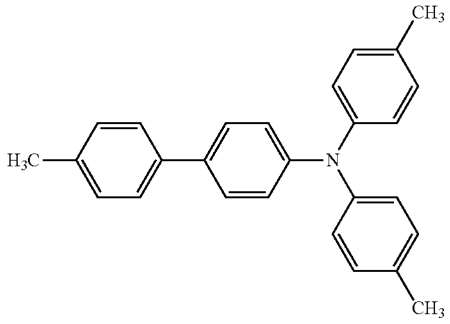

Example 48

The procedure for preparation and evaluation of the photoreceptor No. 32 in Example 36 was repeated to prepare and evaluate and a photoreceptor No. 44 except for using the CTM No. 4 instead of the CTM No. 1. The evaluation results of the photoreceptor No. 44 are shown in Table 7.

Example 49

The procedure for preparation and evaluation of the photoreceptor No. 33 in Example 37 was repeated to prepare and evaluate and a photoreceptor No. 45 except for using the CTM No. 4 instead of the CTM No. 1. The evaluation results of the photoreceptor No. 45 are shown in Table 7.

Example 50

The procedure for preparation and evaluation of the photoreceptor No. 34 in Example 38 was repeated to prepare and evaluate and a photoreceptor No. 46 except for using the CTM No. 4 instead of the CTM No. 1. The evaluation results of the photoreceptor No. 46 are shown in Table 7.

TABLE 7

| | | | Initial | | After 100,000 | |
|---|---|---|---|---|---|---|
| Example No. | Photoreceptor No. | Derivative No. | Bright space potential (V) | Dot sharpness | Dark space potential (V) | Dot sharpness |
| 47 | 43 | 1 | −100 | 5 | −110 | 5 |
| 48 | 44 | 16 | −95 | 5 | −110 | 5 |
| 49 | 45 | 20 | −100 | 5 | −115 | 4 |
| 50 | 46 | 30 | −100 | 5 | −125 | 4 |

Example 51

The procedure for preparation and evaluation of the photoreceptor No. 16 in Example 20 was repeated to prepare and evaluate and a photoreceptor No. 47 except for using the isoindole derivative No. 7 instead of the isoindole derivative No. 8, and replacing the CGL coating liquid and the CTL coating liquid with ones having the following formulations. The evaluation results of the photoreceptor No. 47 are shown in Table 8.

(Preparation of Oxotitaniumphthalocyanine)

Figure 10:
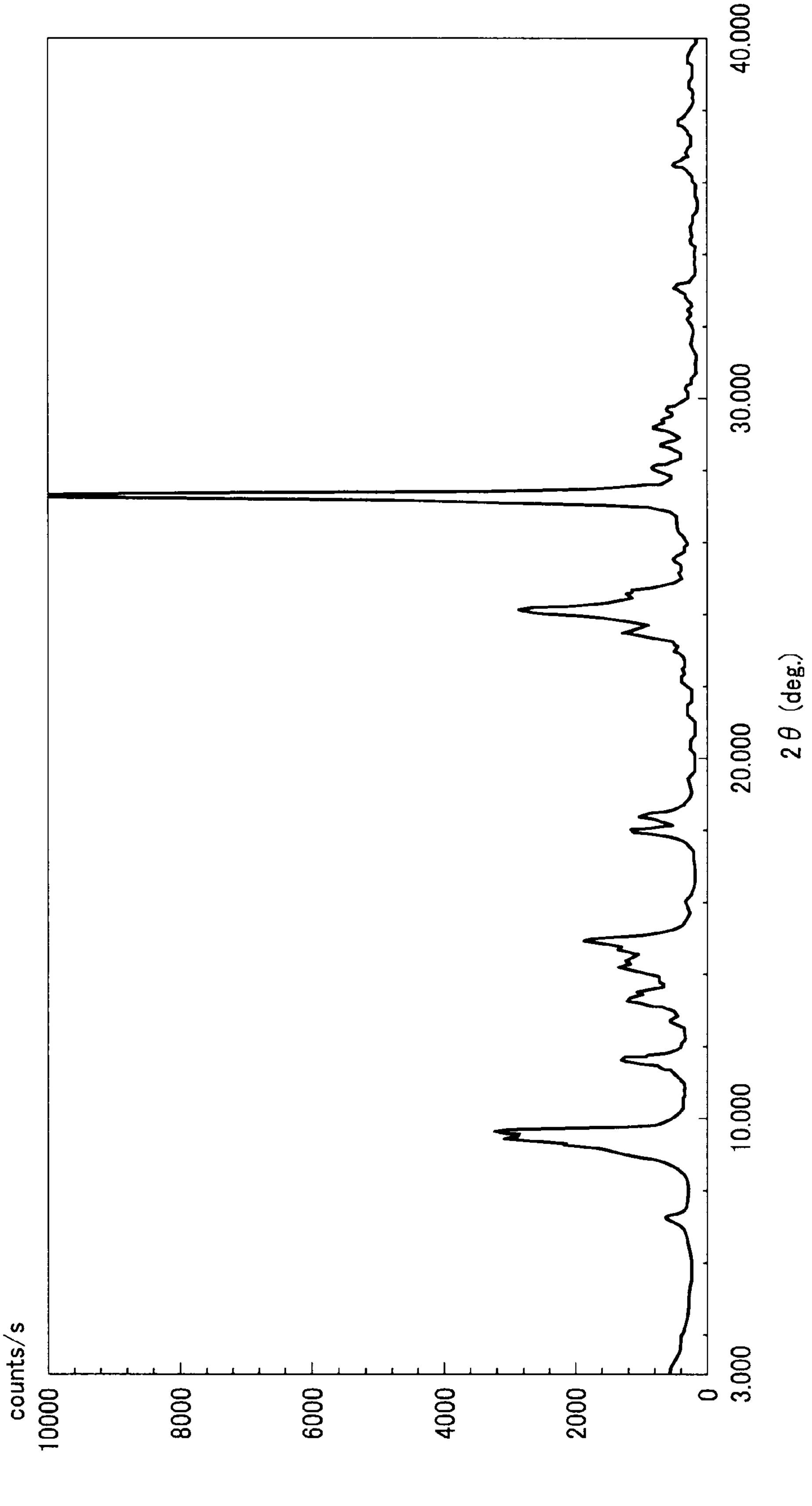
FIG. 10 is a chart showing a XD spectrum of an oxotitaniumphthalocyaninc powder for use in the present invention.
Figure 11:
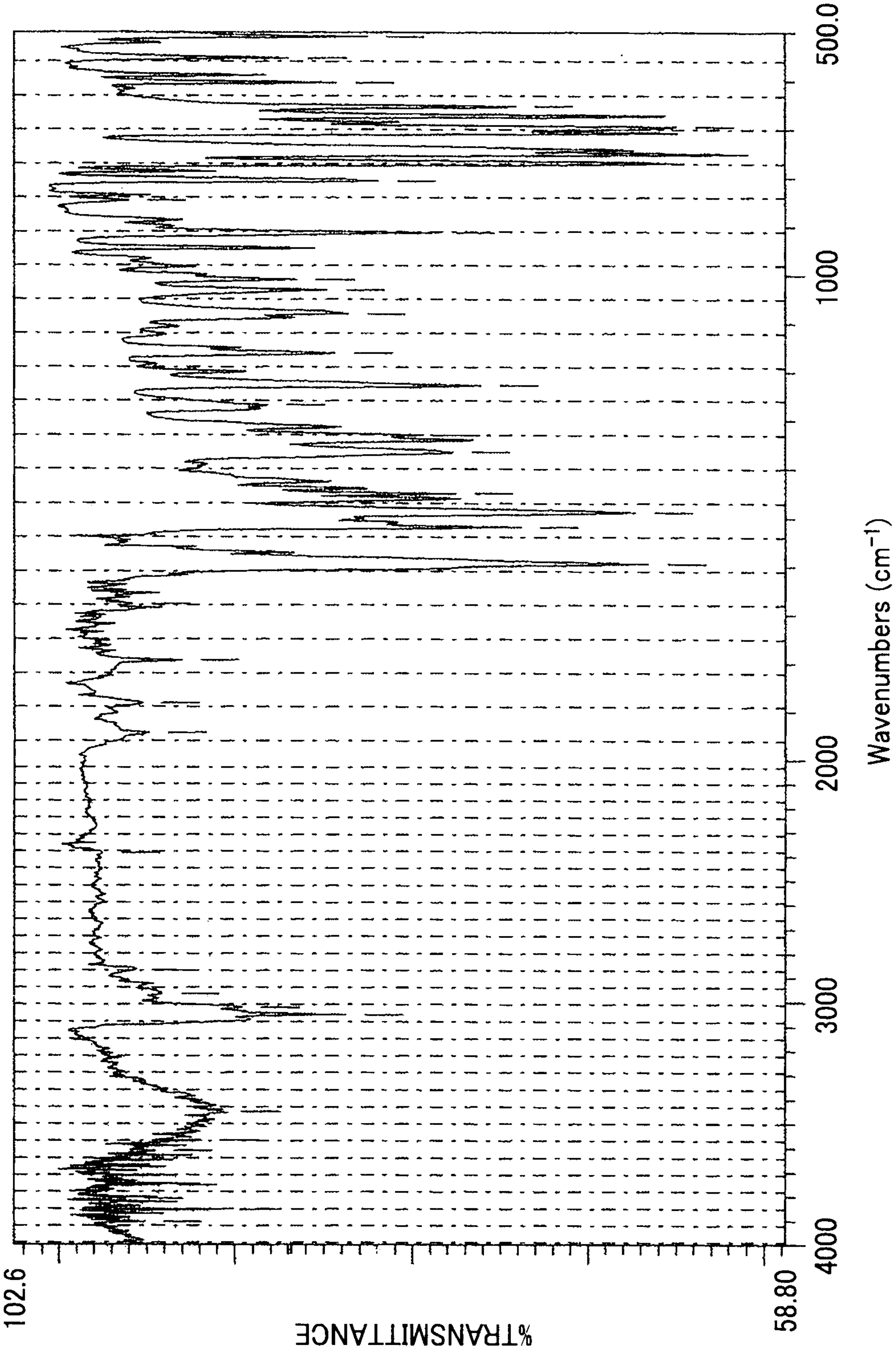
FIG. 11 is a chart showing an infrared absorption spectrum of an embodiment of the isoindole derivative as an oxidizing gas inhibitor of the present invention.

A pigment was prepared in accordance with Japanese Published Unexamined Patent Application No. 2001-19871. Namely, at first 29.2 g of 1,3-diiminoisoindoline and 200 ml of sulfolane were mixed. Then 20.4 g of titanium tetrabutoxide was dropped into the mixture under a nitrogen gas flow. After the reaction, the reaction product was cooled, followed by filtering. The thus prepared wet cake was washed with chloroform until the cake colored blue. Then the cake was washed several times with methanol, followed by washing several times with hot water heated to 80° C. and drying. Thus, a crude titanylphthalocyanine was prepared. One part of the thus prepared crude titanylphthalocyanine was dropped into 20 parts of concentrated sulfuric acid to be dissolved therein. The solution was dropped into 100 parts of ice water while stirred, to precipitate a titanylphthalocyanine pigment. The pigment was obtained by filtering. The pigment was washed with ion-exchange water until the filtrate became neutral. Thus, a wet cake of a titanylphthalocyanine pigment was obtained. An x-ray diffraction spectrum of the wet cake when dried is shown in FIG. 10. Two (2) grams of the wet cake were added to 20 g of carbon disulfide, and the mixture was stirred for about 4 hours. One hundred (100) g of methanol were added thereto and the mixture was stirred for 1 hr, and then the mixture was filtered and the wet cake was dried to prepare a oxotitaniumphthalocyanine powder.

| (CGL coating liquid) | |
|---|---|
| Oxotitaniumphthalocyanine having the XD spectrum in FIG. 10 | 8 |
| Polyvinylbutyral (BX-1) | 5 |
| 2-butanone | 400 |
| (CTL coating liquid) | |
| Polycarbonate resin (Z-polyca) | 10 |
| Isoindole derivative No. 7 | 1 |
| CTM No. 8 having the following formula | 7 |

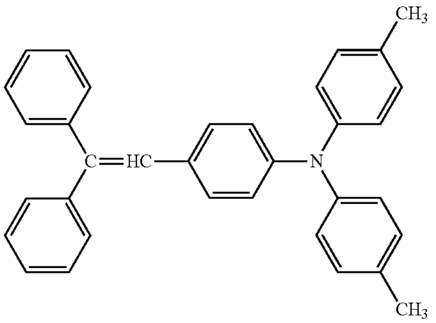 [SMILES: Cc1ccc(N(c2ccc(C)cc2)c2ccc(C=C(c3ccccc3)c3ccccc3)cc2)cc1]

| | |
|---|---|
| Toluene | 70 |

Example 52

The procedure for preparation and evaluation of the photoreceptor No. 16 in Example 20 was repeated to prepare and evaluate and a photoreceptor No. 48 except for using the isoindole derivative No. 30 instead of the isoindole derivative No. 8, and replacing the CGL coating liquid and the CTL coating liquid with ones having the following formulations. The evaluation results of the photoreceptor No. 48 are shown in Table 8.

| (CGL coating liquid) | |
|---|---|
| Oxotitaniumphthalocyanine having the XD spectrum in FIG. 10 | 8 |
| Polyvinylbutyral (BX-1) | 5 |
| 2-butanone | 400 |

-continued

| (CTL coating liquid) | |
|---|---|
| Polycarbonate resin (Z-polyca) | 10 |
| Isoindole derivative No. 30 | 1 |
| CTM No. 8 | 7 |
| Toluene | 70 |

TABLE 8

| | | | Initial | | After 100,000 | |
|---|---|---|---|---|---|---|
| Example No. | Photoreceptor No. | Derivative No. | Bright space potential (V) | Dot sharpness | Dark space potential (V) | Dot sharpness |
| 51 | 47 | 7 | −90 | 5 | −105 | 5 |
| 52 | 48 | 30 | −105 | 5 | −110 | 5 |

Example 53

On an aluminum cylinder having a diameter of 100 mm, a photosensitive layer coating liquid having the following formulation was coated and dried to form a single-layered photosensitive layer 30 μm thick thereon. Thus, an electrophotographic photoreceptor No. 49 was prepared.

| (Photosensitive layer coating liquid) | |
|---|---|
| X-type metal-free phthalocyanine (Fastogen Blue 8120B from Dainippon Ink And Chemicals, Inc.) | 2 |
| CTM having the following formula | 20 |

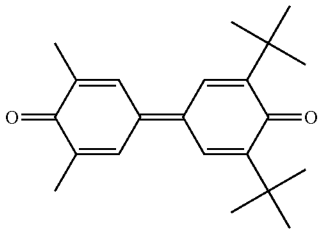 [SMILES: CC1=CC(=C2C=C(C(C)(C)C)C(=O)C(C(C)(C)C)=C2)C=C(C)C1=O]

| | |
|---|---|
| Isoindole derivative No. 8 | 30 |
| Bisphenol Z polycarobonate (Panlite TS-2050 from Teijin Chemicals Ltd.) | 50 |
| Tetrahydrofuran | 500 |

The photoreceptor was installed in imagio Neo 752 modified to have a scorotron corona charger and an LD having a wavelength of 780 nm from Ricoh Company, Ltd. The dark space potential thereof was set at +700 (V), 100,000 images were continuously produced thereby. The initial dark space potential and a bright space potential were measured. Dot images were evaluated as they were in Example 5. The evaluation results are shown in Table 9.

Example 54

The procedure for preparation and evaluation of the photoreceptor No. 49 in Example 53 was repeated to prepare and evaluate and a photoreceptor No. 50 except for using the isoindole derivative No. 16 instead of the isoindole derivative No. 8. The evaluation results of the photoreceptor No. 50 are shown in Table 9.

Example 55

The procedure for preparation and evaluation of the photoreceptor No. 49 in Example 53 was repeated to prepare and evaluate and a photoreceptor No. 51 except for using the isoindole derivative No. 20 instead of the isoindole derivative No. 8. The evaluation results of the photoreceptor No. 51 are shown in Table 9.

Example 56

The procedure for preparation and evaluation of the photoreceptor No. 49 in Example 53 was repeated to prepare and evaluate and a photoreceptor No. 52 except for using the isoindole derivative No. 33 instead of the isoindole derivative No. 8. The evaluation results of the photoreceptor No. 52 are shown in Table 9.

TABLE 9

| | | | Initial | | After 100,000 | |
|---|---|---|---|---|---|---|
| Example No. | Photoreceptor No. | Derivative No. | Bright space potential (V) | Dot sharpness | Dark space potential (V) | Dot sharpness |
| 53 | 49 | 8 | 90 | 5 | 100 | 5 |
| 54 | 50 | 16 | 105 | 5 | 115 | 5 |
| 55 | 51 | 20 | 100 | 5 | 115 | 5 |
| 56 | 52 | 33 | 105 | 5 | 115 | 4 |

Example 57

The procedure for preparation and evaluation of the photoreceptor No. 49 in Example 53 was repeated to prepare and evaluate and a photoreceptor No. 53 except for coating the photosensitive layer coating liquid on an aluminum cylinder having a diameter of 30 mm and using the isoindole derivative No. 1 instead of the isoindole derivative No. 8. The evaluation results of the photoreceptor No. 53 are shown in Table 10.

Example 58

The procedure for preparation and evaluation of the photoreceptor No. 53 in Example 57 was repeated to prepare and evaluate and a photoreceptor No. 54 except for using the isoindole derivative No. 16 instead of the isoindole derivative No. 8. The evaluation results of the photoreceptor No. 54 are shown in Table 10.

Example 59

The procedure for preparation and evaluation of the photoreceptor No. 53 in Example 57 was repeated to prepare and evaluate and a photoreceptor No. 55 except for using the isoindole derivative No. 20 instead of the isoindole derivative No. 8. The evaluation results of the photoreceptor No. 55 are shown in Table 10.

Example 60

The procedure for preparation and evaluation of the photoreceptor No. 53 in Example 57 was repeated to prepare and evaluate and a photoreceptor No. 56 except for using the isoindole derivative No. 30 instead of the isoindole derivative No. 8. The evaluation results of the photoreceptor No. 56 are shown in Table 10.

TABLE 10

| | | | Initial | | After 100,000 | |
|---|---|---|---|---|---|---|
| Example No. | Photoreceptor No. | Derivative No. | Bright space potential (V) | Dot sharpness | Dark space potential (V) | Dot sharpness |
| 57 | 53 | 8 | −95 | 5 | −115 | 5 |
| 58 | 54 | 16 | −110 | 5 | −125 | 5 |
| 59 | 55 | 20 | −105 | 5 | −120 | 4 |
| 60 | 56 | 30 | −110 | 5 | −135 | 4 |

Example 61

On an aluminum cylinder having a diameter of 100 mm, a CTL coating liquid and a CGL coating liquid having the following formulations were coated and dried in this order to form a CTL 20 μm thick and a CGL 0.1 μm thick thereon. Thus, an electrophotographic photoreceptor No. 57 was prepared, and evaluated as the photoreceptor No. 49 in Example 53 was. The evaluation results of the photoreceptor No. 57 are shown in Table 11.

| (CTL coating liquid) | |
|---|---|
| Bisphenol A polycarbonate (Panlite C-1400 from Teijin Chemicals Ltd.) | 10 |
| Toluene | 100 |
| Isoindole derivative No. 1 | 10 |
| (CGL coating liquid) | |
| Polyvinylbutyral (XYHL from UCC) | 0.5 |
| Cyclohexanone | 200 |
| Methyl ethyl ketone | 80 |
| X-type metal-free phthalocyanine (Fastogen Blue 8120B from Dainippon Ink And Chemicals, Inc.) | 2 |

Example 62

The procedure for preparation and evaluation of the photoreceptor No. 57 in Example 61 was repeated to prepare and evaluate and a photoreceptor No. 58 except for using the isoindole derivative No. 16 instead of the isoindole derivative No. 1. The evaluation results of the photoreceptor No. 58 are shown in Table 11.

Example 63

The procedure for preparation and evaluation of the photoreceptor No. 57 in Example 61 was repeated to prepare and evaluate and a photoreceptor No. 59 except for using the isoindole derivative No. 20 instead of the isoindole derivative No. 1. The evaluation results of the photoreceptor No. 59 are shown in Table 11.

Example 64

The procedure for preparation and evaluation of the photoreceptor No. 57 in Example 61 was repeated to prepare and evaluate and a photoreceptor No. 60 except for using the isoindole derivative No. 30 instead of the isoindole derivative No. 1. The evaluation results of the photoreceptor No. 60 are shown in Table 11.

TABLE 11

| | | | Initial | | After 100,000 | |
|---|---|---|---|---|---|---|
| Example No. | Photoreceptor No. | Derivative No. | Bright space potential (V) | Dot sharpness | Dark space potential (V) | Dot sharpness |
| 61 | 57 | 1 | 85 | 5 | 95 | 5 |
| 62 | 58 | 16 | 95 | 5 | 110 | 4 |
| 63 | 59 | 20 | 90 | 5 | 105 | 5 |
| 64 | 60 | 30 | 100 | 5 | 125 | 5 |

Example 65

The procedure for preparation and evaluation of the photoreceptor No. 16 in Example 20 was repeated to prepare and evaluate and a photoreceptor No. 61 except for replacing the CTL coating liquid with a CTL coating liquid having the following formulation and changing the charging method to a positive corona charging (scorotron method). The evaluation results of the photoreceptor No. 61 are shown in Table 12.

| (CTL coating liquid) | |
|---|---|
| Polycarbonate resin (Z-polyca) | 10 |
| Isoindole derivative No. 8 | 1 |
| CTM having the following formula | 9 |
| 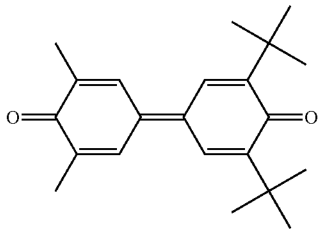 [SMILES: CC1=CC(=C2C=C(C(C)(C)C)C(=O)C(C(C)(C)C)=C2)C=C(C)C1=O] | |
| Tetrahydrofuran | 100 |

Example 66

The procedure for preparation and evaluation of the photoreceptor No. 61 in Example 65 was repeated to prepare and evaluate and a photoreceptor No. 62 except for replacing the CTM with a CTM having the following formula. The evaluation results of the photoreceptor No. 62 are shown in Table 12.

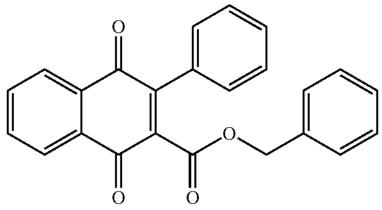 [SMILES: O=C(OCc1ccccc1)C1=C(c2ccccc2)C(=O)c2ccccc2C1=O]

Example 67

The procedure for preparation and evaluation of the photoreceptor No. 61 in Example 65 was repeated to prepare and evaluate and a photoreceptor No. 63 except for replacing the CTM with a CTM having the following formula. The evaluation results of the photoreceptor No. 63 are shown in Table 12.

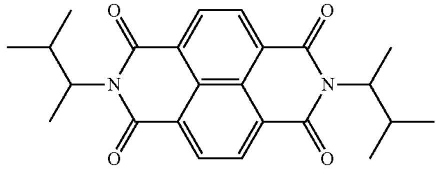 [SMILES: CC(C)C(C)N1C(=O)c2ccc3c4c(ccc(c24)C1=O)C(=O)N(C(C)C(C)C)C3=O]

Example 68

The procedure for preparation and evaluation of the photoreceptor No. 61 in Example 65 was repeated to prepare and evaluate and a photoreceptor No. 64 except for replacing the CTM with a CTM having the following formula. The evaluation results of the photoreceptor No. 64 are shown in Table 12.

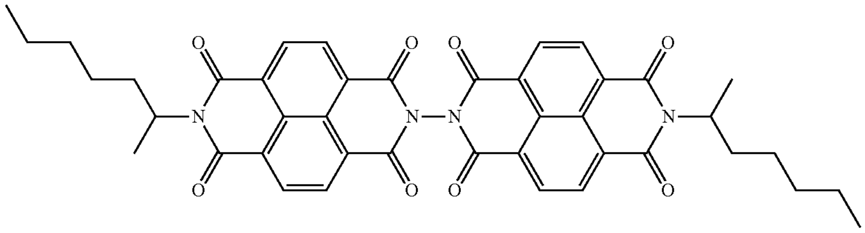 [SMILES: CCCCCC(C)N1C(=O)c2ccc3c4c(ccc(c24)C1=O)C(=O)N(N1C(=O)c2ccc4c5c(ccc(c25)C1=O)C(=O)N(C(C)CCCCC)C4=O)C3=O]

TABLE 12

| | | | Initial | | After 100,000 | |
|---|---|---|---|---|---|---|
| Example No. | Photoreceptor No. | Derivative No. | Bright space potential (V) | Dot sharpness | Dark space potential (V) | Dot sharpness |
| 65 | 61 | 8 | 105 | 5 | 120 | 5 |
| 66 | 62 | 8 | 100 | 5 | 115 | 5 |
| 67 | 63 | 8 | 95 | 5 | 100 | 5 |
| 68 | 64 | 8 | 90 | 5 | 115 | 5 |

Comparative Example 1

The procedure for preparation and evaluation of the photoreceptor No. 1 in Example 5 was repeated to prepare and evaluate and a comparative photoreceptor No. 1 except for replacing the isoindole derivative No. 2 with a benzoquinone derivative having the following formula. The evaluation results of the comparative photoreceptor No. 1 are shown in Table 13.

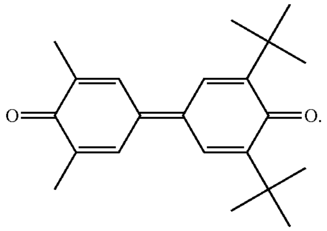 [SMILES: CC1=CC(=C2C=C(C(C)(C)C)C(=O)C(C(C)(C)C)=C2)C=C(C)C1=O]

Comparative Example 2

The procedure for preparation and evaluation of the photoreceptor No. 16 in Example 20 was repeated to prepare and evaluate and a comparative photoreceptor No. 2 except for not adding the isoindole derivative to the CTL coating liquid and changing the weight by part of the CTM to 10 parts. The evaluation results of the comparative photoreceptor No. 1 are shown in Table 13.

Comparative Example 3

The procedure for preparation and evaluation of the photoreceptor No. 35 in Example 39 was repeated to prepare and evaluate and a comparative photoreceptor No. 3 except for replacing the isoindole derivative with a tetraphenylmethane compound (Japanese published unexamined application No 2000-231204) having the following formula. The evaluation results of the comparative photoreceptor No. 3 are shown in Table 13.

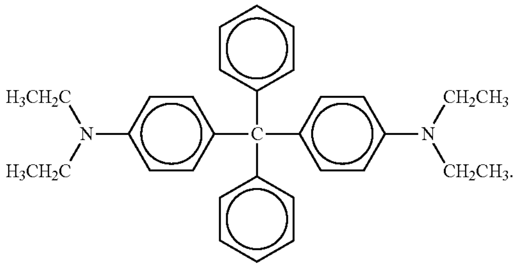

Comparative Example 4

The procedure for preparation and evaluation of the photoreceptor No. 47 in Example 51 was repeated to prepare and evaluate and a comparative photoreceptor No. 4 except for replacing the isoindole derivative with a hindered amine antioxidant having the following formula. The evaluation results of the comparative photoreceptor No. 4 are shown in Table 13.

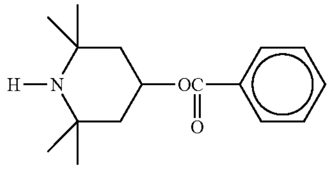

Comparative Example 5

The procedure for preparation and evaluation of the photoreceptor No. 49 in Example 53 was repeated to prepare and evaluate and a comparative photoreceptor No. 5 except for replacing the isoindole derivative with a CTM having the following formula. The evaluation results of the comparative photoreceptor No. 5 are shown in Table 13.

CTM having the following formula 30

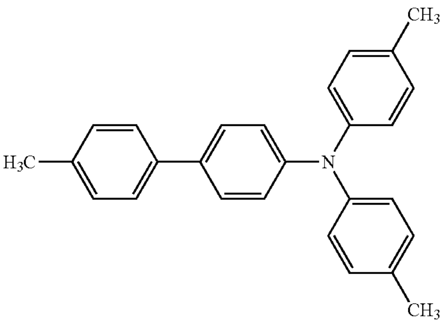

Comparative Example 6

The procedure for preparation and evaluation of the photoreceptor No. 49 in Example 53 was repeated to prepare and evaluate and a comparative photoreceptor No. 6 except for replacing the isoindole derivative with a CTM having the following formula. The evaluation results of the comparative photoreceptor No. 6 are shown in Table 13.

CTM having the following formula 30

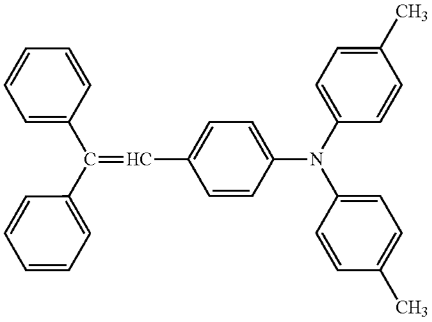 [SMILES: Cc1ccc(N(c2ccc(C)cc2)c2ccc(C=C(c3ccccc3)c3ccccc3)cc2)cc1]

Comparative Example 7

The procedure for preparation and evaluation of the photoreceptor No. 57 in Example 61 was repeated to prepare and evaluate and a comparative photoreceptor No. 7 except for replacing the isoindole derivative with a CTM having the following formula. The evaluation results of the comparative photoreceptor No. 7 are shown in Table 13.

CTM having the following formula

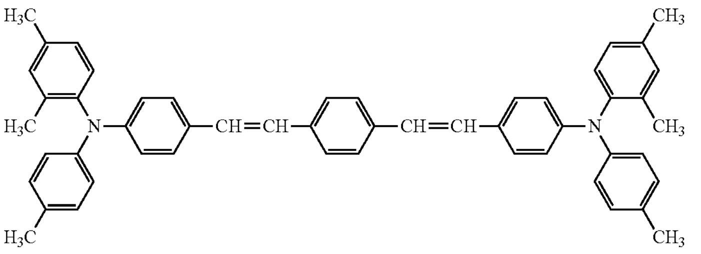 [SMILES: Cc1ccc(N(c2ccc(C=Cc3ccc(C=Cc4ccc(N(c5ccc(C)cc5)c5ccc(C)cc5C)cc4)cc3)cc2)c2ccc(C)cc2C)cc1]

TABLE 13

| Comparative Example No. | Comparative Photoreceptor No. | Initial Bright space potential (V) | Initial Dot sharpness | After 100,000 Dark space potential (V) | After 100,000 Dot sharpness |
|---|---|---|---|---|---|
| 1 | 1 | 180 | 3 | 470 | 1 |
| 2 | 2 | −250 | 5 | −355 | 2 |
| 3 | 3 | −500 | 4 | −655 | 1 |
| 4 | 4 | −485 | 2 | −565 | 1 |
| 5 | 5 | 110 | 5 | 125 | 1 |
| 6 | 6 | 115 | 4 | 130 | 1 |
| 7 | 7 | −100 | 4 | −170 | 1 |

The above-mentioned evaluation results prove that the photoreceptors including an isoindole derivative of the present invention has less increase of bright space potential even after 100,000 images are produced and stably produce high-quality images. In contrast, the comparative photoreceptors 1, 3 and 4 had high bright space potential from the beginning, which caused deterioration of image density and image resolution. After 100,000 images were produced, the image gradation noticeably deteriorated, resulting in production of unreadable images. Tables 2 and 10 prove that the photoreceptors of the present invention produced quality images even when positively charged. Even after 100,000 images were produced, quality images having good dot sharpness were produced. The comparative photoreceptors 2, 5, 6 and 7 deteriorated in image resolution due to repeated use more than the photoreceptors of the present invention, although having less increase of bright space potential.

Examples 69 to 75 and Comparative Example 8

Durability Test

The photoreceptors Nos. 1, 17, 33, 37, 48, 49 and 59, and comparative photoreceptor No. 2 were left in a desiccator including NOx of 50 ppm for 4 days. Image evaluations before and after they left therein are shown in Table 14.

TABLE 14

| Example No. | Photoreceptor No. | Before | After |
|---|---|---|---|
| 69 | 1 | 5 | 5 |
| 70 | 17 | 5 | 5 |
| 71 | 33 | 5 | 4 |
| 72 | 37 | 5 | 5 |
| 73 | 48 | 5 | 4 |
| 74 | 49 | 5 | 4 |
| 75 | 59 | 5 | 5 |
| Comparative Example 8 | Comparative Photoreceptor 2 | 5 | 1 |

Table 14 proves that photoreceptors including an isoindole derivative of the present invention largely improve in resistance to oxidizing gases, i.e., prevention of deterioration of image resolution. In contrast, Comparative Photoreceptor 2 initially produced quality images, but noticeably deteriorated in image resolution due to oxidizing gases.

Figure 12:
FIG. 12 is a chart showing image qualities under specified conditions.
Figure 12:
Figure 12:
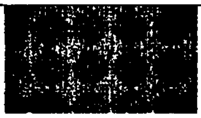
Figure 12:
Figure 12:
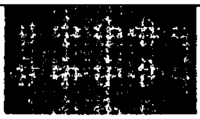
Figure 12:
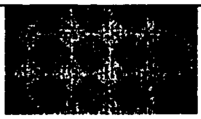
Figure 12:
Figure 12:
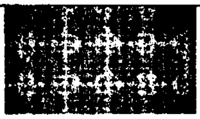
Figure 12:
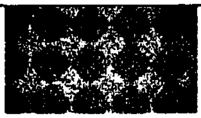
Figure 12:
Figure 12:
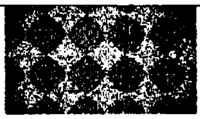
Figure 12:
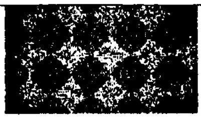
Figure 12:
Figure 12:
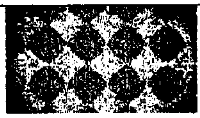
Figure 12:
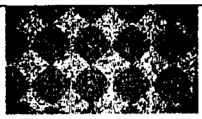

Image qualities were evaluated under the standards shown in FIG. 12, using a magnifier.

What is claimed is:

1. An N-phenyl-diphenylisoindole derivative selected from the group consisting of the following compounds (3)-(36):

(3)

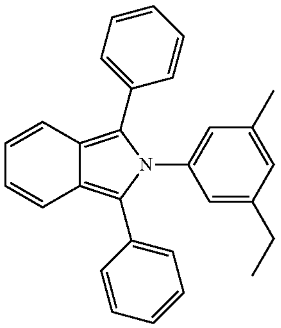

-continued
(4)
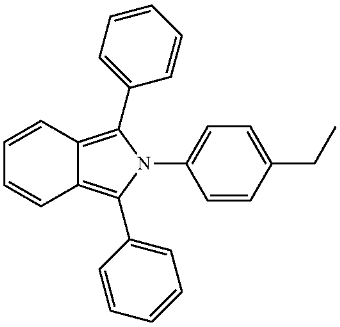
(5)
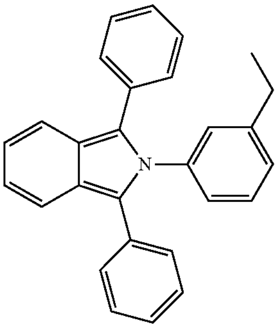
(6)
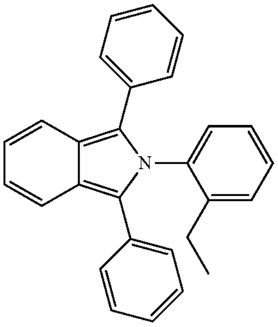
(7)
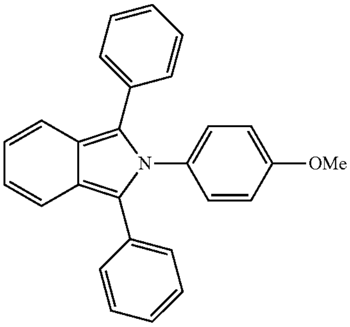
-continued
(8)
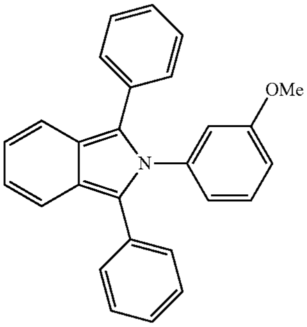
(9)
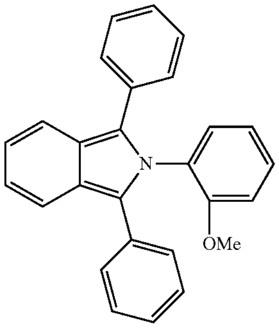
(10)
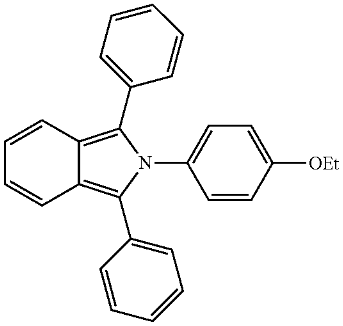
(11)
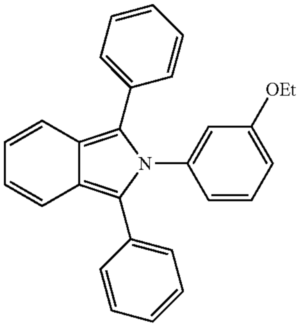

-continued
(12)
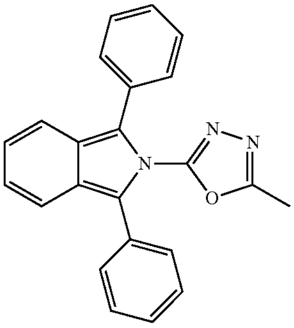
(13)
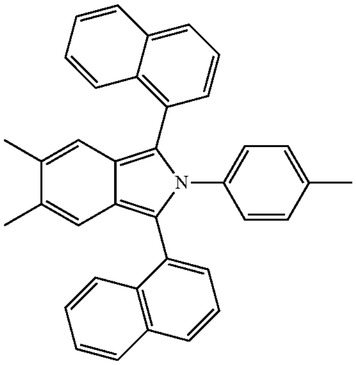
(14)
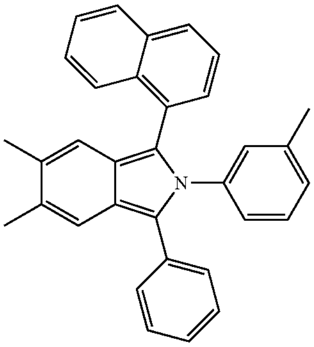
(15)
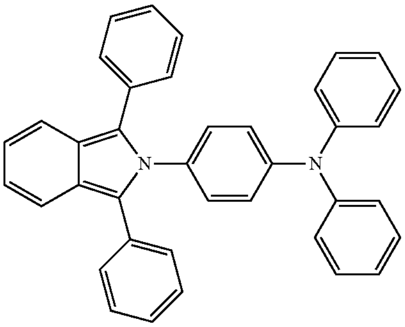
-continued
(16)
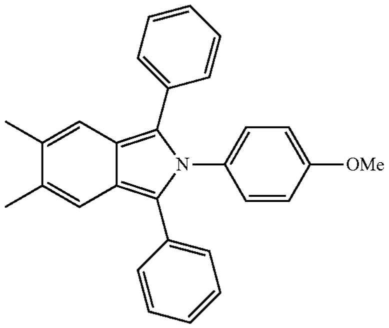
(17)
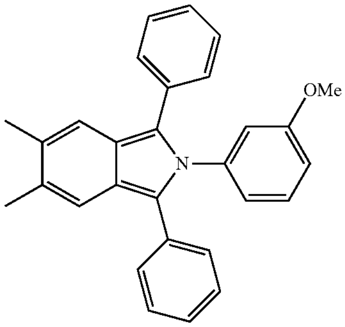
(18)
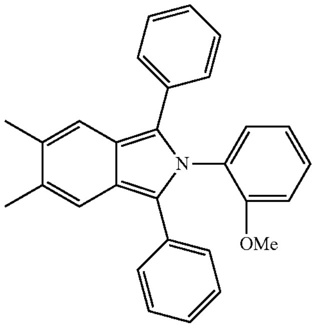
(19)
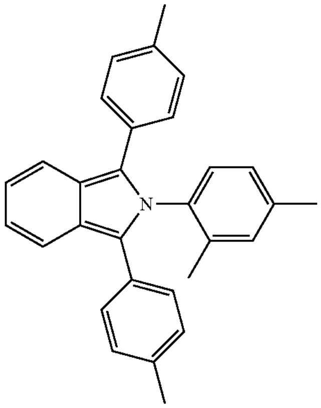

-continued
(20)
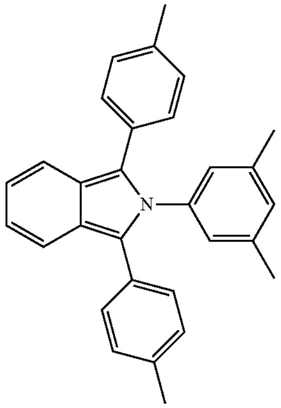
(21)
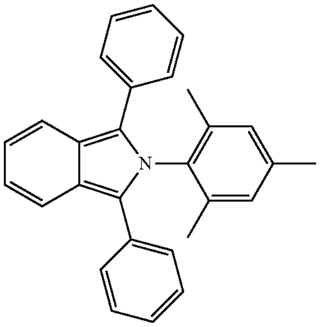
(22)
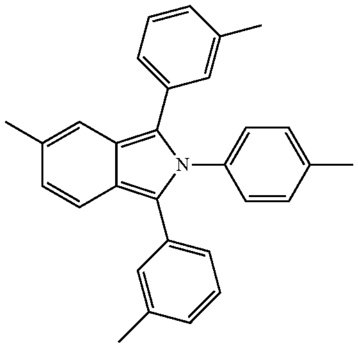
(23)
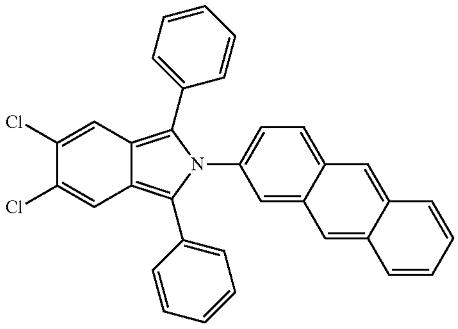
-continued
(24)
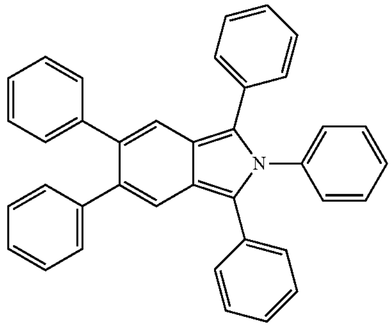
(25)
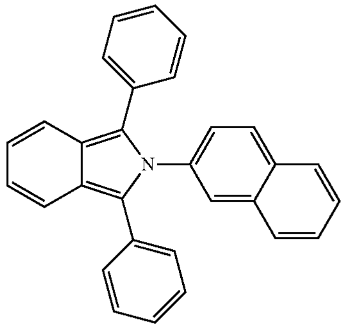
(26)
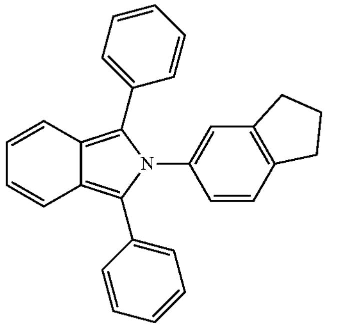
(27)
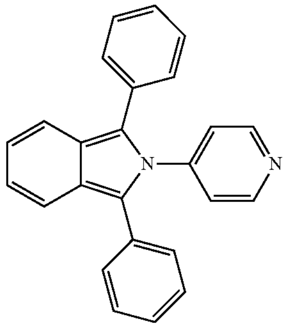

(28)
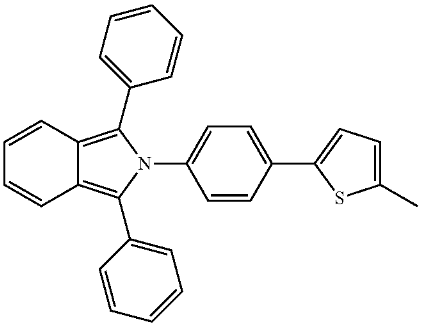
(29)
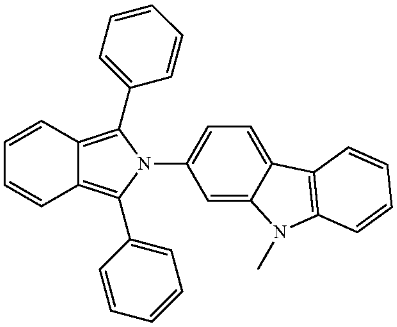
(30)
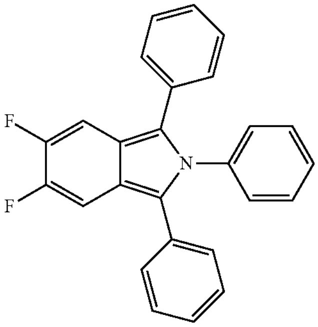
(31)
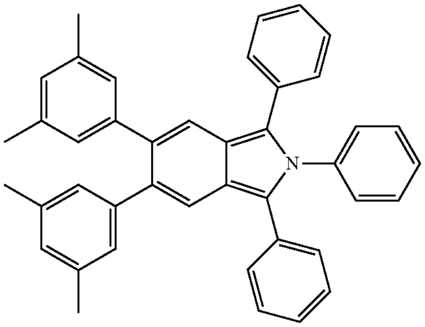
(32)
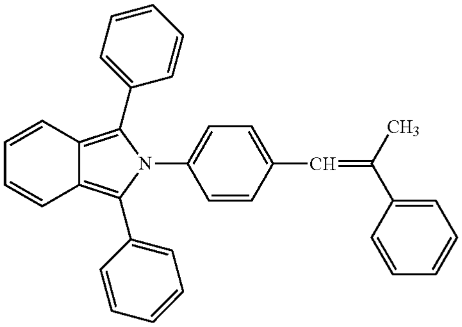
(33)
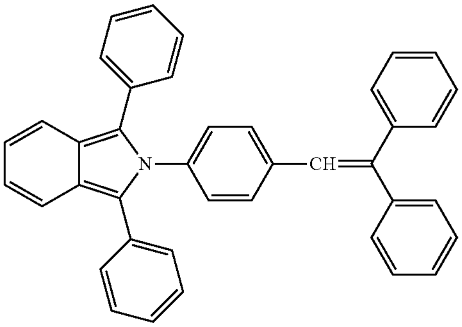
(34)
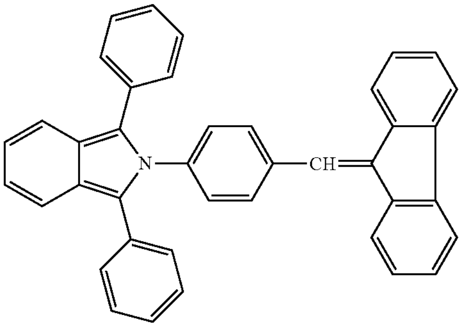
(35)
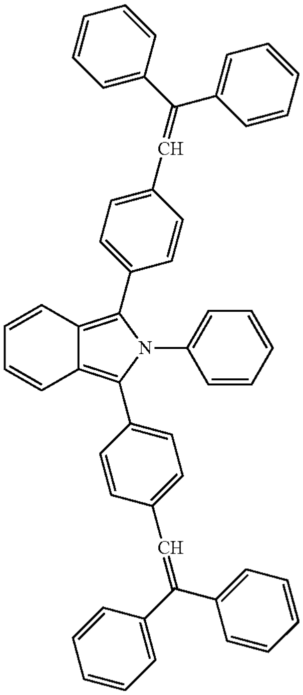
and -continued (36)

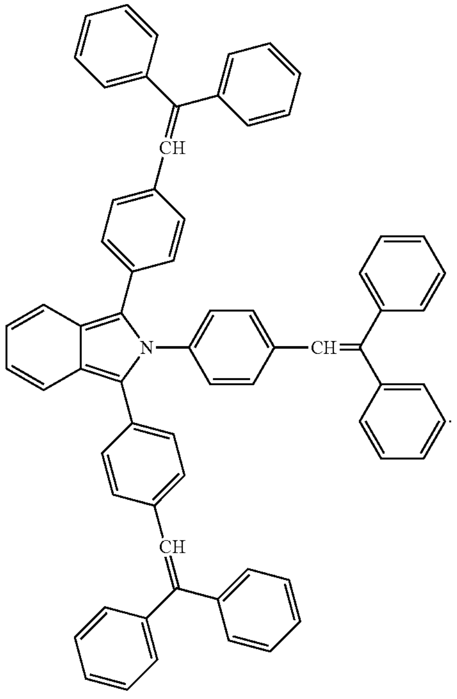

2. A method of preparing the N-phenyl-diphenylisoindole derivative of formula (1):

(1)

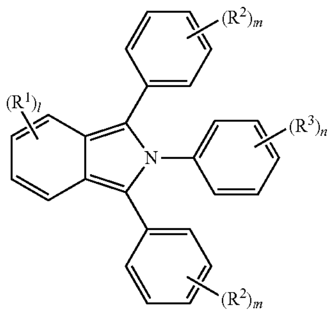

wherein $R^1$ represents a hydrogen or a methyl group, $R^2$ represents a hydrogen atom; $R^3$ represents a substituted or an unsubstituted alkyl group, a substituted or an unsubstituted alkoxy group, or a group of formula (2):

(2)

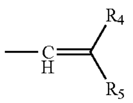

wherein each of $R_4$ and $R_5$ represents a substituted or an unsubstituted alkyl group, or a substituted or an unsubstituted aryl group; 1 represents an integer of 2; and each of m and n represents an integer of from 1 to 5, comprising:

reacting a diketone derivative of formula (3) with an amine derivative of formula (4);

(3)

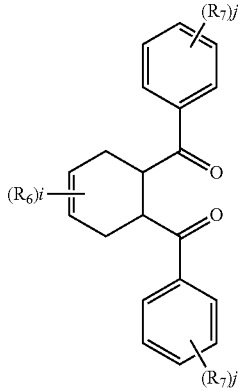

(4)

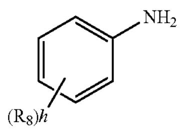

wherein $R^6$ represents a hydrogen or a methyl group; $R^7$ represents a hydrogen atom; $R^8$ represents a substituted or an unsubstituted alkyl group, a substituted or an unsubstituted alkoxy group, or a group of formula (2); and i represents an integer of 2; and each of j and h represents an integer of from 1 to 5.

3. An electrophotographic photoreceptor, comprising:

an electroconductive substrate; and a photosensitive layer overlying the electroconductive substrate, comprising an N-phenyl-diphenylisoindole derivative of claim 1.

4. The electrophotographic photoreceptor of claim 3, wherein the photosensitive layer further comprises a charge transport material of formula (9):

(9)

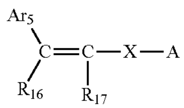

wherein X represents a single bond or a vinylene group; $R_{17}$ represents a hydrogen atom, a substituted or an unsubstituted alkyl group, or a substituted or an unsubstituted aromatic hydrocarbon group; $Ar_s$ represents a substituted or an unsubstituted aromatic hydrocarbon group; $R_{16}$ represents a hydrogen atom, a substituted or an unsubstituted alkyl group, or a substituted or an unsubstituted aromatic hydrocarbon group; $Ar_s$ and $R_{16}$ may form a ring together; A represents a group of formula (10), a group of formula (11), a 9-anthryl group or a substituted or an unsubstituted carbazolyl group:

(10)

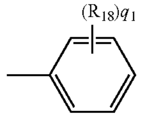

-continued (11)

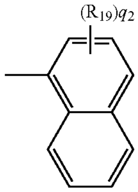

wherein each of $R_{18}$ and $R_{19}$ represents a hydrogen atom, an alkyl group, an alkoxy group, a halogen atom or a group of formula (12):

(12)

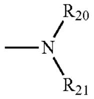

wherein each of $R_{20}$ and $R_{21}$ represents a substituted or an unsubstituted alkyl group, or a substituted or an unsubstituted aromatic hydrocarbon group, and may be the same or different from each other and may form a ring together; each of q1 and q2 represents an integer of from 1 to 3; and $R_{18}$ and $R_{19}$ may be the same or different from each other when q1 or q2 is not less than 2.

5. The electrophotographic photoreceptor of claim 4, wherein the charge transport material is an aryl amine derivative of formula (13):

(13)

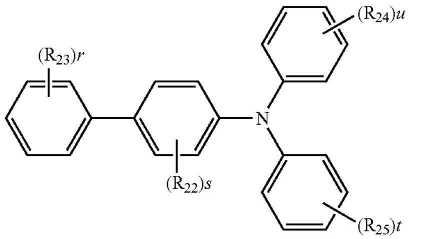

wherein each of $R_{23}$, $R_{24}$ and $R_{25}$ represents a hydrogen atom, an amino group, an alkoxy group, a thioalkoxy group, an aryloxy group, a methylenedioxy group, a substituted or an unsubstituted alkyl group, a halogen atom, or a substituted or an unsubstituted aromatic hydrocarbon group; $R_{22}$ represents a hydrogen atom, an alkoxy group, a substituted or an unsubstituted alkyl group, or a halogen atom; each of r, s, t and u is an integer of from 1 to 4;

and $R_{22}$, $R_{23}$, $R_{24}$ and $R_{25}$ may be the same or different from each other when each of r, s, t and u is an integer of from 2 to 4.

6. The electrophotographic photoreceptor claim 4, wherein the charge transport material is an aryl amine derivative of formula (14):

(14)

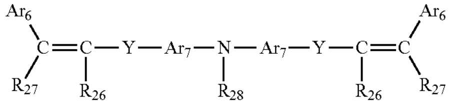

wherein Y represents a single bond or a vinylene group; $R_{26}$ represents a hydrogen atom, a substituted or an unsubstituted alkyl group, or a substituted or an unsubstituted aromatic hydrocarbon group; $Ar_6$ represents a substituted or an unsubstituted aromatic hydrocarbon group; $R_{27}$ represents a hydrogen atom, a substituted or an unsubstituted alkyl group, or a substituted or an unsubstituted aromatic hydrocarbon group; $Ar_6$ and $R_{27}$ may form a ring together; $Ar_7$ represents a group of formula (15) or (16):

(15)

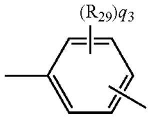

(16)

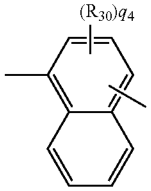

wherein each of $R_{29}$ and $R_{30}$ represents a hydrogen atom, an alkyl group, an alkoxy group or a halogen atom; each of $q_3$ and $q_4$ represents an integer of form 1 to 3; $R_{29}$ and $R_{30}$ may be the same or different from each other when each of $q_3$ and $q_4$ is 2 or 3; and $R_{28}$ represents a substituted or an unsubstituted alkyl group, or a substituted or an unsubstituted aromatic hydrocarbon group.

7. The electrophotographic photoreceptor claim 4, wherein the charge transport material is an aryl amine derivative of formula (17):

(17)

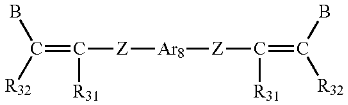

wherein Z represents a single bond or a vinylene group; $R_{31}$ represents a hydrogen atom, a substituted or an unsubstituted alkyl group, or a substituted or an unsubstituted aromatic hydrocarbon group; $Ar_8$ represents a substituted or an unsubstituted bivalent aromatic hydrocarbon group; $R_{32}$ represents a hydrogen atom, a substituted or an unsubstituted alkyl group, or a substituted or an unsubstituted aromatic hydrocarbon group; Z represents a group of formula (18), a group of formula (19), a 9-anthryl group or a substituted or an unsubstituted carbazolyl group:

(18)

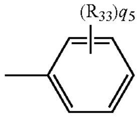

(19)

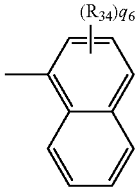

wherein each of $R_{33}$ and $R_{34}$ represents a hydrogen atom, an alkyl group, an alkoxy group, a halogen atom or a group of formula (20):

(20)

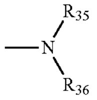

wherein each of $R_{35}$ and $R_{36}$ represents a substituted or an unsubstituted alkyl group, or a substituted or an unsubstituted aromatic hydrocarbon group, and may be the same or different from each other and may form a ring together; each of $q_5$ and $q_6$ represents an integer of from 1 to 3; and $R_{33}$ and $R_{34}$ may be the same or different from each other when $q_5$ or q6 is not less than 2.

8. The electrophotographic photoreceptor claim 4, wherein the charge transport material is a quinone derivative of formula (21):

(21)

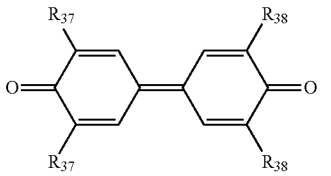

wherein each of $R_{37}$ and $R_{38}$ represents a hydrogen atom, a substituted or an unsubstituted alkyl group, or a substituted or an unsubstituted aromatic hydrocarbon group, and may be the same or different from each other.

9. The electrophotographic photoreceptor of claim 4, wherein the charge transport material is a naphthoquinone derivative of formula (22):

(22)

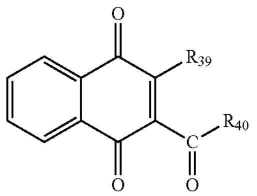

wherein $R_{39}$ represents a substituted or an unsubstituted alkyl group, or a substituted or an unsubstituted aryl group; $R_{40}$ represents a substituted or an unsubstituted alkyl group, or a substituted or an unsubstituted aromatic hydrocarbon group, or a group having the following formula (23):

(23)

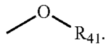

wherein $R_{41}$ represents a substituted or an unsubstituted alkyl group, or a substituted or an unsubstituted aryl group.

10. The electrophotographic photoreceptor of claim 4, wherein the charge transport material is a naphthalene tetracarboxylic imide derivative of formula (24):

(24)

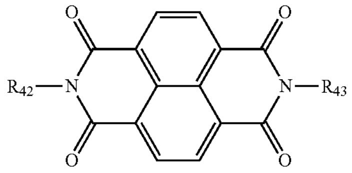

wherein each of $R_{42}$ and $R_{43}$ represents a hydrogen atom, a substituted or an unsubstituted alkyl group, or a substituted or an unsubstituted aromatic hydrocarbon group, and may be the same or different from each other.

11. The electrophotographic photoreceptor of claim 4, wherein the charge transport material is a naphthalene tetracarboxylic imide derivative of formula (25):

(25)

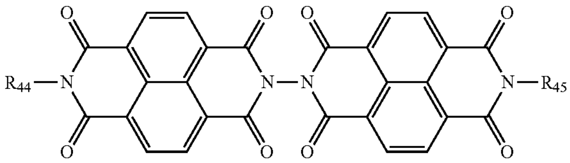

wherein each of $R_{44}$ and $R_{45}$ represents a hydrogen atom, a substituted or an unsubstituted alkyl group, or a substituted or an unsubstituted aromatic hydrocarbon group, and may be the same or different from each other.

12. The electrophotographic photoreceptor of claim 3, wherein the photosensitive layer further comprises a charge generation layer and a charge transport layer.

13. The electrophotographic photoreceptor of claim 3, wherein the photosensitive layer is a single-layered photosensitive layer.

14. The electrophotographic photoreceptor of claim 3, which can negatively and positively be charged.

15. An electrophotographic image forming method, comprising:

charging the electrophotographic photoreceptor according to claim 3;

irradiating the electrophotographic photoreceptor to form an electrostatic latent image thereon;

developing the electrostatic latent image with a toner to form a toner image; and transferring the toner image onto a transfer material.

16. The electrophotographic image forming method of claim 15, wherein the irradiating the electrophotographic photoreceptor with an LD or an LED to form an electrostatic latent image thereon.

17. An electrophotographic image forming apparatus, comprising:

a charger configured to charge the electrophotographic photoreceptor according to claim 3;

an irradiator configured to irradiate the electrophotographic photoreceptor to form an electrostatic latent image thereon;

an image developer configured to developthe electrostatic latent image with a toner to form a toner image; and a transferer configured to transfer the toner image onto a transfer material.

18. The electrophotographic image forming apparatus of claim 17, wherein the irradiator irradiates the electrophotographic photoreceptor with an LD or an LED to form an electrostatic latent image thereon.

19. A process cartridge detachable from electrophotographic image forming apparatus, comprising the electrophotographic photoreceptor according to claim 3, and one of a charger, an irradiator, an image developer, an image transferer, a cleaner and a discharger.

20. A method of preparing N-phenyl-diphenylisoindole derivative of formula (1):

(1)

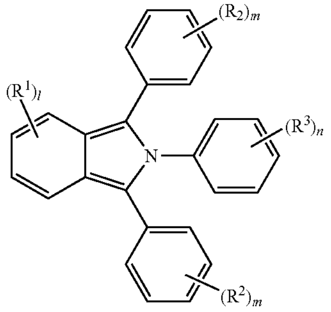

wherein each of $R^1$ and $R^2$ represents a hydrogen atom, a substituted or an unsubstituted alkyl group, a substituted or an unsubstituted alkoxy group, a substituted or an unsubstituted phenyl group, or a substituted or an unsubstituted phenoxy group; $R^3$ represents a hydrogen atom, a substituted or an unsubstituted alkyl group, a substituted or an unsubstituted alkoxy group, a substituted or an unsubstituted phenyl group, a substituted or an unsubstituted phenoxy group, or a group of formula (2):

(2)

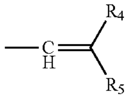

wherein each of $R_4$ and $R_5$ represents a substituted or an unsubstituted alkyl group, or a substituted or an unsubstituted phenyl group; 1 represents an integer of from 1 to 4; and each of m and n represents an integer of from 1 to 5;

the method comprising:

reacting a diketone derivative of formula (3) with an amine derivative of formula (4);

(3)

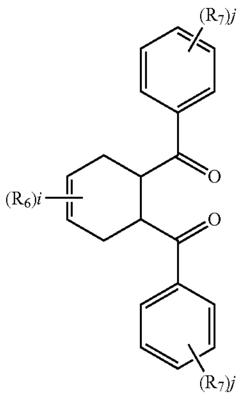

(4)

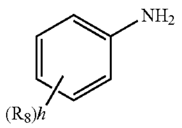

wherein each of $R^6$ and $R^7$ represents a hydrogen atom, a substituted or an unsubstituted alkyl group, a substituted or an unsubstituted alkoxy group, a substituted or an unsubstituted phenyl group, or a substituted or an unsubstituted phenoxy group; $R^8$ represents a hydrogen atom, a substituted or an unsubstituted alkyl group, a substituted or an unsubstituted alkoxy group, a substituted or an unsubstituted phenyl group, a substituted or an unsubstituted phenoxy group, or has the formula (2); and i represents an integer of from 1 to 4; and each of j and h represents an integer of from 1 to 5.

* * * * *